(12) United States Patent
Linders et al.

(10) Patent No.: US 7,332,524 B2
(45) Date of Patent: Feb. 19, 2008

(54) ADAMANTYL ACETAMIDES AS 11-BETA HYDROXYSTEROID DEHYDROGENASE INHIBITORS

(75) Inventors: Joannes Theodorus Maria Linders, Eindhoven (NL); Gustaaf Henri Maria Willemsens, Beerse (BE); Ronaldus Arnodus Hendrika Joseph Gilissen, Kasterlee (BE); Christophe Francis Robert Nestor Buyck, Temse (BE); Greta Constantia Peter Vanhoof, Zoersel (BE); Louis Jozef Elisabeth Van Der Veken, Vosselaar (BE); Libuse Jaroskova, Vosselaar (BE)

(73) Assignee: Janssen Pharmaceutica N.V., Beerse (BE)

( * ) Notice: Subject to any disclaimer, the term of this patent is extended or adjusted under 35 U.S.C. 154(b) by 0 days.

(21) Appl. No.: 10/540,616

(22) PCT Filed: Dec. 16, 2003

(86) PCT No.: PCT/EP03/51021

§ 371 (c)(1),
(2), (4) Date: Jun. 23, 2005

(87) PCT Pub. No.: WO2004/056745

PCT Pub. Date: Jul. 8, 2004

(65) Prior Publication Data

US 2006/0079506 A1    Apr. 13, 2006

(30) Foreign Application Priority Data

Dec. 23, 2002  (WO) .................. PCT/EP02/14832

(51) Int. Cl.
*A61K 31/165* (2006.01)
*C07C 233/57* (2006.01)

(52) U.S. Cl. ..................... 514/617; 564/133
(58) Field of Classification Search ................ 514/617; 564/133
See application file for complete search history.

(56) References Cited

U.S. PATENT DOCUMENTS 2,510,945 A    6/1950    Badgett et al.
3,526,656 A    9/1970    Butler (Continued)

FOREIGN PATENT DOCUMENTS

DE    1959898    6/1970

(Continued)

OTHER PUBLICATIONS

STN search report: Zhurnal Organicheskoi Khimii (1974), 10(4), 761-5.*

(Continued)

Primary Examiner—Rebecca Anderson
Assistant Examiner—Yong Chu

(57) ABSTRACT the N-oxide forms, the pharmaceutically acceptable addition salts and the stereochemically isomeric forms thereof, wherein n represents an integer being 1 or 2; $R^1$ and $R^2$ each independently represents hydrogen $C_{1-4}$alkyl, $NR^9R^{10}$, $C_{1-4}$alkyloxy; or $R^1$ and $R^2$ taken together with the carbon atom with which they are attached form a $C_{3-6}$cycloalkyl; and where n is 2, either $R^1$ or $R^2$ may be absent to form an unsaturated bond; $R^3$ represents a $C_{6-12}$cycloalkyl, preferably selected from cylo-octanyl and cyclohexyl or $R^3$ represents a monovalent radical having one of the following formulae

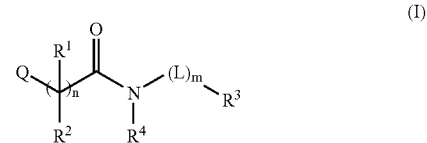

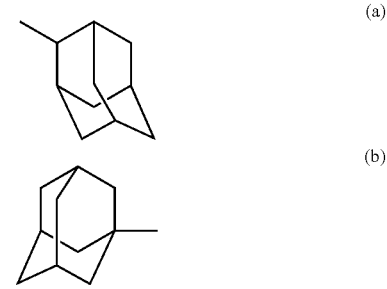

wherein said $C_{6-12}$cycloalkyl or monovalent radical may optionally be substituted with one, or where possible two, three or more substituents selected from the group consisting of $C_{1-4}$alkyl, $C_{1-4}$alkyloxy, halo or hydroxy; Q represents $Het^1$ or $Ar^2$ wherein said $C_{3-8}$cycloalkyl, $Het^1$ or $Ar^2$ are optionally substituted with one or where possible two or more substituents selected from halo, $C_{1-4}$alkyl, $C_{1-4}$alkyloxy, hydroxy, nitro, $NR^5R^6$, $C_{1-4}$alkyloxy substituted with one or where possible two, three or more substituents each independently selected from hydroxycarbonyl, $Het^2$ and $NR^7R^8$, and $C_{1-4}$alkyl substituted with one or where possible two or three halo substituents, preferably trifluoromethyl; $R^5$ and $R^6$ each independently represent hydrogen, $C_{1-4}$alkyl, or $C_{1-4}$alkyl substituted with phenyl; $R^7$ and $R^8$ each independently represent hydrogen or $C_{1-4}$alkyl; $R^9$ and $R^{10}$ each independently represent hydrogen, $C_{1-4}$alkyl or $C_{1-4}$alkyloxycarbonyl; L represents $C_{1-4}$alkyl; $Het^1$ represents a heterocycle selected from pyridinyl, thiophenyl, or 1,3-benzodioxolyl; $Het^2$ represents piperidinyl, pyrrolidinyl or morpholinyl; $Ar^2$ represents phenyl, naphtyl or indenyl.

13 Claims, No Drawings

U.S. PATENT DOCUMENTS 3,622,567 A    11/1971    Razdan
3,919,313 A    11/1975    Villani

FOREIGN PATENT DOCUMENTS

| DE | 2624290 A | 4/1977 |
|---|---|---|
| FR | 1399615 A | 5/1965 |
| WO | WO98/11073 A1 | 3/1998 |
| WO | WO99/26927 A2 | 6/1999 |
| WO | WO 01/90090 A1 | 11/2001 |

OTHER PUBLICATIONS

STN search report: EP 399814 (1992).*

Markownikow "Beilstein Institut zur Foerderung der Chemischen Wissenschaften, Frankfurt am Main, DE". *Chem. Ber.*, 1892, vol. 25, p. 3357, XP-002248050.

Young, C., "Beilstein Institut zur Foerderung der Chemischen Wissenschaften, Frankfurt am Main, DE". *J. Chem. Soc.*, 1898, vol. 73, p. 365, XP-002248041.

Camps: Beilstein Institut zur Foerderung der Chemischen Wissenschaften, Frankfurt am Main, DE. *Arch. Pharm.*: 1902, vol. 240; p. 358; XP002248047.

Forster, A., "Beilstein Institut zur Foerderung der Chemischen Wissenschaften Frankfurt am Main, DE". *J. Chem. Soc.* 1904, vol. 85, p. 1190, XP-002248034.

Koetz, M., "Beilstein Institut zur Foerderung der Chemischen Wissenschaften Franfurt am Main, ED". *J. Prakt. Chem.*: 1926, vol. 113, p. 74, XP-002248036.

Gryszkiewicz-T., "Beilstein Institut zur Foerderung der Chemischen Wissenschaften Frankfurt am Maln, De". *Rocz. Chem.* 1934.; vol. 14; p. 335-7; XP002248048.

Sugasawa, O. et al., "Bellstein Institut zur Foerderung der Chemishcen Wissenschaften Frankfurt am Maln, DE". 1952, vol. 72, p. 7461, XP002248038.

Giuliano, L., "Beilstein Institut zur Foerderung der Chemischen Wissenschaften Frankfurt am Main, DE" *Farmaco*, 1952, vol. 7, p. 29-32, XP002248051.

Knunjanz, G. "Beilstein Institut zur Foerderung der Chemischen Wissenschaften Frankfurt am Main, DE". *IASKA6*, 1958, p. 1219-21, XP002248040.

Takahashi, T., Synthesis of analgesics. XX. Camphane derivatives. 2"retrieved from STN". *Chem. Abst.* 1959, vol. 79, p. 162-6, vol. 79, XP002248033.

Koenig, H. et al., "Beilstein Institut zur Foerderund der Chemischen Wissenschaften Franfurt am Main, DE". *Chem. Ber.*, 1965, vol. 98, p. 3712-23, XP002248046.

Jones, et al., "Beilstein Institut zur Foerderung der Chemischen Wissenschaften Frankfurt am Main, DE", *Tetrahedron*, 1965, vol. 21, p. 2961-66, XP002279296.

Bonnekessel, J., et al., "Beilstein Institut zur Foerderung der Chemischen Wissenschaften Frankfurt am Main, DE". *Chem. Ber.* 1973, vol. 106, p. 2890-2903, XP002248049.

Mizuno, K., "Beilstein Institut zur Foerderung der Chemischen Wissenschaften Frankfurt am Main, DE". *J. Chem. Soc. Chem. Commun.*, 1975, p. 308.XP002248042.

Olsen, C. E., "Beilstein Institut zur Foerderung der Chemischen Wissenschaften Frankfurt am Main, DE". *Acta Chem. Scand. Ser B.*, 1975, p. 953-62, XP002248044.

Kuehne, M. E., et al., "Beilstein Institut zur Foerderung der Chemischen Wissenschaften Frankfurt am Main, DE". *J. Org. Chem.*, 1977, vol. 42, p. 2082-87, No. 12. XP002248045.

Olah, G. A., et al., "Beilstein Institut zur Foerderung der Chemischen Wissenschaften Frankfurt am Main, DE". *Synthesis.* 1979. p. 274-76, XP002248039.

Schroth, W. et al., "Beilstein Institut zur Foerderung der Chemischen Wissenschaften Frankfurt am Main, DE". *J. Prakt. Chem.*, 1983, vol. 325, p. 787-802, No. 5, XP002248035.

Sabri, S. S. et al., "Synthesis and antibacterial activity of some new N-(3-methyl-2- quinoxaloyl) amino alcohols and amine 1,4-dioxides". *J. Chem. Eng. Data*, 1984, p. 229-31, No. 2, XP002279298.

Yamato, M. et al., "Beilstein Institut zur Foerderung der Chemischen Wissenschaften Frankfurt am Main, DE". *Chem. Pharm. Bull.*, 1988, vol. 36, p. 3453-61, No. 9, XP002279297.

Zhou, L. et al., "Glucocorticoid effects on extracellular matrix proteins and integrins in bovine trabecular meshwork cells in relation to glaucoma". *J. J. Mole. Med.*, 1998, vol. 339, p. 341-6.

Kitagawa, O. et al., "Beilstein Institut zur Foerderung der Chemischen Wissenschaften Frankfurt am Main, DE". *Tetrahedron Lett.*, 1999, vol. 40, p. 8827-8832, No. 50, XP002279294.

Montague, C.T. et al., "Perspectives in Diabetes The Perils of Portliness Causes and Consequences of Visceral Adiposity". *Diabetes.* 2000, vol. 49, p. 883-888.

Latypov, S. et al., "Determination of the absolute stereochemistry of alcohols and amines by NMR of the group directly linked to the chiral derivatizing reagent". *Tetrahedron*, 2001, vol. 57, p. 2231-2236, No. 11, XP004230761.

Starnes, S. et al., "Beilstein Institut zur Foerderung der Chemischen Wissenschaften Frankfurt am Main, DE". *J. Amer. Chem. Soc.*, vol. 123, p. 4659-69, No. 20, XP002248037.

Masuzaki, H. et al., "A Transgenic Model of Visceral Obesity and the Metabolic Syndrome". *Science*, 2001, vol. 294, p. 2166-2170.

Rauz, S. et al., "Expression and Putative Role of 11 β-Hydrosteriod Dehydrogenase Isozymes within the Human eye". *Invest. Opht. Vis. Sc.*, 2001, vol. 42, p. 2037-2042.

Stewart. P. M., et al., "Cortisol, 11βhydroxyseroid dehydrogenase type 1 and central obesity". *T. Endoc. Meta.*, 2002, vol. 13, p. 94-96, No. 3.

Terauchi, J. et al., "Beilstein Institut zur Foerderung der Chemischen Wissenschaften Frankfurt am Main, DE". *Tetrahedron.* 2003, vol. 14, p. 587-592, No. 5, XP002279295.

PCT International Search Report dated Sep. 13, 2004 for PCT Application. No. PCT/EP03/51021 which relates to U.S. Patent Application.

Caglioti, L., et al., Beilstein Institut zur Foerderung der Chemischen Wissenschaften Frankfurt am Main, DE' *J. Org. Chem.*, 1968, vol. 33; p. 2979-81, No. 7;, XP002248043.

* cited by examiner

ADAMANTYL ACETAMIDES AS 11-BETA HYDROXYSTEROID DEHYDROGENASE INHIBITORS

CROSS REFERENCE TO RELATED APPLICATIONS

This application is the national stage of PCT Application no. PCT/EP03/51021 filed Dec. 16, 2003, which application claims priority from PCT Application No. PCT/EP02/14832 filed Dec. 23, 2002, both of which are hereby incorporated by reference.

The metabolic syndrome is a disease with increasing prevalence not only in the Western world but also in Asia and developing countries. It is characterised by obesity in particular central or visceral obesity, type 2 diabetes, hyperlipidemia, hypertension, arteriosclerosis, coronary heart diseases and eventually chronic renal failure (C. T. Montague et al. (2000), Diabetes, 49, 883-888).

Glucocorticoids and 11β-HSD1 are known to be important factors in differentiation of adipose stromal cells into mature adipocytes. In the visceral stromal cells of obese patients, 11β-HSD1 mRNA level is increased compared with subcutaneous tissue. Further, adipose tissue over-expression of 11β-HSD1 in transgenic mice is associated with increased corticosterone levels in the adipose tissue, visceral obesity, insulin sensitivity, Type 2 diabetes, hyperlipidemia and hyperphagia (H. Masuzaki et al (2001), Science, 294, 2166-2170). Therefore, 11β-HSD1 is most likely be involved in the development of visceral obesity and the metabolic syndrome.

Inhibition of 11β-HSD1 results in a decrease in differentiation and an increase in proliferation of adipose stromal cells. Moreover, glucocorticoid deficiency (adrenalectomy) enhances the ability of insulin and leptin to promote anorexia and weight loss, and this effect is reversed by glucocorticoid administration (P. M. Stewart et al (2002), Trends Endocrin. Metabol, 13, 94-96). These data suggest that enhanced reactivation of cortisone by 11β-HSD1 may exacerbate obesity and it may be beneficial to inhibit this enzyme in adipose tissue of obese patients.

Obesity is also linked to cardiovascular risks. There is a significant relationship between cortisol excretion rate and HDL cholesterol in both men and women, suggesting that glucocorticoids regulate key components of cardiovascular risk. In analogy, aortic stiffness is also associated with visceral adiposity in older adults.

Glucocorticoids and Glaucoma

Glucocorticoids increase the risk of glaucoma by raising the intraocular pressure when administered exogenously and in certain conditions of increased production like in Cushing's syndrome. Corticosteroid-induced elevation of intra ocular pressure is caused by increased resistance to aqueous outflow due to glucocorticoid induced changes in the trabecular meshwork and its intracellular matrix. Zhou et al. (Int J Mol Med (1998) 1, 339-346) also reported that corticosteroids increase the amounts of fibronectin as well as collagen type I and type IV in the trabecular meshwork of organ-cultured bovine anterior segments.

11β-HSD1 is expressed in the basal cells of the corneal epithelium and the non-pigmented epithelial cells. Glucocorticoid receptor mRNA was only detected in the trabecular meshwork, whereas in the non-pigmented epithelial cells mRNA for the glucocorticoid-, mineralocorticoid receptor and 11β-HSD1 was present. Carbenoxolone administration to patients resulted in a significant decrease in intra-ocular pressure (S. Rauz et al. (2001), Invest. Ophtalmol. Vis. Science, 42, 2037-2042), suggesting a role for HSD 1-inhibitors in treating glaucoma.

Accordingly, the underlying problem to be solved by the present invention was to identify potent 11β-HSD inhibitors, with a high selectivity for 11β-HSD1, and the use thereof in treating pathologies associated with excess cortisol formation such as obesity, diabetes, obesity related cardiovascular diseases, and glaucoma.

This invention concerns compounds of formula (I)

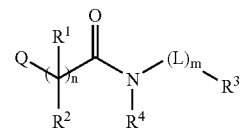

the N-oxide forms, the pharmaceutically acceptable addition salts and the stereochemically isomeric forms thereof, wherein n represents an integer being 0, 1 or 2;

m represents an integer being 0 or 1;

$R^1$ and $R^2$ each independently represents hydrogen, $C_{1-4}$alkyl, $NR^9R^{10}$, $C_{1-4}$alkyloxy, $Het^3$-O—$C_{1-4}$alkyl; or $R^1$ and $R^2$ taken together with the carbon atom with which they are attached form a carbonyl, or a $C_{3-6}$cycloalkyl; and where n is 2, either $R^1$ or $R^2$ may be absent to form an unsaturated bond;

$R^3$ represents hydrogen, $Ar^1$, $C_{1-8}$alkyl, $C_{6-12}$cycloalkyl or a monovalent radical having one of the following formulae

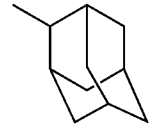
(a)

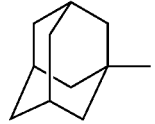
(b)

(c)

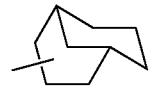
(d)

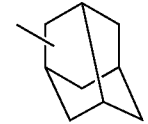
(q)

-continued (e) 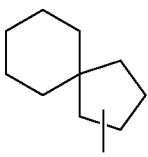

(f) 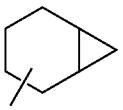

(g) 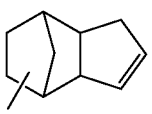

(h) 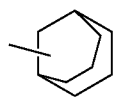

(u) 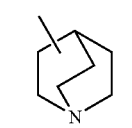

(w) 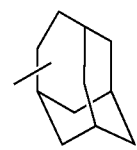

(i) 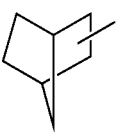

(j) 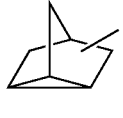

(k) 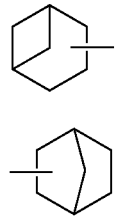

(l) 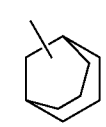

(r) 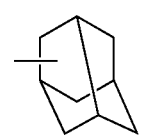

-continued (s) 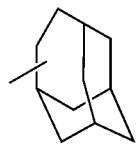

(t) 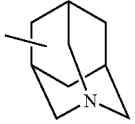

(m) 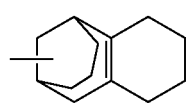

(n) 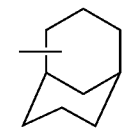

(o) 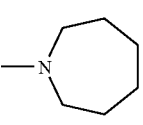

(p) 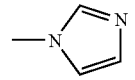

(v)

wherein said $Ar^1$, $C_{6-12}$cycloalkyl or monovalent radical may optionally be substituted with one, or where possible two or three substituents selected from the group consisting of $C_{1-4}$alkyl, $C_{1-4}$alkyloxy, phenyl, halo, oxo, carbonyl, 1,3-dioxolyl or hydroxy; in particular $R^3$ represents a monovalent radical having formula a) or b) optionally substituted with one, or where possible two or three substituents selected from the group consisting of $C_{1-4}$alkyl, $C_{1-4}$alkyloxy, phenyl, halo, oxo, carbonyl, 1,3-dioxolyl or hydroxy;

$R^4$ represents hydrogen, $C_{1-4}$alkyl, or $C_{2-4}$alkenyl;

Q represents $C_{3-8}$cycloalkyl, $Het^1$ or $Ar^2$, wherein said $C_{3-8}$cycloalkyl, $Het^1$ or $Ar^2$ are optionally substituted with one or where possible more substituents selected from halo, $C_{1-4}$alkyl, $C_{1-4}$alkyloxy, hydroxy, nitro, $Het^4$, phenyl, phenyloxy, $C_{1-4}$alkyloxycarbonyl, hydroxycarbonyl, $NR^5R^6$, $C_{1-4}$alkyloxy substituted with one or where possible two or three substituents each independently selected from $C_{1-4}$alkyl, hydroxycarbonyl, $Het^2$, $C_{1-4}$alkyl or $NR^7R^8$, $C_{2-4}$alkenyl substituted with one substituent selected from phenyl-$C_{1-4}$alkyl-oxycarbonyl, $C_{1-4}$alkyloxycarbonyl, hydroxycarbonyl or $Het^5$-carbonyl, and $C_{1-4}$alkyl substituted with one or where possible two or three substituents independently selected from halo, dimethylamine, trimethylamine, amine, cyano, $Het^6$, $Het^7$-carbonyl, $C_{1-4}$alkyloxycarbonyl or hydroxycarbonyl;

$R^5$ and $R^6$ are each independently selected from hydrogen, $C_{1-4}$alkyl, $C_{1-4}$alkyloxy$C_{1-4}$alkyl, $C_{1-4}$alkyloxycarbonyl, $C_{1-4}$alkylcarbonyl, $C_{1-4}$alkylcarbonyl substituted with one or where possible two or three substituents each independently selected from halo, $C_{1-4}$alkyl, and $C_{1-4}$alkyloxy or $R^5$ and $R^6$ each independently represent $C_{1-4}$alkyl substituted with phenyl;

$R^7$ and $R^8$ are each independently selected from hydrogen or $C_{1-4}$alkyl;

$R^9$ and $R^{10}$ are each independently selected from hydrogen, $C_{1-4}$alkyl or $C_{1-4}$alkyloxycarbonyl;

L represents $C_{1-4}$alkyl optionally substituted with one or where possible more substituents selected from $C_{1-4}$alkyl or phenyl;

$Het^1$ represents a heterocycle selected from pyridinyl, piperinidyl, pyrimidinyl, pyrazinyl, piperazinyl, pyridazinyl, indolyl, isoindolyl, indolinyl, furanyl, benzofuranyl, thiazolyl, oxazolyl, isoxazolyl, isothiazolyl, benzothiophenyl, thiophenyl, 1,8-naphthyridinyl, 1,6-naphthyridinyl, quinolinyl, 1,2,3,4-tetrahydro-quinolinyl, isoquinolinyl, 1,2,3,4-tetrahydro-isoquinolinyl, quinoxalinyl, quinazolinyl, phthalazinyl, 2H-benzopyranyl, 3,4-dihydro-2H-benzopyranyl, 2H-benzothiopyranyl, 3,4-dihydro-2H-benzothiopyranyl or 1,3-benzodioxolyl;

$Het^2$ represents a monocyclic heterocycle selected from piperidinyl, pyridinyl, pyridazinyl, pyrimidinyl, pyrazinyl, piperazinyl, 2H-pyrrolyl, pyrrolyl, 2-pyrrolinyl, 3-pyrrolinyl, pyrrolidinyl, or morpholinyl, said $Het^2$ optionally being substituted with one or where possible two or more substituents each independently selected from hydroxy, $C_{1-4}$alkyl or $C_{1-4}$alkyloxy;

$Het^3$ represents a monocyclic heterocycle selected from 2H-pyranyl, 4H-pyranyl, furanyl, tetrahydro-2H-pyranyl, pyridinyl, piperidinyl, or furanyl;

$Het^4$ represents a monocyclic heterocycle selected from pyridazinyl, pyrimidinyl, pyrrolidinyl, pyrazinyl, piperazinyl, triazolyl, tetrazolyl or morpholinyl, said $Het^4$ optionally being substituted with one or where possible two or more substituents each idependently selected from hydroxy, carbonyl, $C_{1-4}$alkyl or $C_{1-4}$alkyloxy;

$Het^5$ represents a monocyclic heterocycle selected from pyridazinyl, pyrimidinyl, pyrrolidinyl, pyrazinyl, piperazinyl or morpholinyl, said $Het^5$ optionally being substituted with one or where possible two or more substituents each independently selected from hydroxy, carbonyl, $C_{1-4}$alkyl or $C_{1-4}$alkyloxy; in particular piperazinyl or morpholinyl;

$Het^6$ represents a monocyclic heterocycle selected from pyridazinyl, pyrimidinyl, pyrrolidinyl, pyrazinyl, piperazinyl or morpholinyl, said $Het^6$ optionally being substituted with one or where possible two or more substituents each independently selected from hydroxy, carbonyl, $C_{1-4}$alkyl or $C_{1-4}$alkyloxy;

$Het^7$ represents a monocyclic heterocycle selected from pyridazinyl, pyrimidinyl, pyrrolidinyl, pyrazinyl, piperazinyl or morpholinyl, said $Het^7$ optionally being substituted with one or where possible two or more substituents each independently selected from hydroxy, carbonyl, $C_{1-4}$alkyl or $C_{1-4}$alkyloxy; in particular selected piperazinyl or morpholinyl;

$Ar^1$ represents carbocyclic radicals containing one or more rings selected from the group consisting of phenyl, biphenyl, indenyl, 2,3-dihydroindenyl, fluorenyl, 5,6,7,8-tetrahydronaphtyl or naphthyl $Ar^2$ represents carbocyclic radicals containing one or more rings selected from the group consisting of phenyl, biphenyl, benzocyclobutenyl, benzocycloheptanyl, benzosuberenyl, indenyl, 2,3-dihydroindenyl, fluorenyl, 1,2-dihydronaphthyl, 5,6,7,8-tetrahydronaphthyl or naphthyl.

As used in the foregoing definitions and hereinafter, halo is generic to fluoro, chloro, bromo and iodo; $C_{1-4}$alkyl defines straight and branched chain saturated hydrocarbon radicals having from 1 to 4 carbon atoms such as, for example, methyl, ethyl, propyl, butyl, 1-methylethyl, 2-methylpropyl, 2,2-dimethylethyl and the like; $C_{1-8}$alkyl defines straight and branched chain saturated hydrocarbon radicals having from 1 to 8 carbon atoms such as the groups defined for $C_{(1-4)}$alkyl and pentyl, hexyl, octyl, 2-methylbutyl 2-methylpentyl, 2,2-dimethylpentyl and the like; $C_{3-6}$cycloalkyl is generic to cyclopropyl, cyclobutyl, cyclopentyl and cyclohexyl; $C_{6-12}$cycloalkyl is generic to cycloheptyl and cyclooctanyl, cyclononane, cyclodecane, cycloundecane and cyclododecane; $C_{1-4}$alkyloxy defines straight or branched saturated hydrocarbon radicals such as methoxy, ethoxy, propyloxy, butyloxy, 1-methylethyloxy, 2-methylpropyloxy and the like.

As used herein before, the terms oxo or carbonyl refers to (=O) that forms a carbonyl moiety with the carbon atom to which it is attached.

The pharmaceutically acceptable addition salts as mentioned hereinabove are meant to comprise the therapeutically active non-toxic acid addition salt forms, which the compounds of formula (I), are able to form. The latter can conveniently be obtained by treating the base form with such appropriate acid. Appropriate acids comprise, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

The pharmaceutically acceptable addition salts as mentioned hereinabove are meant to comprise the therapeutically active non-toxic base addition salt forms which the compounds of formula (I), are able to form. Examples of such base addition salt forms are, for example, the sodium, potassium, calcium salts, and also the salts with pharmaceutically acceptable amines such as, for example, ammonia, alkylamines, benzathine, N-methyl-D-glucamine, hydrabamine, amino acids, e.g. arginine, lysine.

Conversely said salt forms can be converted by treatment with an appropriate base or acid into the free acid or base form.

The term addition salt as used hereinabove also comprises the solvates which the compounds of formula (I), as well as the salts thereof, are able to form. Such solvates are for example hydrates, alcoholates and the like.

The term stereochemically isomeric forms as used hereinbefore defines the possible different isomeric as well as conformational forms which the compounds of formula (I), may possess. Unless otherwise mentioned or indicated, the chemical designation of compounds denotes the mixture of all possible stereochemically and conformationally isomeric forms, said mixtures containing all diastereomers, enantiomers and/or conformers of the basic molecular structure. All stereochemically isomeric forms of the compounds of formula (I), both in pure form or in admixture with each other are intended to be embraced within the scope of the present invention.

The N-oxide forms of the compounds of formula (I), are meant to comprise those compounds of formula (I) wherein one or several nitrogen atoms are oxidized to the so-called N-oxide.

An interesting group of compounds consists of those compounds of formula (I) wherein one or more of the following restrictions apply:

(i) n represents an integer being 1 or 2 provided that when n represents 2, Q represents $Het^1$ or $Ar^2$, wherein said $Het^1$ or $Ar^2$ are optionally substituted with one or where possible more substituents selected from halo, $C_{1-4}$alkyl, $C_{1-4}$alkyloxy, hydroxy, nitro, Het$^4$, phenyl, phenyloxy, hydroxycarbonyl, NR$^5$R$^6$, $C_{1-4}$alkyloxy substituted with one or where possible two or three substituents each independently selected from hydroxycarbonyl, Het$^2$ and NR$^7$R$^8$, and $C_{1-4}$alkyl substituted with one or where possible two or three halo substituents;

(ii) R$^1$ and R$^2$ each independently represents hydrogen, $C_{1-4}$alkyl, NR$^9$R$^{10}$, $C_{1-4}$alkyloxy, Het$^3$-O-$C_{1-4}$alkyl; or R$^1$ and R$^2$ taken together with the carbon atom with which they are attached form a carbonyl, or a $C_{3-6}$cycloalkyl;

(iii) R$^3$ represents phenyl, $C_{6-12}$cycloalkyl or a monovalent radical having one of the following formulae

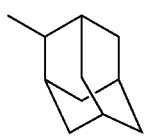 (a)

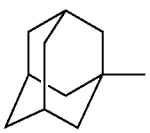 (b)

 (c)

 (d)

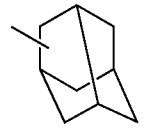 (q)

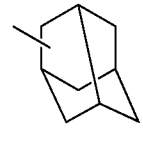 (r)

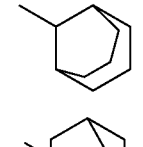 (g)

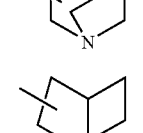 (h)

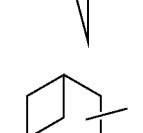 (w)

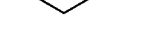 (j)

-continued

 (k)

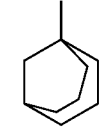 (l)

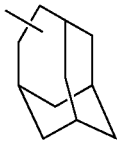 (t)

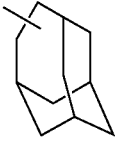 (u)

 (o)

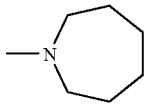 (p)

wherein said phenyl, $C_{6-12}$cycloalkyl or monovalent radical may optionally be substituted with one, or where possible two or three substituents selected from the group consisting of $C_{1-4}$alkyl, $C_{1-4}$alkyloxy, halo, carbonyl, phenyl or hydroxy; in particular R$^3$ represents a monovalent radical having formula a) or b) optionally substituted with one, or where possible two or three substituents selected from the group consisting of $C_{1-4}$alkyl, $C_{1-4}$alkyloxy, halo, carbonyl, phenyl or hydroxy;

(iv) R$^4$ represents hydrogen or $C_{1-4}$alkyl;

(v) Q represents Het$^1$ or Ar$^2$, wherein said Het$^1$ or Ar$^2$ are optionally substituted with one or where possible more substituents selected from halo, $C_{1-4}$alkyl, $C_{1-4}$alkyloxy, hydroxy, nitro, Het$^4$, phenyl, phenyloxy, hydroxycarbonyl, NR$^5$R$^6$, $C_{1-4}$alkyloxy substituted with one or where possible two or three substituents each independently selected from $C_{1-4}$alkyl hydroxycarbonyl, Het$^2$ and NR$^7$R$^8$, and $C_{1-4}$alkyl substituted with one or where possible two or three halo substituents;

(vi) Het$^1$ represents a heterocycle selected from piperinidyl, pyrimidinyl, pyrazinyl, piperazinyl, pyridazinyl, indolyl, isoindolyl, indolinyl, benzofuranyl, benzothiophenyl, 1,8-naphthyridinyl, 1,6-naphthyridinyl, quinazolinyl, phthalazinyl, or 1,3-benzodioxolyl;

(vii) Ar$^2$ represents phenyl or naphtyl optionally substituted with $C_{1-4}$alkyl, $C_{1-4}$alkyloxy or halo; preferably substituted with methyl or methoxy.

Another interesting group of compounds consists of those compounds of formula (I) wherein one or more of the following restrictions apply:

(i) $R^1$ and $R^2$ each independently represents hydrogen $C_{1-4}$alkyl, $NR^9R^{10}$; or $R^1$ and $R^2$ taken together with the carbon atom with which they are attached form a $C_{3-6}$cycloalkyl; and where n is 2, either $R^1$ or $R^2$ may be absent to form an unsaturated bond;

(ii) $R^3$ represents a $C_{6-12}$cycloalkyl or a monovalent radical having one of the following formulae

(a)

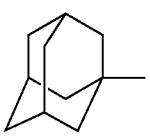
(b)

(c)

(q)

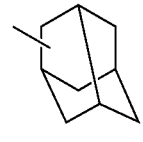
(r)

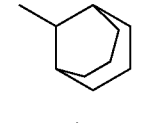
(g)

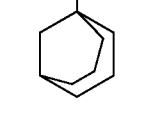
(l)

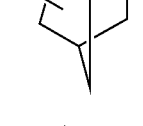
(w)

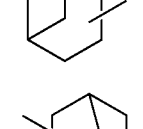
(j)

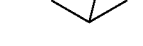
(k)

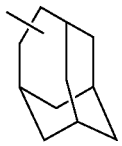
(u)

(t)

(o)

wherein said $C_{6-12}$cycloalkyl or monovalent radical may optionally be substituted with one, or where possible two, three or more substituents selected from the group consisting of $C_{1-4}$alkyl, $C_{1-4}$alkyloxy, halo, carbonyl, hydroxy, or 1,3-dioxolyl; in particular $R^3$ represents a monovalent radical having formula a) or b) optionally substituted with one, or where possible two or three substituents selected from the group consisting of $C_{1-4}$alkyl, $C_{1-4}$alkyloxy, halo, carbonyl, or hydroxy;

(iii) Q represents $Het^1$ or $Ar^2$ wherein said $Het^1$ or $Ar^2$ are optionally substituted with one or where possible two or more substituents selected from halo, $C_{1-4}$alkyl, $C_{1-4}$alkyloxy, hydroxy, $C_{1-4}$alkyloxycarbonyl, $Het^4$, $NR^5R^6$, $C_{1-4}$alkyloxy substituted with one or where possible two or three substituents each independently selected from hydroxycarbonyl, $Het^2$ and $NR^7R^8$, $C_{2-4}$alkenyl substituted with one substituent selected from phenyl-$C_{1-4}$alkyl-oxycarbonyl or $Het^5$-carbonyl and $C_{1-4}$alkyl substituted with one or where possible two or three substituents each independently selected from halo, dimethylamine, amine, cyano, $Het^6$, $Het^7$-carbonyl or hydroxycarbonyl;

(iv) $R^5$ and $R^6$ are each independently selected from hydrogen, $C_{1-4}$alkyl, $C_{1-4}$alkylcarbonyl, $C_{1-4}$alkylcarbonyl substituted with one or where possible two or three halo substituents.

(v) $R^9$ and $R^{10}$ are each independently selected from hydrogen or $C_{1-4}$alkyl;

(vi) L represents a $C_{1-4}$alkyl, preferably methyl;

(vii) $Het^1$ represents a heterocycle selected from pyridinyl, pyrimidinyl, indolyl, thiophenyl, benzothiophenyl, quinolinyl, 1,2,3,4-tetrahydro-quinolinyl, isoquinolinyl, 1,2,3,4-tetrahydro-isoquinolinyl, 2H-benzopyranyl, 3,4-dihydro-2H-benzopyranyl, 2H-benzothiopyranyl, 3,4-dihydro-2H-benzothiopyranyl or 1,3-benzodioxolyl;

(viii) $Het^2$ represents a monocyclic heterocycle selected from piperidinyl, piperazinyl, pyridinyl, pyrrolidinyl or morpholinyl, said $Het^2$ optionally being substituted with one or where possible two or more $C_{1-4}$alkyl substituents;

(ix) $Het^4$ represents tetrazolyl;

(x) $Het^5$ represents morpholinyl;

(xi) $Het^6$ represents a monocyclic heterocycle selected from pyrrolidinyl, piperazinyl or morpholinyl, said $Het^6$ optionally being substituted with one or where possible two or more hydroxy substituents, preferably with one hydroxy substituent;

(xii) Het⁷ represents a monocyclic heterocycle selected from piperazinyl or morpholinyl, preferably morpholinyl;

(xiii) Ar² represents carbocyclic radicals containing one or more rings selected from the group consisting of phenyl, benzocyclobutene, benzocycloheptanyl, benzosuberenyl, indenyl, 2,3-dihydroindenyl, 5,6,7,8-tetrahydronaphthyl or naphthyl.

A particular group of compounds of formula (I) were those compounds shown to be highly HSD1 specific. For these compounds of formula (I) one or more of the following restrictions apply:

(i) n represents an integer being 0, 1 or 2;

(ii) R¹ and R² each independently represents hydrogen, C₁₋₄alkyl, NR⁹R¹⁰; or
R¹ and R² taken together with the carbon atom with which they are attached form a C₃₋₆cycloalkyl; and where n is 2, either R¹ or R² may be absent to form an unsaturated bond;

(iii) R³ represents a C₆₋₁₂cycloalkyl, preferably cylo-octanyl or a monovalent radical having one of the following formulae

(a)

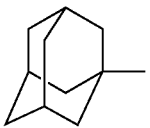
(b)

(c)

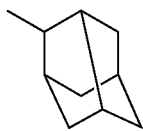
(q)

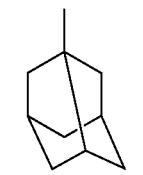
(r)

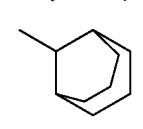
(g)

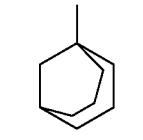
(l)

-continued

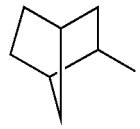
(w)

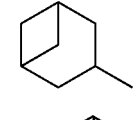
(j)

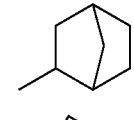
(k)

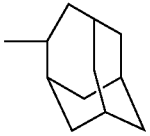
(u)

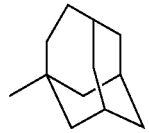
(t)

(o)

preferably having the formula (a) or (b) above, wherein said C₆₋₁₂cycloalkyl or monovalent radical may optionally be substituted with one, or where possible two, three or more substituents selected from the group consisting of C₁₋₄alkyl, C₁₋₄alkyloxy, halo or hydroxy; preferably having the formula a) above optionally substituted with C₁₋₄alkyl, C₁₋₄alkyloxy, halo or hydroxy;

(iv) Q represents Het¹ or Ar² wherein said Het¹ or Ar² are optionally substituted with one or where possible two or more substituents selected from halo, C₁₋₄alkyl, C₁₋₄alkyloxy, hydroxy, NR⁵R⁶,
C₁₋₄alkyloxy substituted with one or where possible two, three or more substituents each independently selected from hydroxycarbonyl, Het² or NR⁷R⁸, C₂₋₄alkenyl substituted with one substituent selected from phenyl-C₁₋₄ alkyl-oxycarbonyl or Het⁵-carbonyl
and C₁₋₄alkyl substituted with one or where possible two or three substituents selected from halo, Het⁶, C₁₋₄alkyloxycarbonyl or hydroxycarbonyl;

(v) R⁵ and R⁶ each independently represent hydrogen or C₁₋₄alkyl;

(vi) R⁹ and R¹⁰ each independently represent hydrogen or C₁₋₄alkyloxycarbonyl;

(vii) L represents C₁₋₄alkyl;

(viii) Het¹ represents a heterocycle selected from pyridinyl, piperidinyl, thiophenyl, 1,2,3,4-tetrahydro-quinolinyl, 1,2,3,4-tetrahydro-isoquinolinyl, 2H-benzopyranyl, 3,4-dihydro-2H-benzopyranyl, 3,4-dihydro-2H-benzothiopyranyl or 1,3-benzodioxol;

(ix) Het² represents pyridinyl, pyrrolidinyl or morpholinyl;

(x) Het⁶ represents morpholinyl;

(xi) Ar² represents phenyl, benzocyclobutene, benzocycloheptanyl, benzosuberenyl, 2,3-dihydroindenyl, 5,6,7,8-tetrahydronaphthyl, naphtyl or indenyl.

A subgroup of these highly HSD1 specific inhibitors was shown to have a superior cellular activity and consist of compounds of formulae (I) wherein one or more of the following restrictions apply (i) n represents an integer being 0, 1 or 2;

(ii) $R^1$ and $R^2$ each independently represents hydrogen, $C_{1-4}$alkyl; or
$R^1$ and $R^2$ taken together with the carbon atom with which they are attached form a $C_{3-6}$cycloalkyl; and where n is 2, either $R^1$ or $R^2$ may be absent to form an unsaturated bond;

(iii) $R^3$ represents a $C_{6-12}$cycloalkyl, preferably cylo-octanyl or a monovalent radical having one of the following formulae

(a)

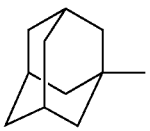
(b)

(c)

(q)

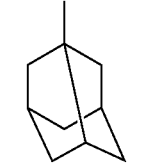
(r)

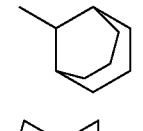
(g)

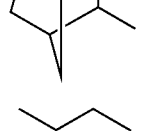
(w)

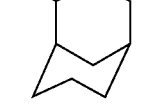
(o)

-continued

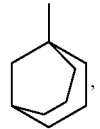
(l)

in particular having the formula (a) or (b) above, wherein said $C_{6-12}$cycloalkyl or monovalent radical may optionally be substituted with one, or where possible two, three or more substituents selected from the group consisting of $C_{1-4}$alkyl, $C_{1-4}$alkyloxy, halo or hydroxy; preferably having the formula a) above optionally substituted with $C_{1-4}$alkyl, $C_{1-4}$alkyloxy, halo or hydroxy;

(iv) Q represents Het¹ or Ar² wherein said Het¹ or Ar² are optionally substituted with one or where possible two or more substituents selected from halo, $C_{1-4}$alkyl, $C_{1-4}$alkyloxy, hydroxy, $NR^5R^6$,
$C_{1-4}$alkyloxy substituted with one or where possible two, three or more substituents each independently selected from hydroxycarbonyl, Het² and $NR^7R^8$,
$C_{2-4}$alkenyl substituted with one Het⁵-carbonyl
and $C_{1-4}$alkyl substituted with one or where possible two or three substituents selected from halo, Het⁶, $C_{1-4}$alkyloxycarbonyl or hydroxycarbonyl;

(v) $R^5$ and $R^6$ each independently represent hydrogen or $C_{1-4}$alkyl;

(vi) L represents $C_{1-4}$alkyl;

(vii) Het¹ represents a heterocycle selected from pyridinyl, piperidinyl, thiophenyl, 2H-benzopyranyl, 3,4-dihydro-2H-benzopyranyl, 3,4-dihydro-2H-benzothiopyranyl or 1,3-benzodioxol;

(viii) Het² represents pyrrolidinyl or morpholinyl;

(ix) Het⁵ represents morpholinyl;

(x) Het⁶ represents morpholinyl;

(xi) Het⁷ represents morpholinyl;

(ix) Ar² represents phenyl, benzocyclobutene, benzocycloheptanyl, benzosuberenyl, 5,6,7,8-tetrahydronaphthyl, naphtyl or indenyl.

Further interesting compounds according to the invention are those compounds of formulae (I) wherein one or more of the following restrictions apply (i) n represents an integer being 1 or 2;

(ii) $R^1$ and $R^2$ each independently represents hydrogen $C_{1-4}$alkyl, $NR^9R^{10}$, $C_{1-4}$alkyloxy; or
$R^1$ and $R^2$ taken together with the carbon atom with which they are attached form a $C_{3-6}$cycloalkyl; and where n is 2, either $R^1$ or $R^2$ may be absent to form an unsaturated bond;

(iii) $R^3$ represents a $C_{6-12}$cycloalkyl, preferably selected from cylo-octanyl and cyclohexyl or $R^3$ represents a monovalent radical having one of the following formulae

(a)

-continued (b) 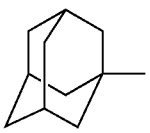

(c) 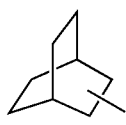

(u) 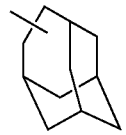

(q) 

(r) 

(g) 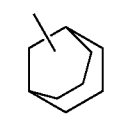

(t) 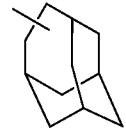

(w) 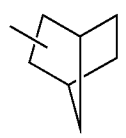

(j) 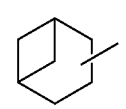

(k) 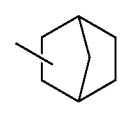

(o) 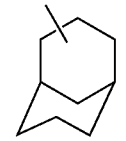

wherein said $C_{6-12}$cycloalkyl or monovalent radical may optionally be substituted with one, or where possible two, three or more substituents selected from the group consisting of $C_{1-4}$alkyl, $C_{1-4}$alkyloxy, halo or hydroxy; in particular having the formula (a) or (b) above, wherein said $C_{6-12}$cycloalkyl or monovalent radical may optionally be substituted with one, or where possible two, three or more substituents selected from the group consisting of $C_{1-4}$alkyl, $C_{1-4}$alkyloxy, halo or hydroxy; preferably having the formula a) above optionally substituted with $C_{1-4}$alkyl, $C_{1-4}$alkyloxy, halo or hydroxy;

(iv) Q represents $C_{3-8}$cycloalkyl, $Het^1$ or $Ar^2$ wherein said $C_{3-8}$cycloalkyl, $Het^1$ or $Ar^2$ are optionally substituted with one or where possible two or more substituents selected from halo, $C_{1-4}$alkyl, $C_{1-4}$alkyloxy, hydroxy, nitro, $NR^5R^6$, $C_{1-4}$alkyloxy substituted with one or where possible two, three or more substituents each independently selected from hydroxycarbonyl, $Het^2$ and $NR^7R^8$, and $C_{1-4}$alkyl substituted with one or where possible two or three halo substituents, preferably trifluoromethyl;

(v) $R^5$ and $R^6$ each independently represent hydrogen, $C_{1-4}$alkyl, or $C_{1-4}$alkyl substituted with phenyl;

(vi) L represents $C_{1-4}$alkyl;

(vii) $Het^1$ represents a heterocycle selected from pyridinyl, piperidinyl, or thiophenyl;

(viii) $Het^2$ represents piperidinyl, pyrrolidinyl or morpholinyl;

(ix) $Ar^2$ represents phenyl, naphtyl or indenyl.

A particular group of compounds of formula (I) are those where one or more of the following restrictions apply:

(i) n represents an integer being 0, 1 or 2;

(ii) $R^1$ and $R^2$ each independently represents hydrogen $C_{1-4}$alkyl, $NR^9R^{10}$, $C_{1-4}$alkyloxy; or $R^1$ and $R^2$ taken together with the carbon atom with which they are attached form a $C_{3-6}$cycloalkyl; and where n is 2, either $R^1$ or $R^2$ may be absent to form an unsaturated bond;

(iii) $R^3$ represents a $C_{6-12}$cycloalkyl, preferably selected from cylo-octanyl and cyclohexyl or $R^3$ represents a monovalent radical having one of the following formulae (a) 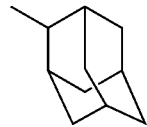

(b) 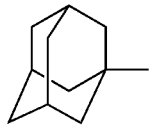

(c) 

(l) 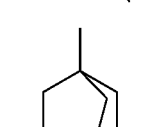

(q) 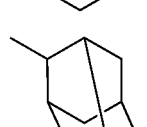

-continued

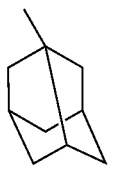 (r)

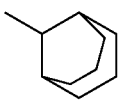 (g)

 (u)

 (o)

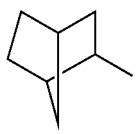 (w)

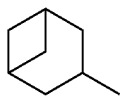 (j)

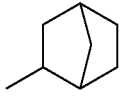 (k)

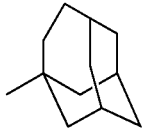 (t)

preferably having the formula (a) above, wherein said $C_{6-12}$cycloalkyl or monovalent radical may optionally be substituted with one, or where possible two, three or more substituents selected from the group consisting of $C_{1-4}$alkyl, $C_{1-4}$alkyloxy, halo or hydroxy;

(iv) $R^4$ represents hydrogen or $C_{1-4}$alkyl;

(v) Q represents $Het^1$ or $Ar^2$ wherein said $C_{3-8}$cycloalkyl, $Het^1$ or $Ar^2$ are optionally substituted with one or where possible two or more substituents selected from halo, $C_{1-4}$alkyl, $C_{1-4}$alkyloxy, hydroxy, nitro, $NR^5R^6$, $C_{1-4}$alkyloxy substituted with one or where possible two, three or more substituents each independently selected from hydroxycarbonyl, $Het^2$ or $NR^7R^8$, $C_{2-4}$alkenyl substituted with phenyl-$C_{1-4}$alkyl-oxycarbonyl and $C_{1-4}$alkyl substituted with one or where possible two or three substituents selected from, halo, $Het^6$, $Het^7$-carbonyl, $C_{1-4}$alkyloxycarbonyl or hydroxycarbonyl;

(vi) $R^5$ and $R^6$ each independently represent hydrogen, $C_{1-4}$alkyl, or $C_{1-4}$alkyl substituted with phenyl;

(vii) L represents $C_{1-4}$alkyl;

(viii) $Het^1$ represents a heterocycle selected from pyridinyl, thiophenyl, 2H-benzopyranyl, 3,4-dihydro-2H-benzopyranyl, 3,4-dihydro-2H-benzothiopyranyl or 1,3-benzodioxolyl;

(ix) $Het^2$ represents piperidinyl, pyrrolidinyl or morpholinyl;

(x) $Het^6$ represents a monocyclic heterocycle selected from piperazinyl or morpholinyl, preferably morpholinyl;

(xi) $Ar^2$ represents phenyl, benzocyclobutene, benzocycloheptanyl, benzosuberenyl, 2,3-dihydroindenyl, 1,2-dihydronaphthyl, 5,6,7,8-tetrahydronaphthyl, naphtyl or indenyl.

A preferred group of compounds consists of those compounds of formula (I) wherein one or more of the following restrictions apply:

(i) Q represents phenyl, said phenyl optionally substituted with one or two substituents selected from the halo, preferably chloro or fluor, or $C_{1-4}$alkyloxy preferably methoxy;

(ii) n is 1;

(iii) m is 0;

(iv) $R^1$ and $R^2$ represent $C_{1-4}$alkyl, preferably methyl; or $R^1$ and $R^2$ taken together with the carbon atom with which they are attached form a $C_{3-6}$cycloalkyl, preferably cyclopropyl;

(v) $R^4$ represents hydrogen;

(vi) $R^3$ represents a monovalent radical having one of the following formulae

 (a)

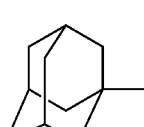 (b)

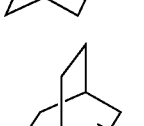 (c)

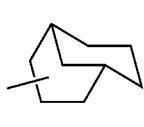 (d)

(u)

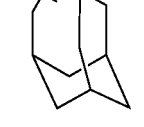 (q)

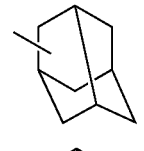 (r)

-continued

(g)

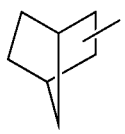
(w)

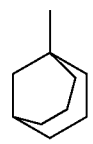
(l)

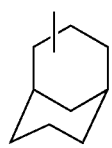
(o)

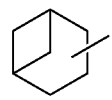
(j)

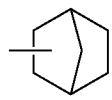
(k)

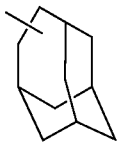
(t)

wherein said monovalent radical may optionally be substituted with one or where possible two or three substituents selected from halo, carbonyl, hydroxy or $C_{1-4}$alkyloxy, preferably methoxy, in particular $R^3$ represents a monovalent radical having the formula (a) or (b) above optionally substituted with one, or where possible two, three or more substituents selected from the group consisting of halo, carbonyl, hydroxy or $C_{1-4}$alkyloxy; preferably having the formula a) above optionally substituted with hydroxy or $C_{1-4}$alkyloxy, preferably methoxy.

Also of interest are those compounds of formula (I) wherein one ore more of the following restrictions apply;

(i) $Het^1$ represents a heterocycle selected from piperinidyl, pyrimidinyl, pyrazinyl, piperazinyl, pyridazinyl, indolyl, isoindolyl, indolinyl, benzofuranyl, benzothiophenyl, 1,8-naphthyridinyl, 1,6-naphthyridinyl, quinazolinyl, phthalazinyl, or 1,3-benzodioxolyl;

(ii) Q represents $Het^1$ or $Ar^2$ wherein said $Het^1$ or $Ar^2$ are optionally substituted with one or where possible two or more substituents selected from halo, $C_{1-4}$alkyl, $C_{1-4}$alkyloxy, hydroxy, $NR^5R^6$, $C_{1-4}$alkyloxy substituted with one or where possible two, three or more substituents each independently selected from hydroxycarbonyl, $Het^2$ and $NR^7R^8$, and $C_{1-4}$alkyl substituted with one or where possible two or three halo substituents; or Q represents phenyl, said phenyl optionally substituted with one or two substituents selected from the halo, preferably chloro or fluor, or $C_{1-4}$alkyloxy preferably methoxy;

(iii) n represents an integer being 1 or 2; or n is 1;

(iv) m is 0;

(v) $R^1$ and $R^2$ represent hydrogen $C_{1-4}$alkyl, $NR^9R^{10}$, preferably $C_{1-4}$alkyl, in particular methyl; or $R^1$ and $R^2$ taken together with the carbon atom with which they are attached form a $C_{3-6}$cycloalkyl, preferably cyclopropyl; and where n is 2, either $R^1$ or $R^2$ may be absent to form an unsaturated double bond (vi) $R^4$ represents hydrogen;

(vii) $R^3$ represents a monovalent radical having one of the following formulae

(a)

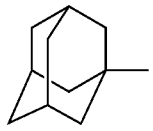
(b)

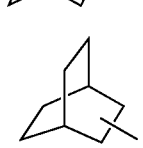
(c)

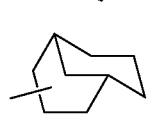
(d)

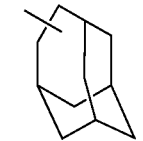
(t)

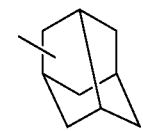
(q)

(r)

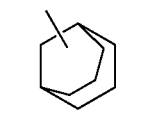
(g)

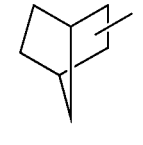
(w)

-continued

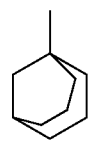 (l)

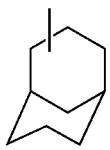 (o)

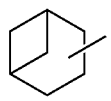 (j)

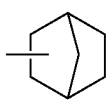 (k)

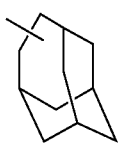 (u)

wherein said monovalent radical may optionally be substituted with one or where possible two or three substituents selected from halo, carbonyl, hydroxy or $C_{1-4}$alkyloxy, preferably methoxy; or $R^3$ represents a $C_{6-12}$cycloalkyl, preferably cylo-octanyl or a monovalent radical having one of the following formulae

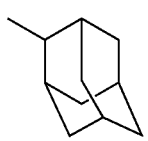 (a)

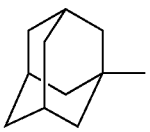 (b)

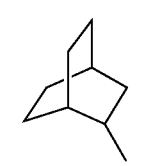 (c)

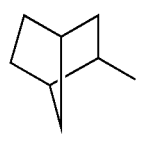 (w)

-continued

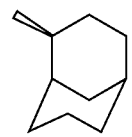 (o)

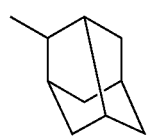 (q)

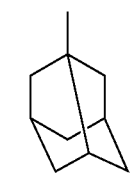 (r)

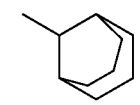 (g)

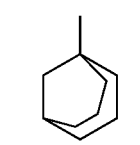 (l)

wherein said $C_{6-12}$cycloalkyl or monovalent radical may optionally be substituted with one, or where possible two, three or more substituents selected from the group consisting of $C_{1-4}$alkyl, $C_{1-4}$alkyloxy, halo or hydroxy; or $R^3$ represents a $C_{6-12}$cycloalkyl or a monovalent radical having one of the following formulae (a)

(b)

(c)

(u)

-continued (q) 

(r) 

(g) 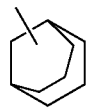

(o) 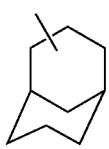

(w) 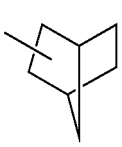

(j) 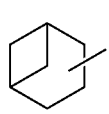

(k) 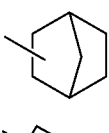

(t) 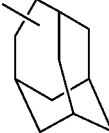

wherein said $C_{6-12}$cycloalkyl or monovalent radical may optionally be substituted with one, or where possible two, three or more substituents selected from the group consisting of $C_{1-4}$alkyl, $C_{1-4}$alkyloxy, halo or hydroxy; preferably $R^3$ represents a monovalent radical having one of the following formulae (a) 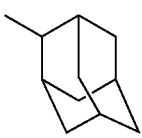

(b) 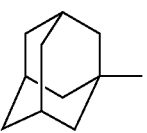

wherein said monovalent radical may optionally be substituted with one or where possible two or three substituents selected from halo, carbonyl, hydroxy or $C_{1-4}$alkyloxy, preferably a substituent selected from bromo, fluoro, chloro, hydroxy or methoxy; even more preferably those compounds wherein the $R^3$ substituent is 2-adamantyl optionally substituted with one, or where possible two or three substituents selected from the group consisting of $C_{1-4}$alkyl, $C_{1-4}$alkyloxy, halo, oxo, carbonyl or hydroxy, preferably a substituent selected from bromo, fluoro, chloro, hydroxy or methoxy;

(viii) $R^5$ and $R^6$ each independently represent hydrogen or $C_{1-4}$alkyl;

(ix) $R^9$ and $R^{10}$ each independently represent hydrogen or $C_{1-4}$alkyloxycarbonyl;

(x) L represents $C_{1-4}$alkyl;

(xi) $Het^1$ represents a heterocycle selected from pyridinyl, piperidinyl, thiophenyl or 1,3-benzodioxol;

(xii) $Het^2$ represents pyridinyl, pyrrolidinyl or morpholinyl;

(xiii) $Ar^2$ represents phenyl, naphtyl or indenyl.

A particular group of compounds are those compounds of formula (I) wherein $R^3$ is optionally substituted 2-adamantyl and wherein Q represents an optionally substituted phenyl, hereinafter referred to as the compounds of formula (I')

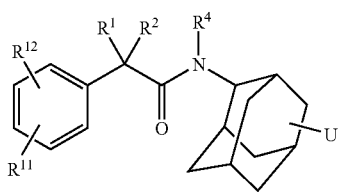

(I')

the N-oxide forms, the pharmaceutically acceptable addition salts and the stereochemically isomeric forms thereof wherein $R^1$ and $R^2$ each independently represents hydrogen, $C_{1-4}$alkyl, $NR^9R^{10}$, $C_{1-4}$alkyloxy or $Het^3$-O—$C_{1-4}$alkyl; preferably $C_{1-4}$alkyl in particular methyl; or $R^1$ and $R^2$ taken together with the carbon atom with which they are attached from a $C_{3-6}$cycloalkyl, in particular cyclopropyl or cyclobutyl;

$R^4$ represents hydrogen, $C_{1-4}$alkyl, $C_{2-4}$alkenyl;

U represents hydrogen, $C_{1-4}$alkyl, $C_{1-4}$alkyloxy, phenyl, halo, oxo, carbonyl or hydroxy $R^5$ and $R^6$ are each independently selected from hydrogen, $C_{1-4}$alkyl, $C_{1-4}$alkyloxy$C_{1-4}$alkyl, $C_{1-4}$alkyloxycarbonyl, $C_{1-4}$alkylcarbonyl, $C_{1-4}$alkylcarbonyl substituted with one or where possible two or three substituents each independently selected from halo, $C_{1-4}$alkyl, and $C_{1-4}$alkyloxy or $R^5$ and $R^6$ each independently represent $C_{1-4}$alkyl substituted with phenyl;

$R^7$ and $R^8$ are each independently selected from hydrogen or $C_{1-4}$alkyl;

$R^9$ and $R^{10}$ are each independently selected from hydrogen, $C_{1-4}$alkyl or $C_{1-4}$alkyloxycarbonyl;

$R^{11}$ and $R^{12}$ are each independently selected from hydrogen, halo, $C_{1-4}$alkyl, $C_{1-4}$alkyloxy, hydroxy, nitro, $Het^4$, phenyl, phenyloxy, $C_{1-4}$alkyloxycarbonyl, hydroxycarbonyl, $NR^5R^6$, $C_{1-4}$alkyloxy substituted with one or where possible two or three substituents each independently selected from hydroxycarbonyl, $Het^2$ and $NR^7R^8$, $C_{2-4}$alkenyl substituted with one substituent selected from phenyl-$C_{1-4}$alkyl-oxycarbonyl, $C_{1-4}$alkyloxycarbonyl, hydroxycarbonyl, Het$^5$-carbonyl, and $C_{1-4}$alkyl substituted with one or where possible two or three substituents independently selected from halo, dimethylamine, trimethylamine, amine, cyano, Het$^6$, Het$^7$-carbonyl, $C_{1-4}$alkyloxycarbonyl or hydroxycarbonyl;

Het$^1$ represents a heterocycle selected from pyridinyl, piperinidyl, pyrimidinyl, pyrazinyl, piperazinyl, pyridazinyl, indolyl, isoindolyl, indolinyl, furanyl, benzofuranyl, thiazolyl, oxazolyl, isoxazolyl, isothiazolyl, benzothiophenyl, thiophenyl, 1,8-naphthyridinyl, 1,6-naphthyridinyl, quinolinyl, isoquinolinyl, 1,2,3,4-tetrahydro-isoquinolinyl, quinoxalinyl, quinazolinyl, phthalazinyl, 2H-benzopyranyl, 3,4-dihydro-2H-benzopyranyl, 2H-benzothiopyranyl, 3,4-dihydro-2H-benzothiopyranyl or 1,3-benzodioxolyl;

Het$^2$ represents a monocyclic heterocycle selected from piperidinyl, pyridinyl, pyridazinyl, pyrimidinyl, pyrazinyl, piperazinyl, 2H-pyrrolyl, pyrrolyl, 2-pyrrolinyl, 3-pyrrolinyl, pyrrolidinyl, or morpholinyl, said Het$^2$ optionally being substituted with one or where possible two or more substituents each independently selected from hydroxy, carbonyl, $C_{1-4}$alkyl or $C_{1-4}$alkyloxy;

Het$^3$ represents a monocyclic heterocycle selected from 2H-pyranyl, 4H-pyranyl, furanyl, tetrahydro-2H-pyranyl, pyridinyl, piperidinyl, or furanyl;

Het$^4$ represents a monocyclic heterocycle selected from pyridazinyl, pyrimidinyl, pyrrolidinyl, pyrazinyl, piperazinyl, triazolyl, tetrazolyl or morpholinyl, said Het$^4$ optionally being substituted with one or where possible two or more substituents each independently selected from hydroxy, carbonyl, $C_{1-4}$alkyl or $C_{1-4}$alkyloxy;

Het$^5$ represents a monocyclic heterocycle selected from pyridazinyl, pyrimidinyl, pyrrolidinyl, pyrazinyl, piperazinyl or morpholinyl, said Het$^5$ optionally being substituted with one or where possible two or more substituents each independently selected from hydroxy, carbonyl, $C_{1-4}$alkyl or $C_{1-4}$alkyloxy; preferably piperazinyl or morpholinyl;

Het$^6$ represents a monocyclic heterocycle selected from pyridazinyl, pyrimidinyl, pyrrolidinyl, pyrazinyl, piperazinyl or morpholinyl, said Het$^6$ optionally being substituted with one or where possible two or more substituents each independently selected from hydroxy, carbonyl, $C_{1-4}$alkyl or $C_{1-4}$alkyloxy;

Het$^7$ represents a monocyclic heterocycle selected from pyridazinyl, pyrimidinyl, pyrrolidinyl, pyrazinyl, piperazinyl or morpholinyl, said Het$^7$ optionally being substituted with one or where possible two or more substituents each independently selected from hydroxy, carbonyl, $C_{1-4}$alkyl or $C_{1-4}$alkyloxy; preferably piperazinyl or morpholinyl; in particular morpholinyl.

Also of interest are those compounds of formula (I') wherein one or more of the following restrictions apply;

(i) $R^1$ and $R^2$ each independently represents hydrogen, $C_{1-4}$alkyl, $C_{1-4}$alkyloxy; preferably methyl or methoxy;

(ii) $R^4$ represents hydrogen;

(iii) U represents hydrogen, hydroxy or halo, in particular hydrogen, hydroxy, fluoro or chloro;

(iv) $R^5$ and $R^6$ are each independently selected from hydrogen, $C_{1-4}$alkyl, $C_{1-4}$alkyloxy$C_{1-4}$alkyl, $C_{1-4}$alkylcarbonyl, or $C_{1-4}$alkylcarbonyl substituted with halo;

(v) $R^7$ and $R^8$ represent $C_{1-4}$alkyl, preferably methyl;

(vi) $R^{11}$ and $R^{12}$ are each independently selected from hydrogen, $C_{1-4}$alkyl, such as in particular methyl or propyl, $C_{1-4}$alkyloxy, hydroxy, nitro, Het$^4$, NR$^5$R$^6$, $C_{1-4}$alkyloxy substituted with one or where possible two or three substituents each independently selected from hydroxycarbonyl, Het$^2$, $C_{1-4}$alkyl or NR$^7$R$^8$, $C_{2-4}$alkenyl substituted with one substituent selected from phenylC$_{1-4}$alkyloxy-carbonyl, $C_{1-4}$alkyloxycarbonyl, hydroxycarbonyl or Het$^5$-carbonyl, and $C_{1-4}$alkyl substituted with one or where possible two or three substituents independently selected from halo, dimethylamine, trimethylamine, amine, Het$^6$, Het$^7$-carbonyl or hydroxycarbonyl;

(vii) Het$^2$ represents piperidinyl, piperazinyl, pyrrolidinyl or morpholinyl, said Het$^2$ optionally being substituted with $C_{1-4}$alkyl, in particular methyl;

(viii) Het$^4$ represents tetrazolyl;

(ix) Het$^5$ represents morpholinyl;

(x) Het$^6$ represents pyridazinyl, pyrrolidinyl or morpholinyl, said Het$^4$ optionally being substituted with carbonyl or $C_{1-4}$alkyl.

Also of interest are those compounds of formula (I")

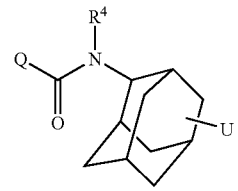

(I")

the N-oxide forms, the pharmaceutically acceptable addition salts and the stereochemically isomeric forms thereof, wherein $R^4$ represents hydrogen, $C_{1-4}$alkyl, $C_{2-4}$alkenyl;

U represents hydrogen, $C_{1-4}$alkyl, $C_{1-4}$alkyloxy, phenyl, halo, oxo, carbonyl or hydroxy Q represents Het$^1$ or Ar$^2$, wherein said Het$^1$ or Ar$^2$ are optionally substituted with one or where possible more substituents selected from halo, $C_{1-4}$alkyl, $C_{1-4}$alkyloxy, hydroxy, nitro, Het$^4$, phenyl, phenyloxy, $C_{1-4}$alkyloxycarbonyl, hydroxycarbonyl, NR$^5$R$^6$, $C_{1-4}$alkyloxy substituted with one or where possible two or three substituents each independently selected from hydroxycarbonyl, Het$^2$ and NR$^7$R$^8$, and $C_{1-4}$alkyl substituted with one or where possible two or three substituents independently selected from halo or hydroxycarbonyl;

$R^5$ and $R^6$ are each independently selected from hydrogen, $C_{1-4}$alkyl, $C_{1-4}$alkyloxy$C_{1-4}$alkyl, $C_{1-4}$alkyloxycarbonyl, $C_{1-4}$alkylcarbonyl, $C_{1-4}$alkylcarbonyl substituted with one or where possible two or three substituents each independently selected from halo, $C_{1-4}$alkyl, and $C_{1-4}$alkyloxy or $R^5$ and $R^6$ each independently represent $C_{1-4}$alkyl substituted with phenyl;

$R^7$ and $R^8$ are each independently selected from hydrogen or $C_{1-4}$alkyl;

$R^9$ and $R^{10}$ are each independently selected from hydrogen, $C_{1-4}$alkyl or $C_{1-4}$alkyloxycarbonyl;

Het$^1$ represents a bicyclic heterocycle selected from indolyl, isoindolyl, indolinyl, benzofuranyl, benzothiophenyl, 1,8-naphthyridinyl, 1,6-naphthyridinyl, quinolinyl, 1,2,3,4-tetrahydro-quinolinyl, isoquinolinyl, 1,2,3,4-tetrahydro-isoquinolinyl, quinoxalinyl, quinazolinyl, phthalazinyl, 2H-benzopyranyl, 3,4-dihydro-2H-benzopyranyl, 2H-benzothiopyranyl, 3,4-dihydro-2H-benzothiopyranyl or 1,3-benzodioxolyl;

Het² represents a monocyclic heterocycle selected from piperidinyl, pyridinyl, pyridazinyl, pyrimidinyl, pyrazinyl, piperazinyl, 2H-pyrrolyl, pyrrolyl, 2-pyrrolinyl, 3-pyrrolinyl, pyrrolidinyl, or morpholinyl, said Het² optionally being substituted with one or where possible two or more substituents each independently selected from hydroxy, $C_{1-4}$alkyl or $C_{1-4}$alkyloxy;

Het³ represents a monocyclic heterocycle selected from 2H-pyranyl, 4H-pyranyl, furanyl, tetrahydro-2H-pyranyl, pyridinyl, piperidinyl, or furanyl;

Het⁴ represents a monocyclic heterocycle selected from pyridazinyl, pyrimidinyl, pyrrolidinyl, pyrazinyl, piperazinyl or morpholinyl, said Het⁴ optionally being substituted with one or where possible two or more substituents each idependently selected from hydroxy, carbonyl, $C_{1-4}$alkyl or $C_{1-4}$alkyloxy;

Ar² represents carbocyclic radicals containing two rings selected from the group consisting of benzocyclobutene, benzocycloheptanyl, benzosurbenyl, indenyl, 2,3-dihydroindenyl, 5,6,7,8-tetrahydronaphtyl or naphthyl.

A further group of compounds are those compounds of formula (I'') wherein one or more of the following restrictions apply;

(i) U represents hydrogen, halo or hydroxy;

(ii) Q represents Het¹ or Ar², wherein said Het¹ or Ar² are optionally substituted with one or where possible two or more selected from halo, $C_{1-4}$alkyl, $C_{1-4}$alkyloxy, hydroxy, $C_{1-4}$alkyloxycarbonyl,
$C_{1-4}$alkyloxy substituted with hydroxycarbonyl, and
$C_{1-4}$alkyl substituted with hydroxycarbonyl;

(iii) Het¹ represents a bicyclic heterocycle selected from benzothiophenyl, quinolinyl, 1,2,3,4-tetrahydroquinolinyl, isoquinolinyl, 1,2,3,4-tetrahydro-isoquinolinyl, 2H-benzopyranyl, 3,4-dihydro-2H-benzopyranyl, or 2H-benzothiopyranyl;

(iv) Ar² represents benzocyclobutene, benzocycloheptanyl, benzosuberenyl, indenyl, 2,3-dihydroindenyl or 5,6,7,8-tetrahydronaphthyl.

The amide compounds of this invention can be prepared by any of several standard synthetic processes commonly used by those skilled in the art of organic chemistry and described for instance in; "Introduction to organic chemistry" Streitweiser and Heathcock—Macmillan Publishing Co., Inc.—second edition—New York—Section 24.7 (part A) p 753-756. In general, the amides can be prepared through a base-catalyzed nucleophilic addition between the appropriate carboxylic acid with the corresponding amine (scheme 1), or via a nucleophilic substitution reaction wherein the appropriate amine reacts with either the corresponding acyl halide (scheme 2), anhydride or ester, to yield the required amide.

When coupling the acids to the amines, standard chemical coupling reagents such as carbonyldiimidazole (CDI), 1.3-dicyclohexylcarbodiimide (DCC) or 1-ethyl-3-(3'-dimethylaminopropyl)carbodiimide hydrochloride (EDCl) are used in the presence or absence of hydroxybenzotrialzole (HOBt). In general, adding of the carboxylic acids of formula (III) to the amines of formula (II) under base-catalyzed reaction conditions results in the formation of the amine salt which is in equilibrium with its weak acid and base. To force the equilibrium to the formation of the amide of formula (I), a dehydrogenating agent such as carbodiimides, for example DCC and CDI are added to the reaction mixture.

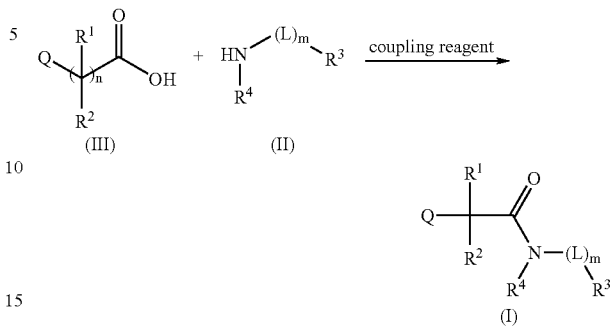

Scheme 1

In an alternative embodiment the carboxylic acids or converted into the corresponding acyl halides by reaction with, for example, thionyl chloride or oxalyl chloride. Subsequently said acyl halide (V) is added to the amine of formula (II) to yield the amide of formula (I) using art known reaction procedures such as the Schotten-Baumann method.

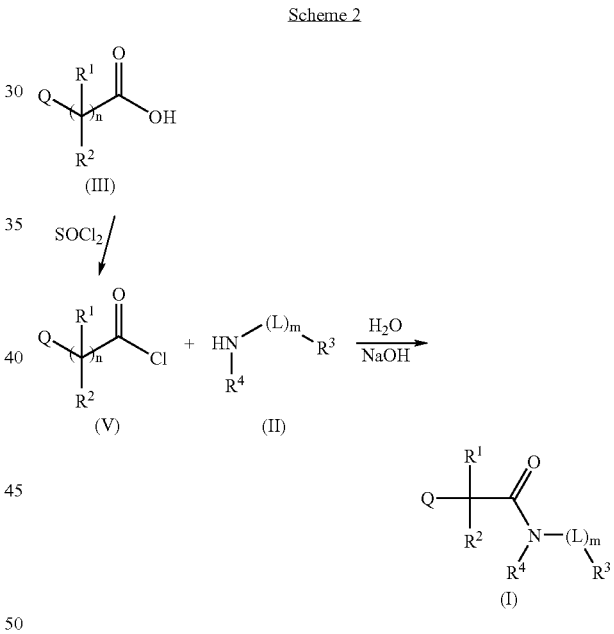

Scheme 2

The carboxylic acids of formula (III) and the amines of formula (II) are readily available, or may be prepared using methods that are well known in the art. Many compounds are commercially available, for example, from Aldrich Chemicals, or when the compounds are not commercially available, they may be readily prepared from available precursors using straightforward transformations that are well known in the art.

For example the carboxylic acids are most often prepared by hydrolysis of nitriles (scheme 3), carbonation of organometallic compounds or oxidation of primary alcohols or aldehydes, see for instance in; "Introduction to organic chemistry" Streitweiser and Heathcock—Macmillan Publishing Co., Inc.—second edition—New York—Section 19.6 p 509-511. In particular the carboxylic acids of formula (III) are prepared from the corresponding (hetero)aryl acetonitriles (VI) by conversion to the dialkyl or spiroalkyl derivative (VII) using e.g., sodium hexamethyldisilazane and methyl iodide or dibromobutane (see e.g., Trivedi et al, J. Med. Chem. 1993, 36, 3300), followed by hydrolysis under acidic or basic conditions to the desired carboxylic acid III. Appropriate acids and bases in the hydrolysis are for example $H_2SO_4$ and KOH. The hydrolysis reaction can be conveniently performed using microwave heating. Many of the nitrites of formula (VI) are commercially available, or when they are not available they may be readily prepared from available (hetero)aryl-methyl derivatives (X) under art known conditions, for example by bromination using N-bromo-succinamide (NBS) followed by substitution of bromine by CN using, for example KCN.

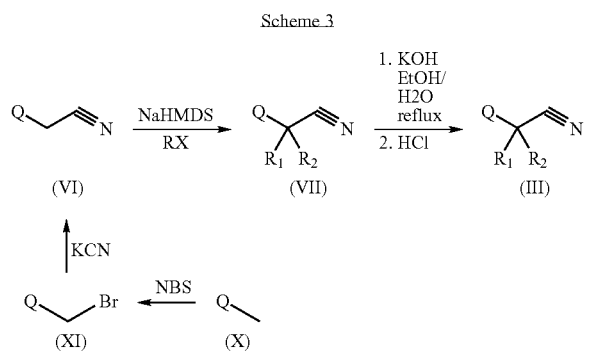

In many cases the carboxylic acids wherein Q represents a bromo-substituted aryl (III-A) were further modified according to reaction scheme 4. In a first step the bromo substituent was modified using the Heck reaction with acrylic esters, amides or acrylonitrile to obtain compounds of formula (XII). Reduction of double bond and functional groups yielded substituted amines of formula (XIV).

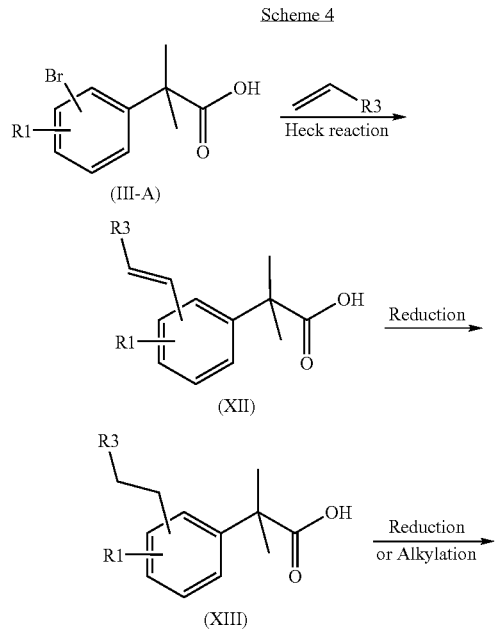

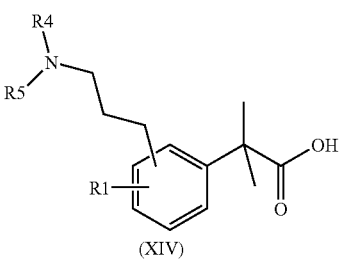

For those compounds of formula (I) where Q represents carbocyclic radicals containing two rings, the appropriate bicyclic carboxylic acids of formula (III-B) were synthesised, for example, by addition of trimethylsilylcyanide to corresponding ketones (XV) followed by acidic or basic hydrolysis of nitrile compounds (XVI) using standard conditions. Ketones, which were not available, were synthesised by intramolecular cyclisation of corresponding acids (XVIII) (see scheme 5).

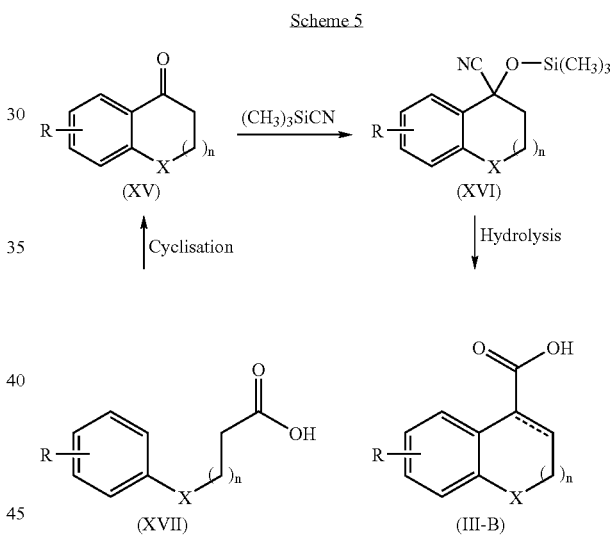

The amines of formula (II) are generally prepared using art known techniques, see for instance in; "Introduction to organic chemistry" Streitweiser and Heathcock—Macmillan Publishing Co., Inc.—second edition—New York—Section 24.6 p 742-753, and comprise synthesis through indirect alkylation of the appropriate (hetero)aryl halides in particular by the Gabriel synthesis, through reduction of the corresponding nitro or nitrille compounds, through reductive amination using for example the Eschweiler-Clarke reaction and in particular through the reduction of oximes (IX) which may be prepared from aldehydes or ketones (VIII) by reaction with hydroxylamine (scheme 6). In this latter case the oximes are reduced by lithium aluminium hydride or catalytic hydrogenation using an appropriate catalysator such as Raney Nickel, said reduction being performed in an inert anhydrous solvent such as ether or tetrahydrofuran (THF).

Scheme 6

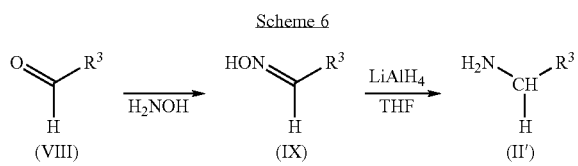

Further examples for the synthesis of compounds of formula (I) using anyone of the above mentioned synthesis methods, are provided in the experimental part hereinafter.

Where necessary or desired, any one or more of the following further steps in any order may be performed:
(i) removing any remaining protecting group(s);
(ii) converting a compound of formula (1) or a protected form thereof into a further compound of formula (I) or a protected form thereof;
(iii) converting a compound of formula (I) or a protected form thereof into a N-oxide, a salt, a quaternary amine or a solvate of a compound of formula (I) or a protected form thereof;
(iv) converting a N-oxide, a salt, a quaternary amine or a solvate of a compound of formula (I) or a protected form thereof into a compound of formula (I) or a protected form thereof;
(v) converting a N-oxide, a salt, a quaternary amine or a solvate of a compound of formula (I) or a protected form thereof into another N-oxide, a pharmaceutically acceptable addition salt a quaternary amine or a solvate of a compound of formula (I) or a protected form thereof;

(vi) where the compound of formula (I) is obtained as a mixture of (R) and (S) enantiomers resolving the mixture to obtain the desired enantiomer;

(vii) where the compounds of formula (I) wherein Q consists of bromo-substituted carbocyclic radicals containing one or two rings, various conversions are possible, see for example scheme 7 comprising;

a) alkylation using for example, alkyliodide
b) conversion to an amine using Buchwald reaction
c) arylation using Heck-reaction conditions
d) alkylation using Heck reaction conditions
e) conversion to nitrile using for example, potassiumcyanide and possible further conversion of the thus obtained nitrile to an amine that can be alkylated or acylated under art known conditions.

Scheme 7

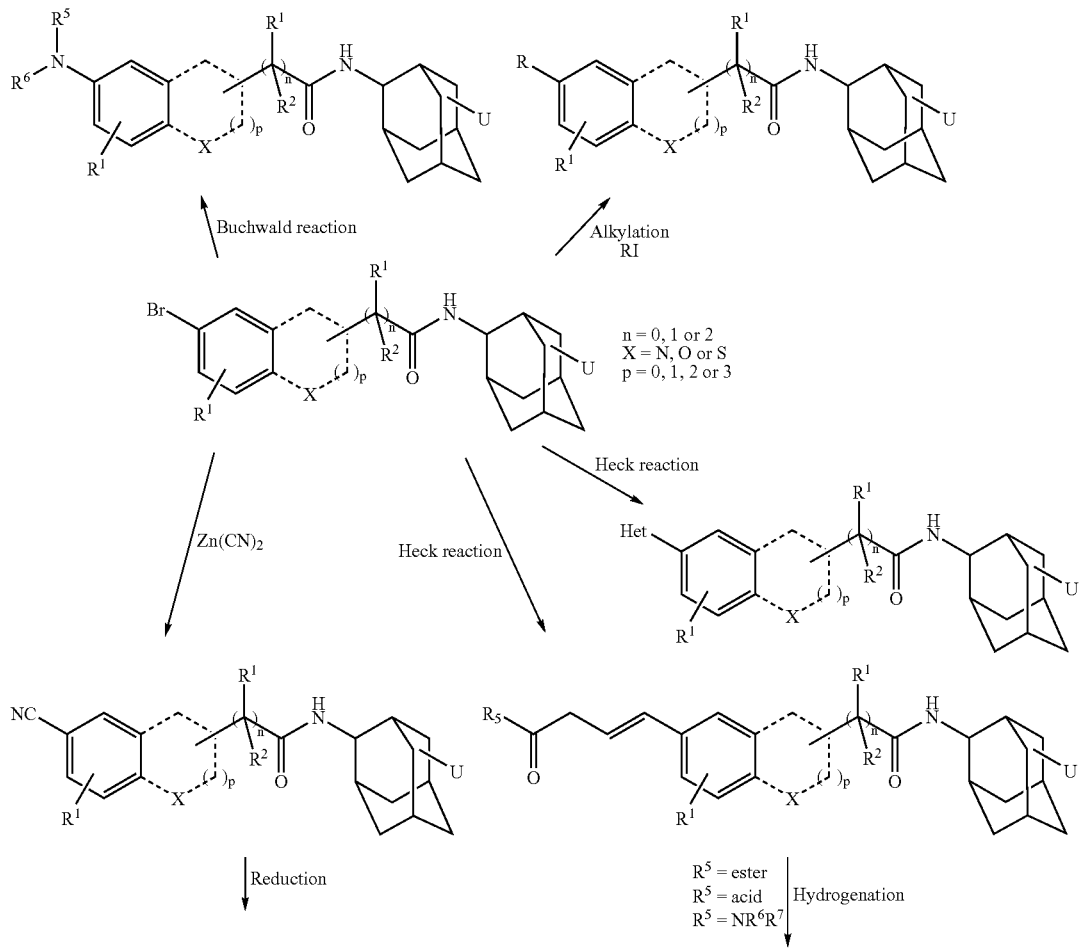

-continued

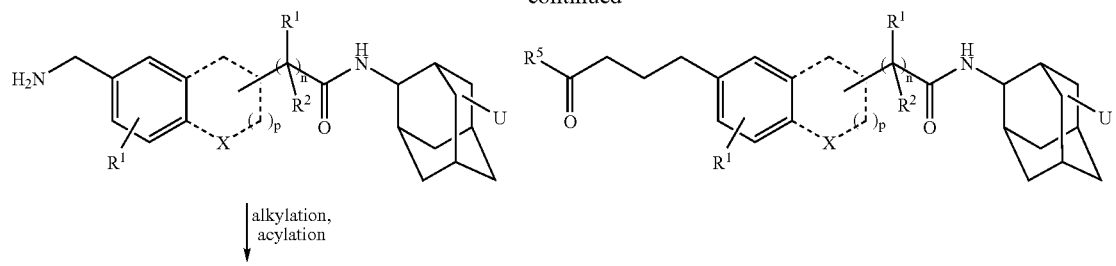

↓ alkylation, acylation

It will be appreciated by those skilled in the art that in the processes described above the functional groups of intermediate compounds may need to be blocked by protecting groups.

Functional groups which it is desirable to protect include hydroxy, amino and carboxylic acid. Suitable protecting groups for hydroxy include trialkylsilyl groups (e.g. tert-butyldimethylsilyl, tert-butyldiphenylsilyl or trimethylsilyl), benzyl and tetrahydropyranyl. Suitable protecting groups for amino include tert-butyloxycarbonyl or benzyloxycarbonyl. Suitable protecting groups for carboxylic acid include $C_{(1-6)}$alkyl or benzyl esters.

The protection and deprotection of functional groups may take place before or after a reaction step.

The use of protecting groups is fully described in 'Protective Groups in Organic Chemistry', edited by J W F McOmie, Plenum Press (1973), and 'Protective Groups in Organic Synthesis' $2^{nd}$ edition, T W Greene & P G M Wutz, Wiley Interscience (1991).

Additionally, the N-atoms in compounds of formula (I) can be methylated by art-known methods using $CH_3$—I in a suitable solvent such as, for example 2-propanone, tetrahydrofuran or dimethylformamide.

The compounds of formula (I), can also be converted into each other following art-known procedures of functional group transformation of which some examples are mentioned hereinabove.

The compounds of formula (I), may also be converted to the corresponding N-oxide forms following art-known procedures for converting a trivalent nitrogen into its N-oxide form. Said N-oxidation reaction may generally be carried out by reacting the starting material of formula (I) with 3-phenyl-2-(phenylsulfonyl)oxaziridine or with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. t-butyl hydroperoxide. Suitable solvents are, for example, water, lower alkanols, e.g. ethanol and the like, hydro-carbons, e.g. toluene, ketones, e.g. 2-butanone, halogenated hydrocarbons, e.g. dichloromethane, and mixtures of such solvents.

Pure stereochemically isomeric forms of the compounds of formula (I), may be obtained by the application of art-known procedures. Diastereomers may be separated by physical methods such as selective crystallization and chromatographic techniques, e.g. counter-current distribution, liquid chromatography and the like.

Some of the compounds of formula (I), and some of the intermediates in the present invention may contain an asymmetric carbon atom. Pure stereochemically isomeric forms of said compounds and said intermediates can be obtained by the application of art-known procedures. For example, diastereoisomers can be separated by physical methods such as selective crystallization or chromatographic techniques, e.g. counter current distribution, liquid chromatography and the like methods. Enantiomers can be obtained from racemic mixtures by first converting said racemic mixtures with suitable resolving agents such as, for example, chiral acids, to mixtures of diastereomeric salts or compounds; then physically separating said mixtures of diastereomeric salts or compounds by, for example, selective crystallization or chromatographic techniques, e.g. liquid chromatography and the like methods; and finally converting said separated diastereomeric salts or compounds into the corresponding enantiomers. Pure stereochemically isomeric forms may also be obtained from the pure stereochemically isomeric forms of the appropriate intermediates and starting materials, provided that the intervening reactions occur stereospecifically.

An alternative manner of separating the enantiomeric forms of the compounds of formula (I) and intermediates involves liquid chromatography, in particular liquid chromatography using a chiral stationary phase.

A particular group of enantiomeric intermediates for the compounds of the present invention consist of the syn and anti-isomer 1-hydroxy-4-aminoadamantane, an intermediate used in the synthesis of those compounds of formula (I) where $R^3$ represents an optionally substituted 2-adamantyl.

1-hydroxy-4-aminoadamantane is generally prepared by hydroxylation of 2-aminoadamantane, for example, using a mixture of nitric and sulphuric acid (Khimiko Farmatsevticheskii Zhurnal 1986, 20, 810; Zhurnal Organichsekoi Khimii 1976, 2369).

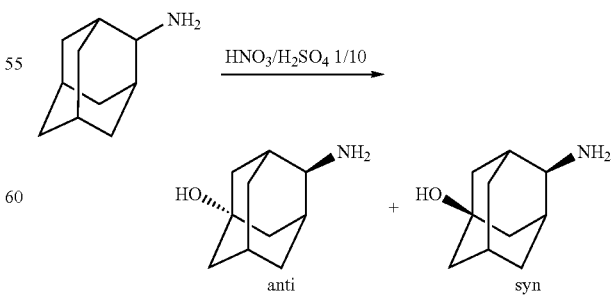

The reaction gives two stereomers of 1-hydroxy-4-aminoadamantane in ratio 3:1 to 1:1 in favour of syn-isomer. As it was found that the anti-isomers have an improved HSD1-inhibitory activity, it would be desirable to have a synthesis method that gives a better selectivity in favour of the anti-isomer.

Alternatively 1-hydroxy-4-aminoadamantane can be obtained from the corresponding ketone after reductive amination, i.e. the cyclic ketone can be converted to the amine via an imine of oxime formation and consecutive reduction of double binding. The reduction can be done using lithium aluminium hydride, Raney-nickel or noble metals like palladium, platinum, ruthenium or rhodium supported on carbon. Reductive amination using borohydrides is a one step alternative (well know method described for example in Advanced of organic chemistry from March 2003). The selectivity of the reduction depends on the structure of substrate (ketone) and the used catalyst.

Given the fact that the two isomers of 1-hydroxy-4-aminoadamantane obtained after reduction of oxime or after reductive amination with ammonia are not detectable in LCMC or GCMS, it is very difficult to separate them. The coupling reaction with an acid of formula (III) gives a mixture of two coupling products of formula (I), which are separable using chromatography. However, in order to reduce the synthesis costs and to improve the yield of the anti-isomers it would be desirable to depart from the enatiomeric pure intermediates instead.

It is a object of the present invention to provide a solution for the bove mentioned problem, consisting of a method to prepare 1-hydroxy-4-aminoadamantane said method comprising the reductive amination of 5-hydroxy-adamantan-2-one with L(-)-1-phenyl-ethylamine by catalysis using for example ruthenium supported on carbon (Scheme 8). The selectivity afforded was 3:1 in favour of anti-stereomer. The obtained isomers are easy to separate and subsequent debenzylation of anti 4-(1-Phenyl-ethylamino)-adamantan-1-ol gives pure anti-1-hydroxy-4-aminoadamatane.

In particular 1-hydroxy-4-aminoadamantane was prepared of;

a) 4-(1-Phenyl-ethylamino)-adamantan-1-ol

Preparation of

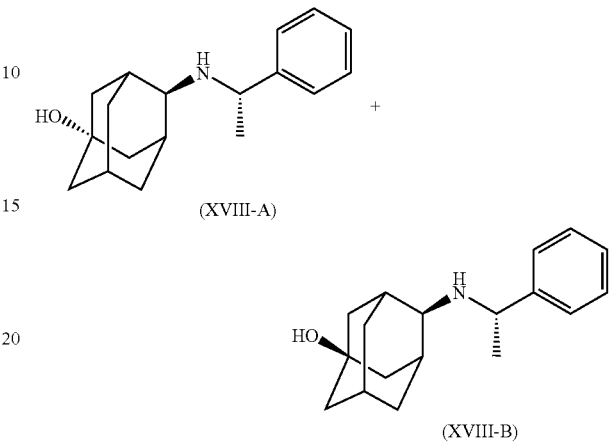

Commercially available 5-hydroxyadamantan-2-one (0.1 mol), L(-)-Alpha-methyl-benzyl amine (0.105 mol), aluminium isopropoxide (0.1 mol) and Rhodium on active carbon (20 mol %) were suspended in 500 ml of toluene, 20 ml of the 4% thiophene solution were added. The reaction mixture was stirred at 50° C. for 24 h.

The catalyst was filtered of, the filtrate was concentrated in vacuum. The residue containing two isomers in ratio 3:1 trans:cis, was purified by column chromatography to yield 12 g of the intermediate XVIII-A and 4 g of the intermediate XVIII-B.

b) 1-Hydroxy-4-aminoadamantane

Preparation of

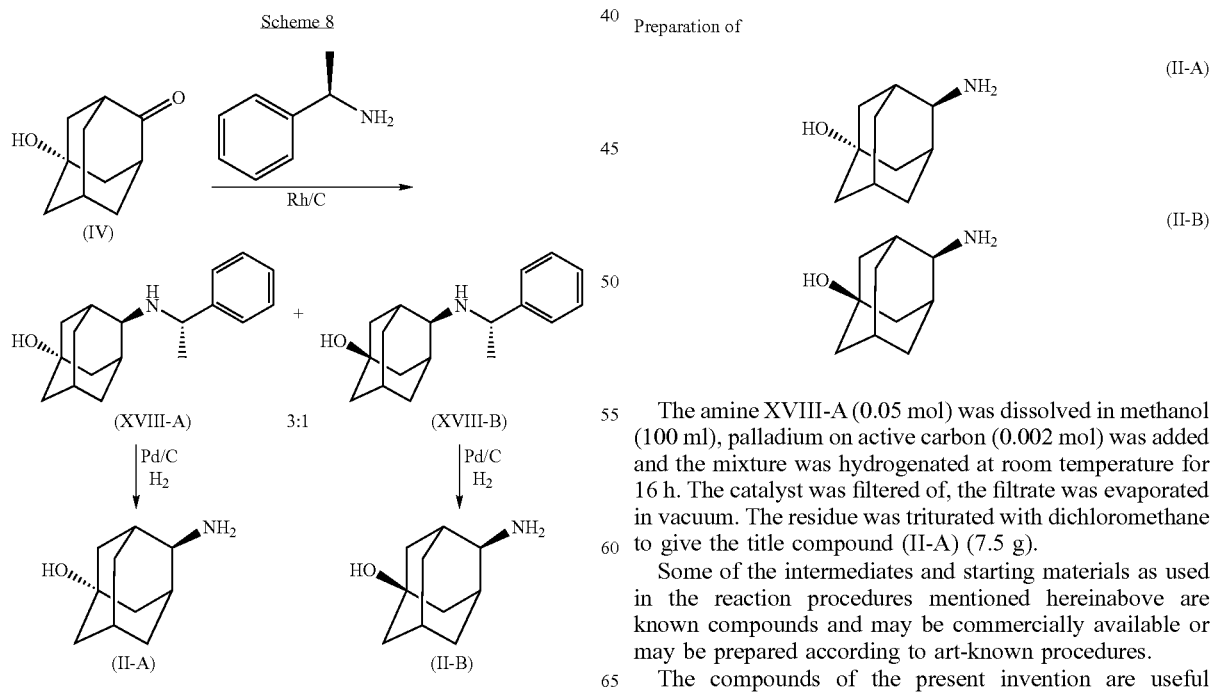

The amine XVIII-A (0.05 mol) was dissolved in methanol (100 ml), palladium on active carbon (0.002 mol) was added and the mixture was hydrogenated at room temperature for 16 h. The catalyst was filtered of, the filtrate was evaporated in vacuum. The residue was triturated with dichloromethane to give the title compound (II-A) (7.5 g).

Some of the intermediates and starting materials as used in the reaction procedures mentioned hereinabove are known compounds and may be commercially available or may be prepared according to art-known procedures.

The compounds of the present invention are useful because they possess pharmacological properties. They can therefore be used as medicines, in particular to treat pathologies associated with excess cortisol formation such as for example, obesity, diabetes, obesity related cardiovascular diseases, and glaucoma.

As described in the experimental part hereinafter, the inhibitory effect of the present compounds on the 11b-HSD1-reductase activity (conversion of cortison into cortisol) has been demonstrated in vitro, in an enzymatic assay using the recombinant 11b-HSD1 enzyme, by measuring the conversion of cortison into cortisol using HPLC purification and quantification methods. 11b-HSD1-reductase inhibition was also demonstrated in vitro, in a cell based assay comprising contacting the cells, expressing 11b-HSD1 with the compounds to be tested and assessing the effect of said compounds on the formation of cortisol in the cellular medium of these cells. The cells preferably used in an assay of the present invention are selected from the group consisting of mouse fibroblast 3T3-L1 cells, HepG2 cells, pig kidney cell, in particular LCC-PK1 cells and rat hepatocytes.

Accordingly, the present invention provides the compounds of formula (I), (I'), (I") and their pharmaceutically acceptable N-oxides, addition salts, quaternary amines and stereochemically isomeric forms for use in therapy. More particular in the treatment or prevention of cell proliferation mediated diseases. The compounds of formula (I), (I'), (I") and their pharmaceutically acceptable N-oxides, addition salts, quaternary amines and the stereochemically isomeric forms may hereinafter be referred to as compounds according to the invention.

In view of the utility of the compounds according to the invention, there is provided a method for the treatment of an animal, for example, a mammal including humans, suffering from a cell proliferative disorder such as atherosclerosis, restinosis and cancer, which comprises administering an effective amount of a compound according to the present invention.

Said method comprising the systemic or topical administration of an effective amount of a compound according to the invention, to warm-blooded animals, including humans.

It is thus an object of the present invention to provide a compound according to the present invention for use as a medicine. In particular to use the compound according to the present invention in the manufacture of a medicament for treating pathologies associated with excess cortisol formation such as for example, obesity, diabetes, obesity related cardiovascular diseases, and glaucoma.

In yet a further aspect, the present invention provides the use of the compounds according to the invention in the manufacture of a medicament for treating any of the aforementioned cell proliferative disorders or indications.

The amount of a compound according to the present invention, also referred to here as the active ingredient, which is required to achieve a therapeutical effect will be, of course, vary with the particular compound, the route of administration, the age and condition of the recipient, and the particular disorder or disease being treated. A suitable daily dose would be from 0.001 mg/kg to 500 mg/kg body weight, in particular from 0.005 mg/kg to 100 mg/kg body weight. A method of treatment may also include administering the active ingredient on a regimen of between one and four intakes per day.

While it is possible for the active ingredient to be administered alone, it is preferable to present it as a pharmaceutical composition. Accordingly, the present invention further provides a pharmaceutical composition comprising a compound according to the present invention, together with a pharmaceutically acceptable carrier or diluent. The carrier or diluent must be "acceptable" in the sense of being compatible with the other ingredients of the composition and not deleterious to the recipients thereof.

The pharmaceutical compositions of this invention may be prepared by any methods well known in the art of pharmacy, for example, using methods such as those described in Gennaro et al. Remington's Pharmaceutical Sciences (18$^{th}$ ed., Mack Publishing Company, 1990, see especially Part 8: Pharmaceutical preparations and their Manufacture). A therapeutically effective amount of the particular compound, in base form or addition salt form, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for systemic administration such as oral, percutaneous, or parenteral administration; or topical administration such as via inhalation, a nose spray, eye drops or via a cream, gel, shampoo or the like. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions: or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g., as a transdermal patch, as a spot-on or as an ointment. As appropriate compositions for topical application there may be cited all compositions usually employed for topically administering drugs e.g. creams, gellies, dressings, shampoos, tinctures, pastes, ointments, salves, powders and the like. Application of said compositions may be by aerosol, e.g. with a propellant such as nitrogen, carbon dioxide, a freon, or without a propellant such as a pump spray, drops, lotions, or a semisolid such as a thickened composition which can be applied by a swab. In particular, semisolid compositions such as salves, creams, gellies, ointments and the like will conveniently be used.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

In order to enhance the solubility and/or the stability of the compounds of formula (I), (I'), (I'') in pharmaceutical compositions, it can be advantageous to employ α-, β- or γ-cyclodextrins or their derivatives. Also co-solvents such as alcohols may improve the solubility and/or the stability of the compounds of formula (I), (I'), (I'') in pharmaceutical compositions. In the preparation of aqueous compositions, addition salts of the subject compounds are obviously more suitable due to their increased water solubility.

Experimental Part

Hereinafter, the term 'RT' means room temperature, 'THF' means tetrahydrofuran, 'AcOH' means acetic acid, 'EtOH' means ethanol, 'DME' means dimethyl ether, 'DIPE' means diisopropyl ether, 'TFA' means trifluoroacetic acid, 'EtOAc' means ethyl acetate, 'iPrOH' means isopropanol, 'HOBt' means I-hydroxy-1H-benzotriazole, 'DMA' means N,N-dimethylacetamide, 'DMF' means N,N-dimethylformamide, 'NaHMDS' means N-sodiumhexmethyldisilazane, 'DPPP' means 1,3-propanediyl-bis[diphenylphosphine], 'EDCI' means N'-(ethylcarbonimidoyl)-N,N-dimethyl-1,3-propanediamine monohydrochloride, 'DAST' means (diethylamino)sulfur trifluoride, and Extrelut™ is a product of Merck KgaA (Darmstadt, Germany) and is a short column comprising diatomaceous earth.

A. PREPARATION OF THE INTERMEDIATES

Example A1

Preparation of

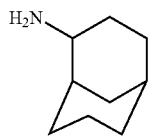

intermediate 1

Preparation of

intermediate 2

Bicyclo[3.3.1]nonan-2-one oxime [16473-10-2] (1.4 g) was dissolved in anhydrous THF (30 ml) and a solution of lithium aluminum tetrahydride (15 ml, 1 M in diethyl ether) was added. The solution was boiled under reflux for 16 hours. Addition of water (0.6 ml), 15% NaOH (0.6 ml), and water (1.8 ml), followed by filtration, drying of the filtrate (MgSO$_4$) and evaporation gave the crude amines. The residue was dissolved in dichloromethane, and extracted with 15% citric acid. The aqueous layer was basicified with 1 M KOH, and extracted with dichloromethane. The organic layer was washed with brine, dried and evaporated to give the amines 1:1 mixture (0.5 g) of intermediate (1) en intermediate (2); NMR (CDCl$_3$) δ 1.2-2.1 (m, CH), 2.45 (t, 1H), 2.9 (m, 1H).

Example A2 a) Preparation of

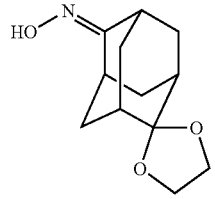

intermediate 3

Commercially available spiro[1,3-dioxolane-2,2'-tricyclo[3.3.1.1$^{3,7}$]decan]-6'-one [50776-11-9] (2.3 g, 0.012 mol) (containing about 30% of the diketal) was dissolved inethanol and a solution of hydroxylamine hydrochloride (1.7 g, 0.025 mol) and NaOH (1.0 g) in water (30 ml) was added. The mixture was stirred overnight. The volatiles were evaporated in vacuo, and the residue was extracted with dichlomethane. The organic layer was washed with brine, dried and evaporated to give the oxime intermediate (3) (2.4 g).

NMR (DMSO-d$_6$) δ 1.3-2.3 (m, CH), 2.5 (bs, 1H), 3.5 (bs, 1H), 3.95 (s, 4H, CH$_2$CH$_2$)

b) Preparation of

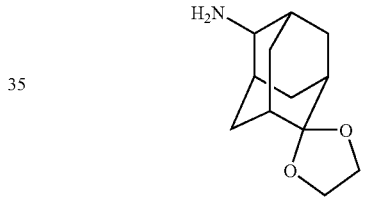

intermediate 4

6-Hydroxyimino-adamantan-2-yl ethylene ketal (2.4 g) was dissolved 7 M NH$_3$/MeOH (100 ml), Raney nickel (1 g) was added and the mixture was hydrogenated at 14° C. The mixture was filtered, and evaporated to give 2.0 g of intermediate (4).

NMR (DMSO-d$_6$) δ 1.3-2.3 (m, CH), 3.23 (bs, 2H, NH2), 3.95 (s, 4H, CH$_2$CH$_2$).

Example A3 a) Preparation of

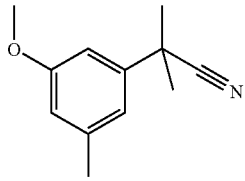

intermediate 5

A solution of 3-methoxy-5-methylbenzeneacetonitrile (0.016 mol) in THF (20 ml) was cooled to −40° C. and then NaHMDS (0.0355 mol) was added dropwise and the mixture was stirred for 1 hour at −30° C. A mixture of iodomethane (0.0355 mol) in THF (q.s.) was added dropwise at <−30° C. and the reaction mixture was stirred for 1 hour at −40° C., then the mixture was allowed to reach room temperature and stirred overnight. The resulting mixture was treated with 1N HCl and the layers were separated. The crude was extracted and treated with $CH_2Cl_2$/hexane (3/2) to isolate the desired product, yielding 2.5 g (83%) of intermediate (5).

b) Preparation of

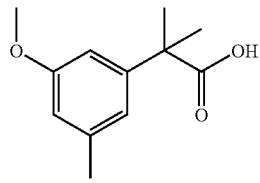

intermediate 6

Potassium hydroxide 6N in water (20 ml) was added to a solution of intermediate (5) (0.013 mol) in ethanol (40 ml) and then the reaction mixture was stirred for 4 hours under microwave conditions at 160° C. The mixture was diluted with water and extracted with DIPE. The aqueous layer was acidified with conc. HCl to pH: 1 and extracted with dichloromethane. The organic extracts were washed with water and with brine, then dried and the solvent was evaporated. The resulting residue was triturated under hexane and the desired product was collected, yielding 1.69 g (61.5%) of intermediate (6).

c) Preparation of

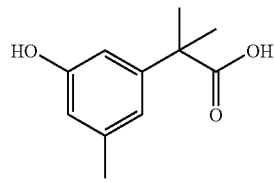

intermediate 7

A solution of intermediate (6) (0.005 mol) in dichloromethane (20 ml) was cooled to −78° C. and then tribromoborane (1 M) in dichoromethane (10.5 ml) was added dropwise. The reaction mixture was allowed to reach room temperature and was stirred overnight at room temperature. Water (50 ml) was added, followed by 6N KOH (10 ml) and the mixture was stirred for 30 minutes. The aqueous layer was separated and extracted with dichloromethane, then acidified with conc. HCl to pH: 1 and extracted with dichloromethane (3×40 ml). The organic extracts were washed with water and with brine, dried and the solvent was evaporated, yielding 0.620 g of intermediate (7).

d) Preparation of

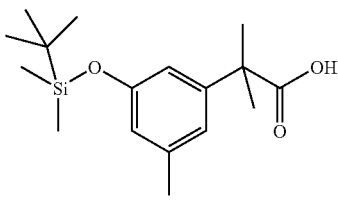

intermediate 8

Chloro(1,1-dimethylethyl)dimethylsilane (0.0048 mol), 1H-imidazole (0.0048 mol) and N,N-dimethyl-4-pyridinamine (0.020 g) were added to a solution of intermediate (7) (0.0032 mol) in dichloromethane (30 ml) and then the reaction mixture was stirred overnight at room temperature. The resulting precipitate was filtered off and the filtrate was evaporated. The residue (1.6 g) was triturated under DIPE and then the desired product was collected, yielding 0.85 g of intermediate (8).

Example A4 a) Preparation of

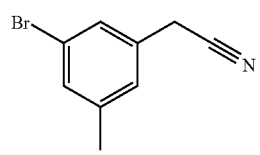

intermediate 9

A solution of potassium cyanide (0.09 mol) in water (20 ml) was added to a solution of 1-bromo-3-(bromomethyl)-5-methylbenzene [51719-69-8] (0.085 mol) in ethanol (100 ml) and the reaction mixture was stirred overnight at room temperature, then the mixture (18 g) was purified by column chromatography over silica gel (eluent:$CH_2Cl_2$/Heptane 2/1). The product fractions were collected and the solvent was evaporated, yielding 7.5 g (90%) of intermediate (9).

b) Preparation of

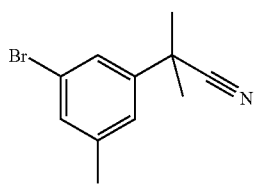

intermediate 10

A solution of intermediate (9) (0.036 mol) in THF (150 ml) was cooled to −40° C. under nitrogen, NaHMDS (2 M) in THF (0.080 mol) was added dropwise at <−25° C. and the reaction mixture was stirred for 1 hour at −30° C. A mixture of iodomethane (0.080 ml) in THF (20 ml) was added dropwise at <−30° C. and the resulting mixture was allowed to reach room temperature, then stirred overnight. HCl (1N, 100 ml) was added and the layers were separated. The aqueous layer was extracted 2 times with EtOAc, then the organic layers were combined, washed with a 5% $NaHCO_3$ soln., with water, with brine and dried. Finally, the solvent was evaporated, yielding 8.2 g of intermediate (10).

c) Preparation of

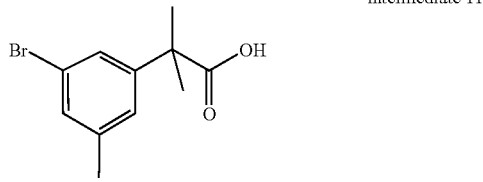

intermediate 11

A mixture of potassium hydroxide (10 g) in water (60 ml) was added to a solution of intermediate (10) (0.034 mol) in ethanol (160 ml) and then the reaction mixture was stirred and refluxed over the weekend. The mixture was diluted with ice-water and extracted with dichloromethane, to give extract (I) and aqueous layer (I). Aqueous layer (I) was acidified with HCl and extracted with dichloromethane. The extract was washed with brine, dried and the solvent was evaporated, yielding 8 g of residue (LCMS: 90% P). The residue was triturated under hexane and two product fractions were collected, yielding fraction 1:2.8 g of intermediate (11).

d) Preparation of

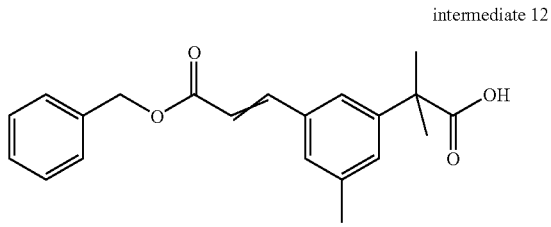

intermediate 12

N,N-diethylethanamine (0.005 mol), 2-propenoic acid, phenylmethyl ester (0.002 mol), tris(4-methylphenyl)phosphine (0.0006 mol) and then $Pd_2$(dibenzylideneacetone)$_3$ complex (0.0002 mol) were added to a solution of intermediate (11) (0.001 mol) in DMF (6 ml). The reaction mixture was heated to 90° C. and shaken for 4 hours at 90° C. The mixture was diluted with EtOAc and with DIPE, then the resulting precipitate was filtered off and the filtrate was washed 3 times with water. The aqueous layer was acidified with 1N HCl and extracted with EtOAc. The organic layer was washed with brine, dried, filtered and the solvent was evaporated, yielding 0.340 g of intermediate (12).

Example A5

Preparation of

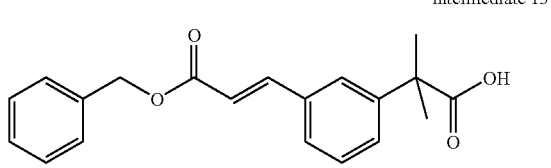

intermediate 13

3-Bromo-α,α-dimethylbenzeneacetic acid [81606-47-5] (0.001 mol) was dissolved in DMF (6 ml) and then N,N-diethylethanamine (0.005 mol) was added followed by 2-propenoic acid, phenylmethyl ester [2495-35-4] (0.002 mol). Tris(4-methylphenyl)-phosphine (0.0006 mol) and $Pd_2$(dibenzylideneacetone)$_3$ complex (0.0002 mol) were added and then the reaction mixture was shaken for 4 hours at 90° C. The mixture was diluted with EtOAc and washed with water. The aqueous layers were collected, acidified with 1N HCl to pH: 1-2 and extracted with EtOAc. The extracts were combined, washed with water and with brine, dried, filtered off and the solvent was evaporated (vac.), yielding 0.340 g of intermediate (13).

Example A6

Preparation of

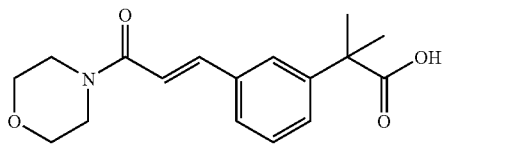

intermediate 14

3-bromo-α,α-dimethylbenzeneacetic acid [81606-47-5] (0.001 mol) was dissolved in N,N-diethylethanamine (q.s.) and the solution was degassed and then N,N-diethyl-ethanamine (0.005 mol), 4-(1-oxo-2-propenyl)morpholine [5117-12-4] (0.002 mol), tris(4-methylphenyl)phosphine (0.0005 mol) and $Pd_2$(dibenzylideneacetone)$_3$ complex (0.00015 mol) were added. The reaction mixture was shaken overnight at 90° C. and diluted with EtOAc. The catalyst was filtered off over dicalite and washed with EtOAc, then water was added and the organic layer was separated. The aqueous layer was extracted with EtOAc, acidified with HCl to pH: 1 and extracted again with EtOAc. The extracts were washed with water and with brine, dried, filtered off and the solvent was evaporated, yielding 0.291 g of intermediate (14).

Example A7 a) Preparation of

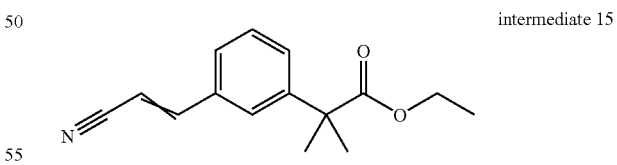

intermediate 15

A mixture of 3-bromo-α,α-dimethylbenzeneacetic acid ethyl ester [81606-46-4] (0.0018 mol), 2-propenenitrile (1 g), acetic acid, palladium (2+) salt (0.0006 mol), DPPP [6737-42-4] (0.0012 mol) and acetic acid, potassium salt (1 g) in ethanol (150 ml) was reacted for 16 hours at 100° C. and then the solvent was evaporated. The residue was dissolved in dichloromethane and the resulting solution was washed. The crude was purified by column chromatography over silica gel (eluent:$CH_2Cl_2$/Heptane 3/2). The product fractions were collected and the solvent was evaporated, yielding 0.750 g of intermediate (15).

b) Preparation of

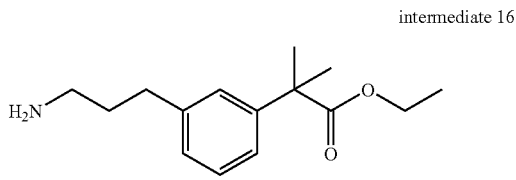

intermediate 16

Intermediate (15) (0.0031 mol) was reduced with palladium on activated carbon (cat. quant.) and then with Raney nickel (cat. quant.). After uptake of hydrogen (3 equiv.), the catalysts were filtered off and the filtrate was evaporated, yielding 0.7 g of intermediate (16).

c) Preparation of

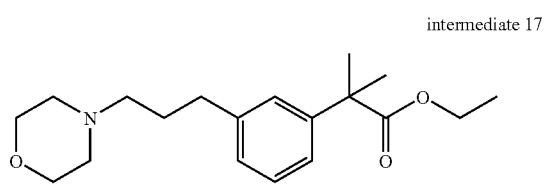

intermediate 17

1,1'-oxybis[2-chloroethane] [111-44-4] (0.0025 mol) was added to a solution of intermediate (16) (0.0012 mol) and potassium carbonate (0.006 mol) in DMF (15 ml) and then the reaction mixture was stirred for 22 hours at 100° C. The mixture was filtered and the filter residue was diluted with EtOAc, then washed with water and dried. Finally, the solvent was evaporated, yielding 0.6 g of intermediate (17).

d) Preparation of

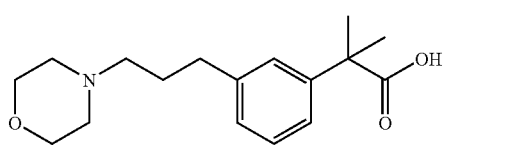

intermediate 18

Potassium hydroxide (6 ml) was added to a solution of intermediate (17) (0.0012 mol) in ethanol (12 ml) and then the reaction mixture was stirred and refluxed for 1 hour. The mixture was cooled, diluted with water and extracted with DIPE. The aqueous layer was acidified with conc. HCl and extracted with dichloromethane. The organic layer was washed with water and with brine and then the solvent was evaporated. The aqueous layer was concentrated (vac.) and the resulting concentrate was washed with methanol. Finally the solvent was evaporated, yielding 0.400 g of intermediate (18).

Example A8

Preparation of

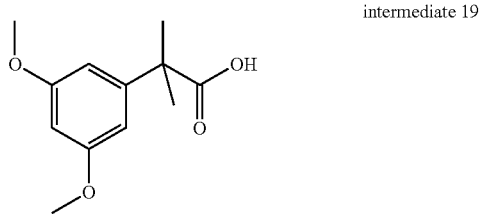

intermediate 19

Potassium hydroxide (6N) (10 ml) was added to a solution of 3,5-dimethoxy-α,α-dimethylbenzeneacetonitrile [22972-63-0] (0.011 mol) in ethanol (40 ml) and the reaction mixture was stirred and refluxed for 5 days, then the mixture was diluted with water and extracted with dichloromethane. The aqueous layer was acidified with HCl and extracted with dichloromethane. The extracts were washed with water and with brine, then dried and the solvent was evaporated, yielding 0.190 g of intermediate (19).

Example A9

Preparation of

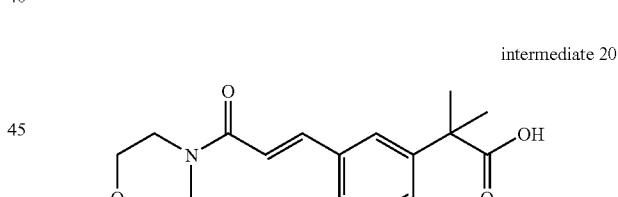

intermediate 20

N,N-diethylethanamine (0.005 mol), 4-(1-oxo-2-propenyl)morpholine [5117-12-4] (0.002 mol), tris(4-methylphenyl)phosphine [1038-95-5] (0.0006 mol) and then $Pd_2$(dibenzylideneacetone)$_3$ complex (0.00016 mol) were added to a solution of intermediate (11) (0.001 mol) in DMF (10 ml), then the reaction mixture was stirred overnight at 90° C. and diluted with EtOAc (20 ml). The resulting mixture was washed with water and then the aqueous layer was acidified with 1N HCl to pH: 1 and extracted with EtOAc. The extract was dried and the solvent was evaporated, yielding 0.500 g of residue (LCMS: 69% P). The residue was purified by column chromatography over silica gel (eluent:$CH_2Cl_2$/$CH_3OH$ 99/1). The product fractions were collected and the solvent was evaporated, yielding 0.196 g (62%) of intermediate (20).

Example A10 a) Preparation of

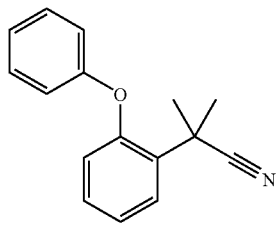

intermediate 21

2-Phenoxybenzeneacetonitrile [25562-98-5] (0.010 mol) was dissolved in THF (40 ml) under nitrogen and the mixture was cooled to −40° C., then NaHMDS (2 M) in THF (0.025 mol) was added dropwise and the mixture was stirred for 30 minutes. A mixture of iodomethane (0.030 mol) in THF, p.a. (10 ml) was added dropwise and after reaching room temperature, the reaction mixture was stirred for 2 hours. The mixture was filtered off over dicalite, then the filter residue was washed with EtOAc and 0.1 M HCl (60 ml) was added to the filtrate. The aqueous layer was separated and extracted 2 times with EtOAc. The organic layers were combined, washed with water and with brine, then dried, filtered off and the solvent was evaporated, yielding 2.7 g of intermediate (21).

b) Preparation of

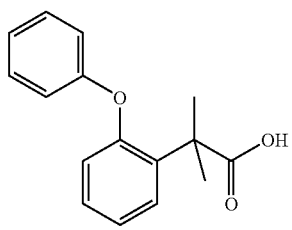

intermediate 22

A solution of intermediate (21) (0002 mol) in potassium hydroxide (6 M) in water (10 ml) and ethanol (20 ml) was put in a teflon vessel of the microwave labstation (Milestone Inc.) and the solution was stirred in the closed vessel for 6 hours at 170° C. The mixture obtained was then cooled and washed with EtOAc. The aqueous layer was separated and acidified with HCl. Finally, the resulting precipitate was filtered off, yielding intermediate (22).

Example A11 a) Preparation of

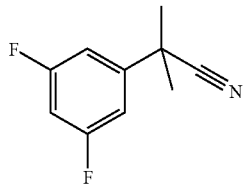

intermediate 23

3,5-Difluorobenzeneacetonitrile [122376-76-5] (0.013 mol) was dissolved in THF, p.a. (60 ml) under nitrogen and the mixture was cooled to −30° C., then NaHMDS (2 M) in THF (0.029 mol) was added dropwise and the mixture was stirred for 1 hour. A mixture of iodomethane (0.030 mol) in THF, p.a. (10 ml) was added dropwise and while reaching room temperature, the reaction mixture was stirred for 6 hours. The mixture was filtered over dicalite, then the filter residue was washed with EtOAc and the filtrate was treated with 1N HCl. The organic layer was separated, washed with water and with brine, then dried, filtered off and the solvent was evaporated, yielding 2.4 g of intermediate (23).

b) Preparation of

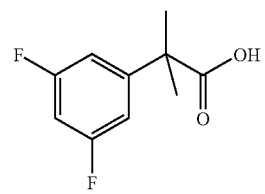

intermediate 24

A solution of intermediate (23) (0.013 mol) in potassium hydroxide (6 M) in water (20 ml) and ethanol (40 ml) was stirred and refluxed for 24 hours, after cooling the reaction mixture was washed with EtOAc. The aqueous layer was acidified with HCl and the resulting precipitate was filtered off, yielding 1.5 g (60%) of intermediate (24).

Example A12 a) Preparation of

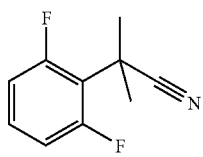

intermediate 25

2,6-Difluorobenzeneacetonitrile [654-01-3] (0.013 mol) was dissolved in THF (25 ml) under nitrogen and the mixture was cooled to −40° C., then NaHMDS (2 M) in THF (0.028 mol) was added dropwise and the mixture was stirred for 30 minutes. Iodomethane (0.028 mol) was added dropwise and while reaching room temperature, the reaction mixture was stirred for 6 hours. The mixture was filtered over dicalite, then the filter residue was washed with EtOAc and the filtrate was treated with 1N HCl. The organic layer was separated, washed with water and with brine, then dried, filtered off and the solvent was evaporated. The residue (2.2 g) was purified by column chromatography over silica gel (eluent:dichloromethane). The product fractions were collected and the solvent was evaporated, yielding 1.4 g of intermediate (25).

b) Preparation of

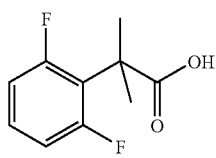

intermediate 26

Hydrochloric acid (40 ml) was added to a solution of intermediate (25) (0.006 mol) in glacial acetic acid (20 ml) and then the reaction mixture was stirred and refluxed for 24 hours. The solvent was evaporated, then the residue was dissolved in dichloromethane and washed with sodium carbonate (1 M). The aqueous layer was acidified with conc. HCl and extracted with dichloromethane. The organic extracts were collected, dried and the solvent was evaporated, yielding 0.6 g (72%) of intermediate (26).

Example A13

Preparation of

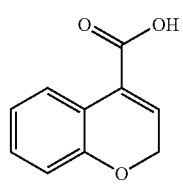

intermediate 27

Tin(II)chloride (0.068 mol) was added to 3,4-dihydro-4-[(trimethylsilyl)oxy]-2H-1-benzopyran-4-carbonitrile [74187-63-6] (0.017 mol) under nitrogen, then acetic acid (20 ml) and hydrochloric acid (20 ml) were added and the reaction mixture was stirred and refluxed overnight under nitrogen. The mixture was cooled, poured out into ice and extracted with dichloromethane. The organic layer was washed, dried, filtered and the solvent was evaporated, yielding 1.4 g of residue (54% P). The residue was purified by column chromatography over silica gel (eluent:CH$_2$Cl$_2$/CH$_3$OH 98/2). The product fractions were collected and the solvent was evaporated, yielding 1 g of intermediate (27).

Example A14 a) Preparation of

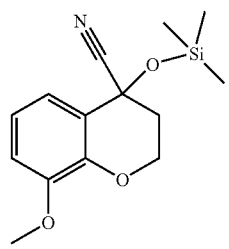

intermediate 28

A mixture of 2,3-dihydro-8-methoxy-4H-1-benzopyran-4-one [20351-79-5] (0.02 mol) and zinc iodide (0.125 g) in trichloromethane (5 ml) was stirred on ice under nitrogen. Trimethylsilanecarbonitrile [7677-24-9] (0.067 mol) was added dropwise and the reaction mixture was stirred overnight. Dichloromethane (50 ml) was added and the mixture was washed 2 times with a sodium carbonate solution. The organic layer was dried, filtered and the solvent was evaporated, yielding 4 g of intermediate (28).

b) Preparation of

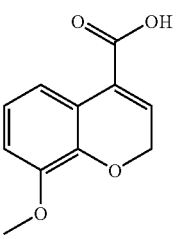

intermediate 29

A mixture of intermediate (28) (0.0072 mol) in acetic acid (15 ml) and hydrochloric acid (15 ml) was stirred and refluxed overnight under nitrogen and then the reaction mixture was cooled. The mixture was poured out into water and extracted with dichloromethane. The organic layer was extracted with a diluted sodium hydroxide solution, then the aqueous layer was acidified with hydrochloric acid and extracted with dichloromethane. The organic layer was separated, dried (MgSO$_4$), filtered off and the solvent was evaporated, yielding 1 g of residue (56% P). The residual fraction was purified by Flash-40 column chromatography over Biotage (eluent:CH$_2$Cl$_2$/CH$_3$OH 99/1). The product fractions were collected and the solvent was evaporated, yielding 0.39 g (28%) of intermediate (29).

Example A15

Preparation of

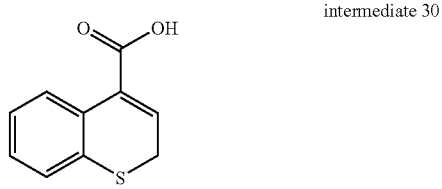

intermediate 30

A mixture of 3,4-dihydro-4-[(trimethylsilyl)oxy]-2H-1-benzothiopyran-4-carbonitrile [74187-62-5] (0.021 mol) in acetic acid (40 ml) and hydrochloric acid (40 ml) was stirred and refluxed overnight over a Dean-Starck setting. The reaction mixture was cooled and extracted with dichloromethane. The organic layer was washed with a $Na_2CO_3$ solution, then the aqueous layer was acidified with HCl to pH: 2 and extracted with dichloromethane. The organic layer was separated, washed, dried ($MgSO_4$), filtered off and the solvent was evaporated, yielding 0.7 g of intermediate (30).

Example A16 a) Preparation of

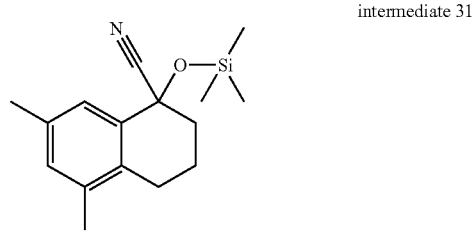

intermediate 31

A mixture of 3,4-dihydro-5,7-dimethyl-1(2H)-naphthalenone [13621-25-5] (0.02 mol) and zinc iodide (0.125 g) in trichloromethane (5 ml) was stirred on ice and trimethylsilanecarbonitrile [7677-24-9] (0.075 mol) was added. The reaction mixture was stirred overnight and washed 2 times with a $NaHCO_3$ solution. The organic layer was dried, filtered and the solvent was evaporated, yielding 5.7 g of intermediate (31).

b) Preparation of

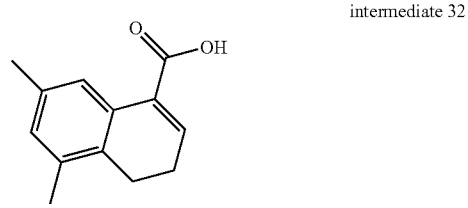

intermediate 32

A mixture of intermediate (31) (0.02 mol) in acetic acid (40 ml) and hydrochloric acid (40 ml) was stirred and refluxed for 3 days under nitrogen. The reaction mixture was cooled and extracted with dichloromethane. The organic layer was extracted with a $Na_2CO_3$ solution, then the aqueous layer was acidified with hydrochloric acid and extracted with dichloromethane. The organic layer was separated, washed, dried ($MgSO_4$), filtered off and the solvent was evaporated, yielding 1.2 g (29%) of intermediate (32).

Example A17 a) Preparation of

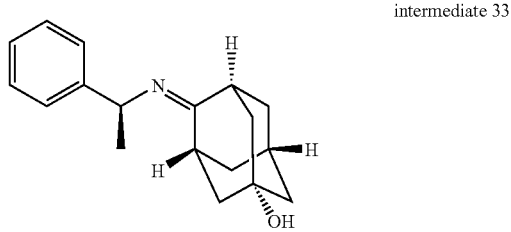

intermediate 33

A mixture of 5-hydroxytricyclo[3.3.1.13,7]decanone [20098-14-0] (0.01 mol) and (αS)-α-methylbenzenemethanamine [2627-86-3] (0.01 mol) in ethanol (20 ml) was stirred and refluxed over the weekend and then the solvent was evaporated (vacuo), yielding 2.8 g of intermediate (33).

b) Preparation of

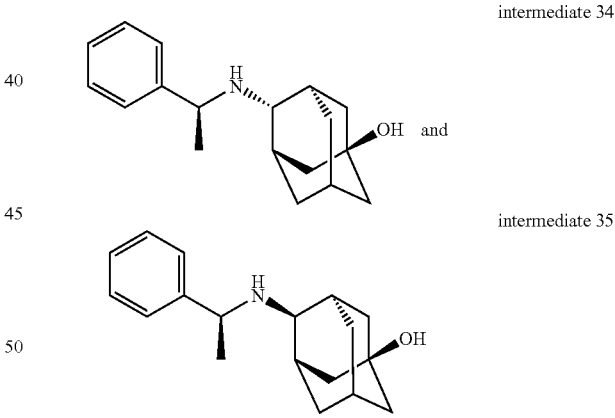

intermediate 34 and intermediate 35

Intermediate (33) (0.001 mol) was taken up in THF (anhydrous) (5 ml) and the mixture was cooled to 0° C. under nitrogen, then sodium tetrahydroborate (0.00115 mol) and trifluoroacetic acid (0.00344 mol) were added and the reaction mixture was stirred at 0° C. Dichloromethane (10 ml) and a saturated $NaHCO_3$ solution were added. The organic layer was separated, washed with $NaHCO_3$, dried and the solvent was evaporated. The residue was purified by column chromatography over silica gel (eluent:$CH_2Cl_2$/EtOAc 95/5). Two product fractions were collected and the solvent was evaporated, yielding 0.130 g of intermediate (34) and 0.090 g of intermediate (35).

Example A18

Preparation of

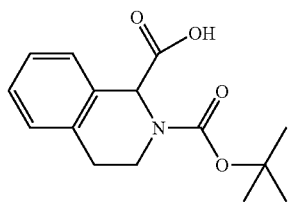

intermediate 36

A mixture of 1,2,3,4-tetrahydro-1-isoquinolinecarboxylic acid, hydrochloride [92932-74-6] (0.00117 mol) and N,N-diethylethanamine (0.2 g) in 2-propanone (10 ml) and water (10 ml) was stirred and then dicarbonic acid, bis(1,1-dimethylethyl) ester [24424-99-5] (0.0022 mol) was added. The reaction mixture was stirred over the weekend, then poured out into dichloromethane and washed with water. The organic layer was separated, dried (MgSO$_4$), filtered off and the solvent was evaporated, yielding 0.38 g of intermediate (36).

B. Preparation of the Compounds

Example B1

Preparation of

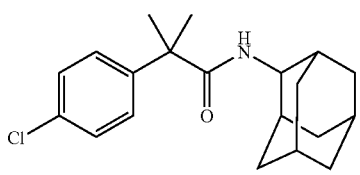

compound 1

2,2-dimethyl-(4-chlorophenyl)acetic acid [6258-30-6] (2.0 g, 10 mmol) and 2-aminoadamantane hydrochloride [13074-39-0] (1.9 g, 10 mmol) were dissolved in dichloromethane (50 ml), HOBt (2.7 g, 20 mol), N,N-diethylethanamine (2.1 g, 20 mmol), and EDCI (2.1 g, 11 mmol) were added and the mixture was stirred overnight. The reaction mixture was washed with 15% citric acid, sat. NaHCO$_3$ and brine, dried over MgSO$_4$, and evaporated in vacuo. The residue was recrystallised from isopropanol, yielding 2.0 (6 mmol, 60%) of compound 1.

NMR: (DMSO-d$_6$) δ 1.4-1.8 (m, CH), 1.47 (s, 6H, (CH3)$_2$), 3.79 (d, 1H, CH), 6.42 (d, 1H, NH), 7.38 (dd, Ar—H). LC-MS: M+1 332.89, 334.89

Example B2

Preparation of

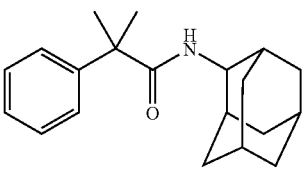

compound 2

Compound 1 (1.7 g, 5 mmol) was dissolved in methanol (100 ml), 0.5 g palladium on activated carbon (10%) and CaO (1 g) were added, and the mixture was hydrogenated at 50° C., After uptake of one equivalent of hydrogen, the reaction was filtered, evaporated till dryness. The residue was dissolved in dichloromethane, washed with sat. NaHCO$_3$, dried and evaporated. The residue was crystallized from diisopropyl ether, yielding 0.65 g (60%) of compound 2.

NMR: (DMSO-d$_6$) δ 1.4-1.8 (m, CH), 1.49 (s, 6H, (CH3)$_2$), 3.79 (d, 1H, CH), 6.21 (d, 1H, NH), 7.25-7.37 (m, 5H, Ar—H). LC-MS: M+1 298.44

Example B3

Preparation of

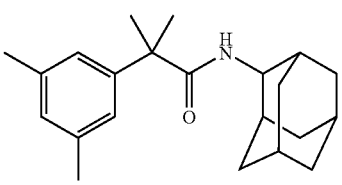

compound 3

2,2-Dimethylphenyl acetic acid [826-55-1] was dissolved in dry dichloromethane, oxalyl chloride was added and one drop of DMF. After stirring for two hours, the solution was evaporated till dryness, redissolved in 10 ml dichloromethane, and added to a solution of 2-aminoadamantane [13074-39-0] and triethylamine in Dichloromethane. The mixture was stirred overnight, extracted with 15% citric acid, sat. NAHCO$_3$ and brine, dried over MgSO$_4$, and evaporated in vacuo. The residue was recrystallised from isopropyl ether.

NMR: (CDCl$_3$) δ 1.3-1.8 (m, CH), 1.55 (s, 6H, (CH3)$_2$), 2.31 (s, 6H, 2×CH3), 3.96 (d, 1H, CH), 5.50 (d, 1H, NH), 6.91 (s, 1H, Ar—H), 6.99 (s, 2H, ArH).

Example B4 a) Preparation of

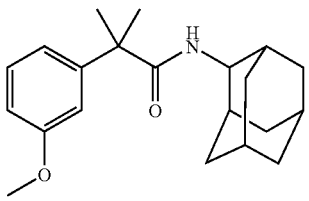
compound 4

2-Methyl-2-(3-methoxyphenyl)propionic acid (2.0 g, 10 mmol) and 2-amino-adamantane hydrochloride [13074-39-0] (1.9 g, 10 mmol) were dissolved in dichloromethane (50 ml), HOBt (2.7 g, 20 mol), N,N-diethylethanamine (2.1 g, 20 mmol), and EDCI (2.1 g, 11 mmol) were added and the mixture was stirred overnight. The reaction mixture was washed with 15% citric acid, sat. NaHCO$_3$ and brine, dried over MgSO$_4$, and evaporated in vacuo. The residue was recrystallised from isopropanol, yielding 2.0 g (6 mmol, 60%) of compound 4.

NMR: (DMSO-d$_6$) δ 1.4-1.8 (m, CH), 1.48 (s, 6H, (CH3)$_2$), 3.75 (s, 3H, OCH 3), 3.79 (d, 1H, CH), 6.23 (d, 1H, NH), 6.8-7.3 (m, 3H, Ar—H).

b) Preparation of

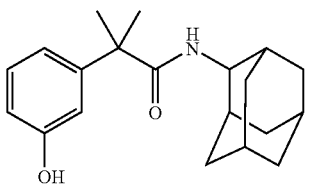
compound 5

Compound 4 was dissolved in dry dichloromethane, cooled to −78° C. and boron tribromide was added. The reaction mixture was stirred at room temperature for 1 hour, poured onto aqueous ammonia and extracted with dichloromethane. The organic layers were washed with brine, dried and evaporated. The solid residue was crystallized from ethyl acetate, yielding compound 5.

NMR: (DMSO-d$_6$) δ 1.4-1.8 (m, CH), 1.44 (s, 6H, (CH3)$_2$), 3.79 (d, 1H, CH), 6.18 (d, 1H, NH), 6.65-7.16 (dd, 4H, Ar—H), 9.35 (s, 1H, OH).

c) Preparation of

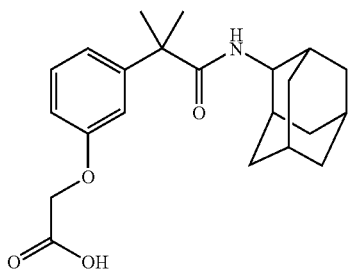
compound 6

Compound 4 was dissolved in DMF and ethyl bromoacetate was added together with potassium carbonate. The mixture was stirred at 60° C. overnight, poured on ice, and extracted with dichloromethane. The organic layer was washed with 1 M NaHCO$_3$, and brine, and evaporated. The residue was dissoled in ethanol, 1 M potassium hydroxide was added, and the mixture was stirred for 2 hours. The solution was acidified with 1 M HCl, extracted with EtOAc, the organic layer was dried and evaporated. The residue was crystallized from ethyl acetate, yielding compound 6

NMR: (DMSO-d$_6$) δ 1.4-1.8 (m, CH), 1.47 (s, 6H, (CH3)$_2$), 3.78 (d, 1H, CH), 4.67 (s, 2H, CH2COOH), 6.23 (d, 1H, NH), 6.77-7.3 (m, 4H, Ar—H).

Example B5

Preparation of

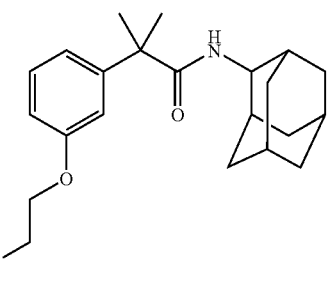
compound 7

Compound 4 was dissolved in DMF, and dimethylaminoethyl chloride hydrochloride was added, followed by K$_2$CO$_3$. The mixture was stirred at 60° C. overnight, poured on ice, and extracted with dichloromethane. The organic layer was washed with 1 M NaHCO$_3$, and brine, and evaporated. The residue was dissolved in iPrOH with heating, oxalic acid was added, and the crystallie amine was filtered, yielding compound 7

NMR: (DMSO-d$_6$) δ 1.4-1.8 (m, CH), 1.49 (s, 6H, (CH3)$_2$), 2.78 (s, 6H, N(CH3)$_2$), 3.43 (t, 2H, CH2), 3.79 (d, 1H, CH), 4.27 (t, 2H, CH2), 6.29 (d, 1H, NH), 6.85-7.35 (m, 4H, Ar—H).

Example B6

Preparation of

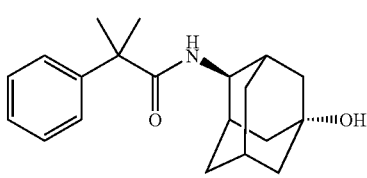
compound 8

-continued

Preparation of compound 9

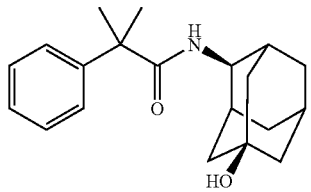

α,α-2,2-Dimethylphenyl acetic acid [826-55-1] (2.5 g, 15 mmol) was dissolved in dry dichloromethane (50 ml), oxalyl chloride (1.5 ml, 0.017 mol) was added and one drop of DMF. After stirring for two hours, the solution was evaporated till dryness, redissolved in 50 ml of dichloromethane, and added to a solution of 2-amino-adamantane (CAS 13074-39-0) (2.5 g, 15 mmol) and N,N-diethylethanamine (3.0 g, 30 mmol) in dichloromethane (50 mL). The mixture was stirred overnight, extracted with 15% citric acid, sat. NaHCO$_3$ and brine, dried over MgSO$_4$, and evaporated in vacuo. The residue was chromatographed over silicagel (eluens 3-5% MeOH in dichloro-methane), yielding 1.8 g of compound 8

NMR: (CDCl$_3$) δ 1.2-1.85 (m, CH), 1.59 (s, 6H, (CH$_3$)$_2$), 1.95-2.00 (m, 2H, CH), 3.91 (dt, 1H, CH), 5.32 (d, 1H, NH), 7.25-7.47 (m, 5H, Ar—H).

and 1.8 g of compound 9

NMR: (CDCl$_3$) δ 1.2-1.7 (m, CH), 1.56 (s, 6H, (CH$_3$)$_2$), 2.05-2.10 (m, 2H, CH), 3.83 (dt, 1H, CH), 5.32 (d, 1H, NH), 7.25-7.50 (m, 5H, Ar—H).

Example B7

Preparation of compound 10

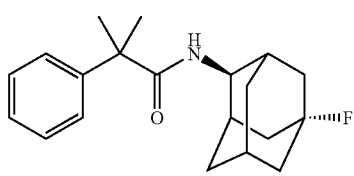

Compound 8 (80 mg) was dissolved in dichloromethane (2 ml) and cooled to −78° C. under nitrogen. DAST (0.1 ml) was added, and the mixture was stirred and warmed to room temperature. Saturated NaHCO$_3$ was added and the layers were separated. The organic layer was washed with brine, dried (MgSO$_4$) and evaporated. The residue was crystallized from diisopropylether to give 40 mg (50%) of the compound 10

NMR: (CDCl$_3$) δ 1.2-1.85 (m, CH), 1.59 (s, 6H, (CH3)$_2$), 1.95-2.10 (m, 2H, CH), 3.93 (dt, 1H, CH), 5.27 (d, 1H, NH), 7.27-7.43 (m, 5H, Ar—H).

Example B8

Preparation of compound 11

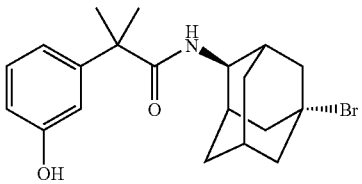

Compound 8 (100 mg, 0.3 mmol) was dissolved in dichloromethane (2 ml), cooled to −78° C. and boron tribromide (0.15 ml, 1.5 mmol) was added. The reaction mixture was warmed to room temperature, diluted with dichloromethane and poured on a mixture ice and conc. ammonia. The layers were separated, the organic layer washed with brine, dried (MgSO$_4$) and evaporated. The residue was crystallized from ethyl acetate, yielding compound 11; LC-MS: M+1 393.34, 395.34;

NMR: (CDCl$_3$) δ 1.25-1.52 (m, CH), 1.57 (s, 6H, (CH3)$_2$), 1.90-2.42 (m, CH), 3.97 (dt, 1H, CH), 5.37 (d, 1H, NH), 6.28-7.30 (m, 4H, Ar—H).

Example B9

Preparation of compound 12

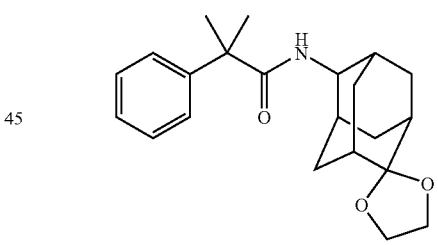

2,2-Dimethylphenyl acetic acid [826-55-1] (0.5 g, 2.7 mmol) was dissolved in dry dichloromethane, oxalyl chloride (0.4 g) was added and one drop of DMF. After stirring for two hours, the solution was evaporated till dryness, redissolved in 10 ml dichloromethane, and added to a solution of 6-oxo-adamantan-2-ylamine ethylene ketal (0.6 g, 2.7 mmol) and N,N-diethylethanamine (0.5 ml) in dichloromethane. The mixture was stirred overnight, extracted with 15% citric acid, sat. NAHCO$_3$ and brine, dried over MgSO$_4$, and evaporated in vacuo. The residue was purified over silicagel (eluens 5% MeOH in dichloromethane), and compound 12 was recrystallised from isopropyl ether, yielding 600 mg (50%).

NMR: (CDCl$_3$) δ 1.52-2.05 (m, CH), 1.60 (s, 6H, (CH3)$_2$), 3.85 (dt, 1H, CH), 3.85-3.90 (m, 4H, CH2CH2), 5.45 (d, 1H, NH), 7.23-7.42 (m, 5H, Ar—H).

Example B10

Preparation of

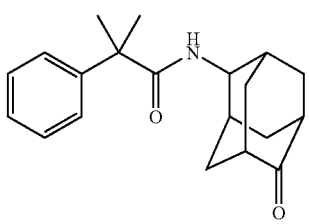

compound 13

The ketal from example B9 (450 mg) was dissolved in acetone (10 ml), 1 M HCl (5 ml) was added and the mixture was stirred for 3 hours at 45° C. The reaction mixture was concentrated, and extracted with dichloromethane. The organic layers were washed with sat. NaHCO$_3$ and brine, dried and evaporated. The residue was crystallized from ethanol, yielding 300 mg of compound 13.

NMR: (CDCl$_3$) δ 1.52-1.75 (m, CH), 1.60 (s, 6H, (CH3)$_2$), 1.95-2.15 (m, 2H, CH), 2.30 (d, 2H, CH), 2.50 (s, 2H, CH), 4.12 (dt, 1H, CH), 5.45 (d, 1H, NH), 7.27-7.47 (m, 5H, Ar—H).

Example B11

Preparation of

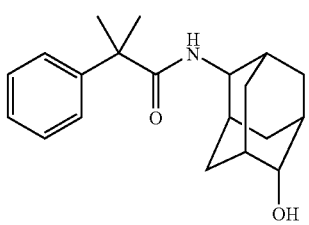

compound 14

Compound 13 (50 mg) was dissolved in MeOH and NaBH$_4$ (50 mg) was added. The mixture was stirred at room temperature for 6 hours. 1 M HCl was added, and the mixture was extracted with dichloromethane. The organic phase was washed with brine, dried and evaporated. Chromatography over silicagel (5% MeOH in dichloromethane) gave the 20 mg (40% of compound 14.

NMR: (CDCl$_3$) δ 1.52-2.00 (m, CH), 1.60 (s, 6H, (CH3)$_2$), 3.85 (dt, 1H, CH), 5.45 (d, 1H, NH), 7.23-7.42 (m, 5H, Ar—H).

Example B12

Preparation of

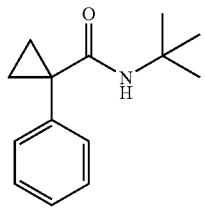

compound 17

1-Phenylcyclopropanecarboxylic acid (0.00028 mol); was added to a mixture of polymer-supported N-cyclohexylcarbodiimide (0.0004 mol) in dichloromethane (5 ml). The mixture was stirred for 15 minutes. 2-Methyl-2-propanamine (0.0002 mol) was added and the reaction mixture was stirred overnight at room temperature. The resin was filtered off and the filtrate was evaporated. The residue was purified over a prepacked silicagel liquid chromatography column (14 ml; eluent:dichloromethane). The product fractions were collected and the solvent was evaporated, yielding compound 17.

Example B13

Preparation of

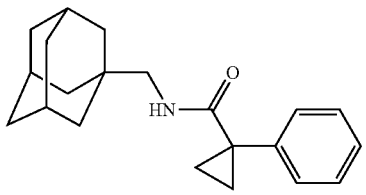

compound 31

Polymer-supported carbodiimide (0.0004 mol) was suspended in dichloromethane (5 ml). Then, 1-phenylcyclopropanecarboxylic acid (0.00028 mol) and N,N-dimethyl-4-pyridinamine (0.00001 mol) were added and the mixture was stirred for 20 minutes. Tricyclo[3.3.1.13,7]decane-1-methanamine (0.0002 mol; 6 variables) was added and the reaction mixture was stirred overnight at room temperature. The mixture was filtered. The filter residue was washed with dichloromethane and the filtrate's solvent was evaporated. The residue was purified by flash column chromatography on TRIKONEX FlashTube™ (eluent:hexane/EtOAc 9/2). The product fractions were collected and then extracted and the extracts were evaporated, yielding 0.037 of compound 31

Example B14 a) Preparation of

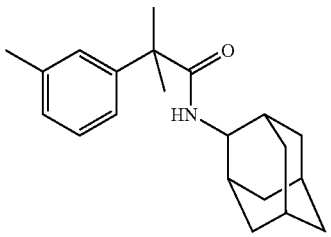

compound 89

A mixture of m, α-dimethylhydratropic acid (0.001 mol), 1-hydroxy-1H-benzotriazole (0.0011 mol) and N'-(ethylcarbonimidoyl)-N,N-dimethyl-1,3-propanediamine monohydrochloride (0.00105 mol) in dichloromethane (5 ml) was stirred until complete dissolution (±20 minutes) at room temperature. A mixture of 2-adamantanamine hydrochloride (0.0013 mol) in dichloromethane (2 ml), triethylamine (1 ml) and DMF (0.5 ml) was added and the resultant mixture was stirred overnight at room temperature. Water (2 ml) was added and the mixture was stirred for 10 minutes. The mixture was filtered through Extrelut™ and the filtrate's solvent was evaporated. The residue was purified by flash column chromatography on TRIKONEX FlashTube™ (eluent:CH$_2$Cl$_2$/EtOAc 95/5). The product fractions were collected and purified by HPLC. The product fractions were collected and the solvent was evaporated, yielding compound (89).

b) Preparation of

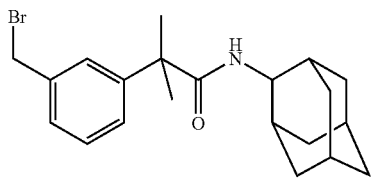

compound 270

A suspension of compound (89) (0.005 mol), 1-bromo-2,5-pyrrolidinedione, (0.0055 mol) and 2,2'-azobis(2-methylpropionitrile [cas: 78-67-1] (0.030 g) in tetrachloromethane (50 ml) was stirred and refluxed for 1 hour, then the precipitate was filtered off and the solvent was evaporated. The residue was dissolved in dichloromethane and the solution was washed with a 2% NaHCO$_3$ solution, with water and with brine. The mixture was dried and the solvent was evaporated, yielding 2 g of product. A part (0.100 g) of this residue was purified by high-performance liquid chromatography. The product fractions were collected and the solvent was evaporated, yielding compound (270).

c) Preparation of

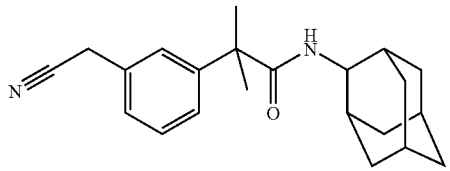

compound 161

A suspension of compound (270) (0.0013 mol), potassium cyanide (0.0065 mol) and potassium iodide (0.00013 mol) in acetonitrile (10 ml) was stirred overnight at room temperature and then the solvent was evaporated. The residue was dissolved in Dichloromethane and the solution was extracted with H$_2$O. The mixture was filtered over Extrelut™ and the solvent was evaporated. The residue was purified by column chromatography over silica gel (eluent:hexane/EtOAc 2/1). The product fractions were collected and the solvent was evaporated, yielding 0.12 g (96%) of compound (161).

d) Preparation of

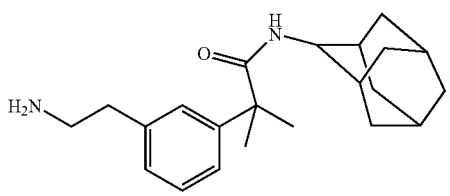

compound 170

A mixture of compound compound (161) (0.0009 mol) in a mixture of ammonia in methanol (50 ml) was hydrogenated at 14° C. with Raney nickel (cat. quant.) as a catalyst. After uptake of hydrogen (2 equiv.), the catalyst was filtered off and the filtrate was evaporated, yielding 0.270 g (88%) of compound (170).

e) Preparation of

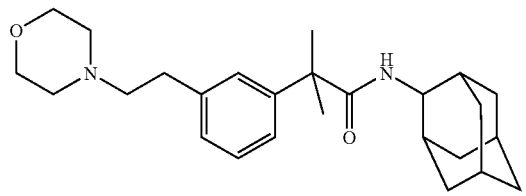

compound 191

A suspension of compound (170) (0.0006 mol) and potassium carbonate (0.0018 mol) in N,N-dimethylformamide (8 ml) was stirred for 15 minutes and a mixture of 1-chloro-2-(chloromethoxy)ethane (0.00066 mol) in N,N-dimethylformamide (q.s.) was added dropwise, then the reaction mixture was stirred over the weekend at room temperature. The mixture was heated overnight to 65° C. and extra 1-chloro-2-(chloromethoxy)ethane (0.030 g) was added. The resulting mixture was stirred for 3 hours at 65° C., then poured out into water and extracted with dichloromethane. The product was purified by high-performance liquid chromatography. The product fractions were collected, the solvent was evaporated and the residue was shaken with active charcoal, yielding 0.021 g (8.5%)) of compound (191).

Example B15

Preparation of compound 178

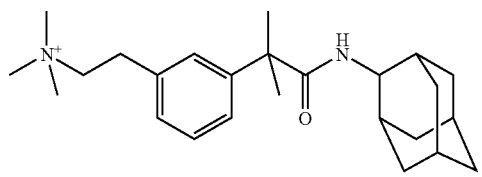

A mixture of iodomethane (0.001 mol) in N,N-dimethylformamide (1 ml) was added dropwise to a suspension of compound (170) (0.0003 mol) and potassium carbonate (0.001 mol) in N,N-dimethylformamide (3 ml) and the reaction mixture was stirred overnight at room temperature, then the mixture was poured out into water and washed with Dichloromethane. The resulting mixture was filtered over Extrelut™ and the solvent was evaporated, yielding product (NMR: CTS, LCMS: 100% MW 382). The residue was triturated under DIPE; the resulting precipitate was filtered off and dried, yielding 0.075 g (65%) of compound (178).

Example B16 a) Preparation of compound 271

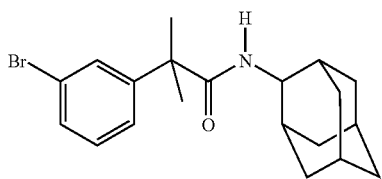

A mixture of 3-bromo-α,α-dimethylbenzeneacetic acid (0.0004 mol), 2-adamantanamine hydrochloride (0.0006 mol) and 1-hydroxy-1H-benzotriazole (0.0008 mol) in dichloromethane (5 ml), DMF (1 ml) and N,N-diethylethanamine (3 ml) was stirred, then N'-(ethylcarbonimidoyl)-N,N-dimethyl-1,3-propanediamine monohydrochloride (0.00045 mol) was added and the reaction mixture was stirred overnight. Water (2 ml) was added, the mixture was stirred for 10 minutes and filtered through Extrelut™. The solvent was evaporated and the residue was purified by flash column chromatography on TRIKONEX FlashTube™ (eluent:CH$_2$Cl$_2$/EtOAc 98/2). The product fractions were collected and the solvent was evaporated. The residue was further purified by high-performance liquid chromatography. The product fractions were collected and the solvent was evaporated. The residue was dissolved in dichloromethane and washed with a Na$_2$CO$_3$ solution. The mixture was filtered through Extrelut™ and the organic solvent was evaporated, yielding 0.0148 g of compound (271).

b) Preparation of compound 180

A mixture of compound (271) (0.00080 mol), 2-propenoic acid, ethyl ester (1 g), palladium(II)acetate (0.0002 mol), 1,3-propanediylbis[diphenylphosphine (0.0004 mol) and triethylamine (1 ml) in THF (100 ml) was reacted at 125° C. for 16 hours and then the solvent was evaporated. The residue (0.5 g) was purified by column chromatography over silica gel (eluent:dichloromethane). Two product fractions were collected and the solvent was evaporated, yielding 0.120 g (97%) of compound (180).

c) Preparation of compound 193

A mixture of compound (180) (0.0003 mol) in THF (40 ml) was hydrogenated with palladium on activated carbon (10%) (0.03 g) as a catalyst. After uptake of hydrogen (1 equiv.), the catalyst was filtered off and the filtrate was evaporated. The residue was dissolved in dichloromethane and the residue was purified by column chromatography over silica gel (eluent:dichloromethane). Two product fractions were collected and the solvent was evaporated, yielding 0.045 g of compound (193).

d) Preparation of compound 196

A mixture of compound (193) (0.00015 mol) and 1,4-dioxane (0.5 ml) in hydrochloric acid (2 ml) was stirred for 1 hour at 70° C. and then the solvent was evaporated. The residue was dissolved in dichloromethane and filtered over a silica-path (dichloromethane). The filtrate was evaporated and the resulting residue was dried, yielding 0.025 g (45%) of compound (196).

Example B17

Preparation of

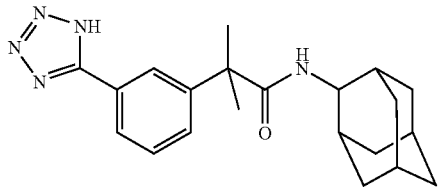

compound 159

A mixture of compound (271) (0.00013 mol), Pd$_2$(dibenzylideneacetone)$_3$ complex (0.026 g), 1,1'-bis(diphenylphosphino)ferrocene (0.033 g), Zn/Zn(CN)$_2$ (0.012 g/0.105 g), sodium azide (0.100 g) and ammoniumchloride (0.082 g) in DMA (50 ml) was reacted in a microwave at 150° C. for 45 minutes. Then the reaction mixture was poured out into water and extracted with EtOAc/DIPE. The extracts were washed with water and filtered over Extrelut™, then the solvent was evaporated. The aqueous phase was extracted with dichloromethane and filtered over Extrelut™. The solvent was evaporated and the residue was purified by high-performance reverse phase liquid chromatography. The product fractions were collected and the solvent was evaporated, yielding compound (159).

Example B18

Preparation of

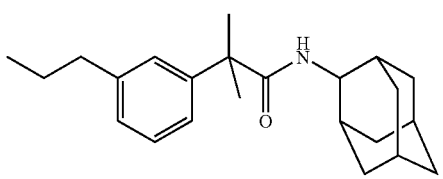

compound 166

Butyllithium (0.0011 mol) was added dropwise under N$_2$ at −78° C. to a solution of compound (271) (0.0005 mol) in THF (5 ml) and the mixture was stirred for 30 minutes. Then a mixture of iodopropane (0.0006 mol) in THF (5 ml) was added dropwise and the reaction mixture was stirred for 1 hour at −78° C. The mixture was allowed to warm overnight and then a saturated NH$_4$Cl-solution (5 ml) was added. The organic layer was separated, washed, filtered over Extrelut™ and the solvent was evaporated. The residue (0.170 g) was purified on a prepacked silicagel liquid chromatography column (5 g) (eluent:hexane/EtOAc 10/1). The product fractions were collected and the solvent was evaporated. The residue was purified by high-performance reverse phase liquid chromatography. The product fractions were collected and the solvent was evaporated, yielding compound (166).

Example B19 a) Preparation of

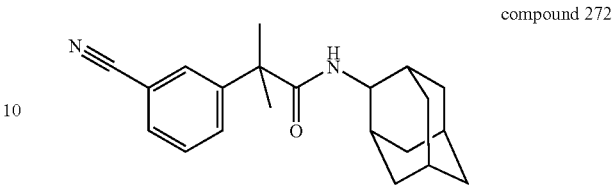

compound 272

A mixture of compound (271) (0.00013 mol), Pd$_2$(dibenzylideneacetone)$_3$ complex (0.026 g), 1,1'-bis(diphenylphosphino)ferrocene (0.033 g) and Zn/Zn(CN)$_2$ (0.012 g/0.105 g) in DMA (50 ml) was reacted in a microwave at 150° C. for 15 minutes, then the reaction mixture was poured out into water and extracted with EtOAc/DIPE. The extracts were washed with water and the solvent was evaporated. The residue was purified by solid phase extraction on a prepacked silicagel liquid chromatography column (eluent: CH$_2$Cl$_2$). The product fractions were collected and the solvent was evaporated, yielding 0.055 g of compound (272).

b) Preparation of

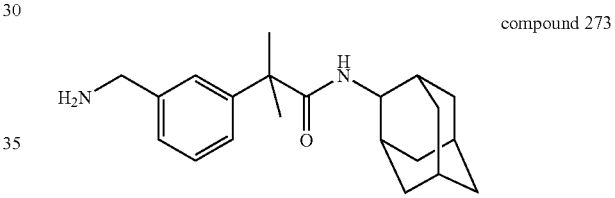

compound 273

A mixture of compound (272) (0.001 mol) in a solution of ammonia in methanol (50 ml) was hydrogenated at 14° C. with Raney nickel (cat. quant.) as a catalyst. After uptake of hydrogen (2 equiv.), the catalyst was filtered off and the filtrate was evaporated. The residue was dissolved in dichloromethane, the solution was filtered and the filtrate was evaporated, yielding 0.270 g of compound (273).

c) Preparation of

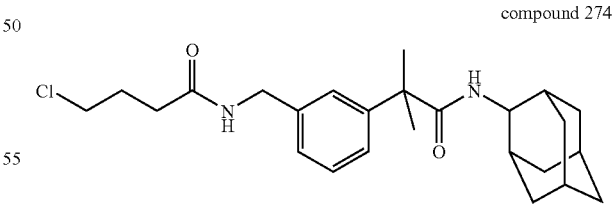

compound 274

A solution of compound (273) (0.00015 mol) and N,N-diethylethanamine (0.0003 mol) in dichloromethane (q.s.) was stirred for 15 minutes at room temperature. Then a mixture of 4-chlorobutanoyl chloride [4635-59-0] (0.000165 mol) in dichloromethane (2.5 ml) was added dropwise and the reaction mixture was stirred overnight at room temperature. The mixture was washed with HCl (1N), with a 5% NaHCO$_3$ solution and with water. The resulting mixture was filtered over Extrelut™ and the solvent was evaporated. The residue was purified by column chromatography over silica gel (eluent:CH$_2$Cl$_2$/CH$_3$OH 99/1). The product fractions were collected and the solvent was evaporated, yielding 0.072 g of compound (274) (colourless oil).

d) Preparation of

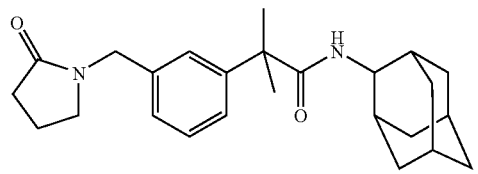

compound 160

N,N,N-triethylbenzenemethanaminium chloride (0.00015 mol) and sodium hydroxide (50%) (0.5 ml) were added to a solution of compound (274) (0.00014 mol) in dichloromethane (5 ml) and the reaction mixture was stirred overnight at room temperature. The mixture was washed 2 times with HCl (1N), with a 5% NaHCO$_3$ solution and with water. The resulting mixture was filtered over Extrelut™ and the solvent was evaporated, yielding 0.050 g of a colourless oil. The residue was purified by solid phase extraction on a prepacked silicagel liquid chromatography column (eluent: CH$_2$Cl$_2$/CH$_3$OH 90/10). The product fractions were collected and the solvent was evaporated, yielding 0.024 g of compound (160).

Example B20 a) Preparation of

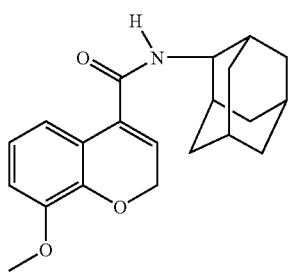

compound 171

A mixture of intermediate (29) (0.0019 mol) in N,N-diethylethanamine (2 ml) and dichloromethane (15 ml) was stirred and 1-hydroxy-1H-benzotriazole (0.002 mol) was added. Then N'-(ethylcarbonimidoyl)-N,N-dimethyl-1,3-propanediamine (0.002 mol) was added and the mixture was stirred for 10 minutes. 2-Adamantanamine hydrochloride (0.0022 mol) was added and the reaction mixture was stirred overnight. A citric acid solution. (2 ml) was added and the resulting mixture was filtered through Extrelut™. The filtrate was evaporated and the residue was purified by flash column chromatography on TRIKONEX FlashTube™ (eluent:CH$_2$Cl$_2$/EtOAc 90/10). The product fractions were collected and the solvent was evaporated. This residual fraction was purified by high-performance liquid chromatography, then the product fractions were collected and the solvent was evaporated, yielding 0.155 g (25%) of compound (171).

b) Preparation of

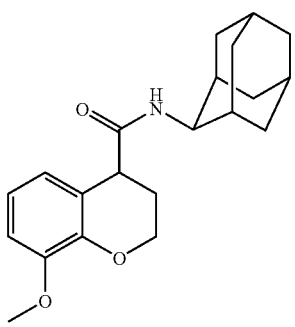

compound 172

A mixture of compound (171) (0.00044 mol) in methanol (50 ml) was hydrogenated overnight with palladium on activated carbon (0.1 g) as a catalyst. After uptake of hydrogen (1 equiv.), the catalyst was filtered off and the filtrate was evaporated, then the residue was dried (vac.), yielding 0.12 g of compound (172).

Example B21

Preparation of

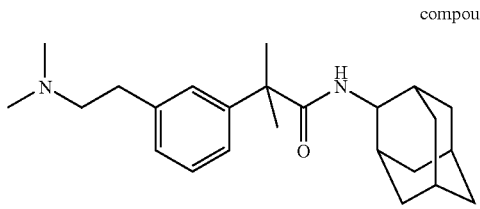

compound 192

A mixture of compound (170) (0.0006 mol) and formaldehyde (0.2 g) in methanol (40 ml) was hydrogenated at 50° C. with palladium on activated carbon (0.05 g) as a catalyst in the presence of a thiophene solution (0.1 ml). After uptake of hydrogen (2 equiv.), the catalyst was filtered off and the filtrate was evaporated. The residue was dissolved in dichloromethane, washed with HCl (1N), with a 5% NaHCO$_3$ solution and with brine. The mixture was filtered over Extrelut™ and the solvent was evaporated. The residue was purified by column chromatography over silica gel (eluent: CH$_2$Cl$_2$/(CH$_3$OH/NH$_3$ (1%)) 90/10). The product fractions were collected and the solvent was evaporated, yielding compound (192).

Example B22 a) Preparation of compound 198

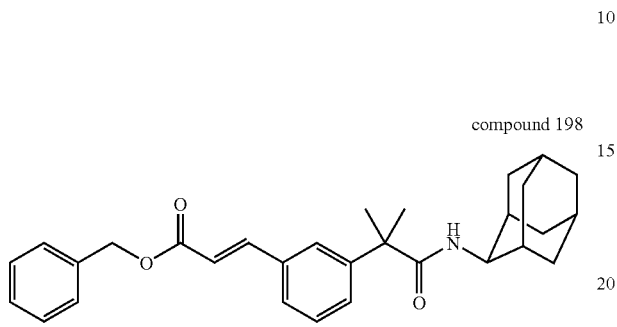

A mixture of compound (271) (0.0005 mol), 2-propenoic acid, phenylmethyl ester (0.002 mol), Pd$_2$(dibenzylideneacetone)$_3$ complex (0.0001 mol), tris(2-methylphenyl)phosphine [6163-58-2] (0.00025 mol) and N,N-dibutyl-1-butanamine (0.0025 mol) in DMF (5 ml) was stirred overnight at 90° C. and then the reaction mixture was cooled. Water (3 ml) was added and the mixture was extracted with EtOAc. The organic layer was separated, dried (MgSO$_4$), filtered off and the solvent was evaporated. The residue was purified by column chromatography over silica gel (eluent:dichloromethane). The product fractions were collected and the solvent was evaporated, yielding 0.167 g of compound (198).

b) Preparation of compound 202

A mixture of compound (198) (0.0003 mol) in acetic acid (4 ml) and hydrochloric acid (2 ml) was stirred overnight at 60° C., then the reaction mixture was cooled and extracted with dichloromethane. The organic layer was separated, washed, dried, filtered off and the solvent was evaporated. The residue was purified by high-performance liquid chromatography. The product fractions were collected and the solvent was evaporated, yielding 0.045 g of compound (202).

Example B23 a) Preparation of compound 204

A mixture of intermediate (36) (0.0013 mol) in dichloromethane (10 ml) and N,N-diethylethanamine (3 ml) was stirred and 1-hydroxy-1H-benzotriazole (0.002 mol) was added. Then N'-(ethylcarbonimidoyl)-N,N-dimethyl-1,3-propanediamine monohydrochloride (0.002 mol) was added and the mixture was stirred for 10 minutes. After addition of DMF (2 ml), 2-adamantanamine hydrochloride (0.0016 mol) was added and the reaction mixture was stirred overnight. The mixture was washed with water (2 ml), with a potassium hydroxide solution and washed again with water. The organic layer was separated, dried (MgSO$_4$), filtered off and the solvent was evaporated. The residue was purified by column chromatography over silica gel (eluent:CH$_2$Cl$_2$/CH$_3$OH 98/2). The product fractions were collected and the solvent was evaporated, yielding 0.176 g of compound (204).

b) Preparation of compound 208

A mixture of compound (204) (0.00036 mol) in a solution of TFA in dichloromethane (28%) (3 ml) was stirred for 3 hours and then the solvent was evaporated. The residue was dissolved in dichloromethane and the solution was washed with a Na$_2$CO$_3$ solution. The organic layer was separated, filtered through Extrelut™ and the solvent was evaporated, yielding 0.116 g of compound (208).

Example B24

Preparation of

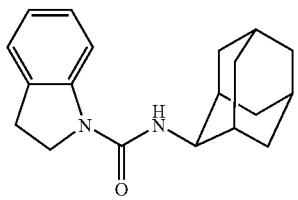

compound 252

A mixture of 1-[(2,3-dihydro-1H-indol-1-yl)carbonyl]-3-methyl-1H-imidazolium, iodide [548763-29-7] (0.0028 mol) and 2-adamantanamine hydrochloride (0.0028 mol) in N,N-diethylethanamine (2 ml) and a mixture of dichloromethane, THF and DMF (1/1/0.5) (50 ml) was stirred over the weekend, then the reaction mixture was poured out into water and extracted with dichloromethane. The extracts were washed with a solution of citric acid (15%) and the organic layer was dried, then filtered. The solvent was evaporated and the residue was purified by flash column chromatography on TRIKONEX FlashTube™ (eluent: CH$_2$Cl$_2$/EtOAc 90/10). The product fractions were collected and the solvent was evaporated, yielding 0.18 g of compound (252).

Example B25

Preparation of

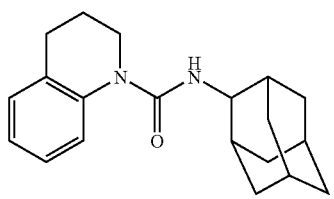

compound 200

2-Isocyanato-tricyclo[3.3.1.1$^{3,7}$]decane [71189-14-5] (0.0053 mol) was added to a solution of 1,2,3,4-tetrahydroquinoline (0.00586 mol) in EtOAc (10 ml) and the reaction mixture was stirred overnight. The solvent was evaporated and the residue was crystallised from 2-propanol. Finally, the desired product was collected, yielding 0.500 g compound (200); m.p. 163-165° C.

Example B26

Preparation of

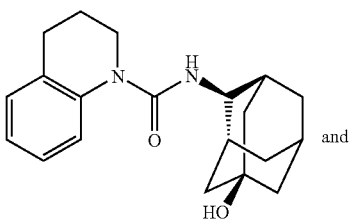

compound 219 and

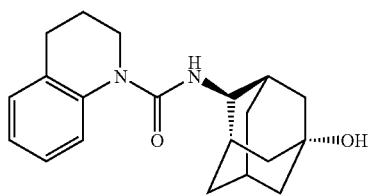

compound 218

1-[(3,4-dihydro-1 (2H)-quinolinyl)carbonyl]-3-methyl-1H-imidazolium, iodide [213134-25-9] (0.01 mol) was added to a solution of 4-amino-tricyclo[3.3.1.1$^{3,7}$]-decan-1-ol [75375-89-2] (0.01 mol) and N,N-diethylethanamine (0.01 mol) in a mixture of dichloromethane, THF and DMF (1/1/0.2) (100 ml) and the reaction mixture was stirred overnight. The mixture was washed with 1N HCl, with 2N potassium hydroxide and with sodium chloride, then dried and the solvent was evaporated. The residue was purified by column chromatography over silica gel (eluent:hexane/EtOAc 3/1->1/1). Two product fractions were collected and the solvent was evaporated, yielding 1.5 g (46%) of compound (219); m.p. 185-188° C. and 1.4 g (44%) of compound (218); m.p. 170-172° C.

Example B27

Preparation of

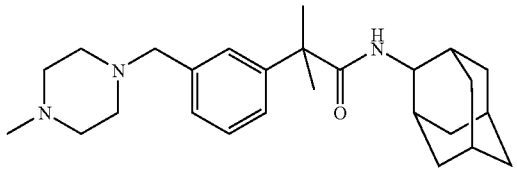

compound 231

1-Methylpiperazine (0.0015 mol) was added in one portion to a solution of compound (270) (0.0003 mol) in dichloromethane (5 ml) and then the mixture was stirred overnight at room temperature. Sodium hydroxide (1N) (1 ml) was added and the reaction mixture was stirred vigorously for 30 minutes. The layers were separated and the aqueous layer was extracted. The organic layer was dried, filtered off and the solvent was evaporated, yielding compound (231).

Example B28

Preparation of

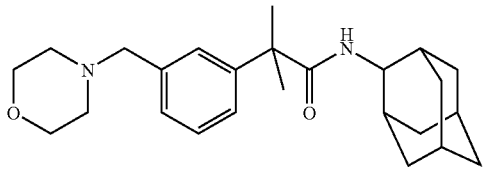

compound 232

Morpholine (0.0012 mol) was added to a solution of compound (270) (0.00044 mol) in dichloromethane (10 ml) and then the mixture was stirred overnight at room temperature. Sodium hydroxide (1N) (1 ml) was added and the reaction mixture was stirred vigorously for 15 minutes. The aqueous layer was separated and then the organic layer was washed with water and filtered through Extrelut™. The filtrate was evaporated and the residue was purified by column chromatography over silica gel (eluent:$CH_2Cl_2$/$CH_3OH$ 99/1). The product fractions were collected and the solvent was evaporated, yielding compound (232).

Example B29 a) Preparation of

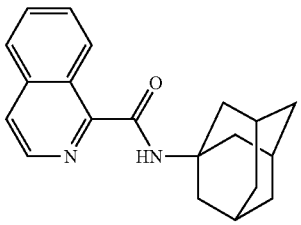

compound 265

A mixture of 1-isoquinolinecarboxylic acid (0.0056 mol) in DMF (50 ml) was stirred and 1-hydroxy-1H-benzotriazole (0.0067 mol) was added. Then N'-(ethylcarbon-imidoyl)-N,N-dimethyl-1,3-propanediamine monohydrochloride (0.00067 mol) was added and the mixture was stirred for 20 minutes. 1-Adamantanamine [768-94-5] (0.0067 mol) was added and the reaction mixture was stirred for 3 hours. The resulting mixture was poured out into water and was then extracted with EtOAc. The separated organic layer was washed, dried ($MgSO_4$), filtered off and the solvent was evaporated. The residual fraction was purified by column chromatography over silica gel (eluent:dichloromethane). The product fractions were collected and the solvent was evaporated, yielding 1.5 g of compound (265).

Preparation of

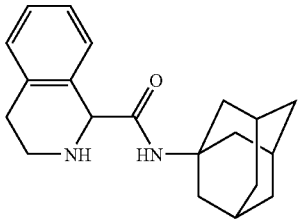

compound 267

A mixture of compound (265) (0.004 mol) and hydrochloric acid (12N) (1 ml) in methanol (50 ml) was hydrogenated overnight with platinum on activated carbon (1 g) as a catalyst. After uptake of hydrogen (2 equiv.), the catalyst was filtered off and the filtrate was evaporated. The residue was dissolved in dichloromethane and washed with a sodium carbonate solution. The organic layer was separated, dried ($MgSO_4$), filtered off and the solvent was evaporated. The residue was purified by column chromatography over silica gel (eluent:$CH_2Cl_2$/$CH_3OH$ 99/1->95/5). Two product fractions were collected and the solvent was evaporated, yielding 0.8 g of compound (267).

Example B30 a) Preparation of

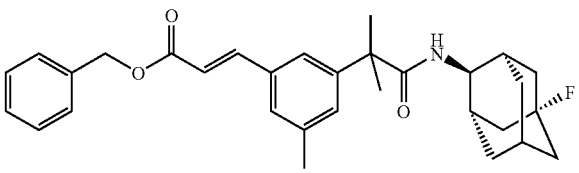

compound 278

Compound 238 (0.0036 mol) was dissolved in $CH_2Cl_2$ (50 ml) and the solution was cooled to -70° C., then DAST (0.0015 mol) was added dropwise and the reaction mixture was stirred for 30 min. at -70° C. After removing the cold bath, the mixture was allowed to reach room temperature in 1 hour and then a satd. $NaHCO_3$ soln. was added portionwise. The separated organic layer was washed with water and with brine, then dried, filtered and the solvent was evaporated. The residue was purified by column chromatography over silica gel (eluent:$CH_2Cl_2$/$CH_3OH$ 98/2). The product fractions were collected and the solvent was evaporated, yielding 1 g compound (278)(LCMS: 94% P).

b) Preparation of

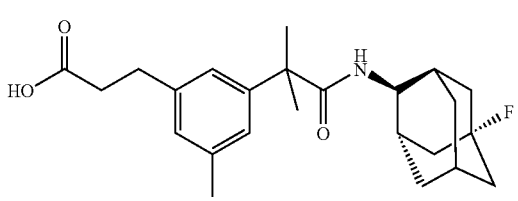

compound 279

A mixture of compound (278) (0.002 mol) in THF (50 ml) was hydrogenated with Pd/C 10% (0.2 g) as a catalyst. After uptake of hydrogen (2 equiv.), the catalyst was filtered off and the filtrate was evaporated (vac.). The residue was triturated under DIPE and after collection the crude product was purified by column chromatography over silica gel (eluent:CH$_2$Cl$_2$/CH$_3$OH 99/1). The product fractions were collected and their solvent was evaporated, yielding compound (279).

Example B31 a) Preparation of compound 280

A suspension of intermediate 12 (0.0192 mol), N'-(ethyl-carbonimidoyl)-N,N-dimethyl-1,3-propanediamine (0.021 mol) and HOBt (0.021 mol) in DMF (10 ml) was stirred for 30 min. at room temperature, then 2-amino-adamantane hydrochloride[62058-03-1] (0.0231 mol) in DMF (q.s.) was added and the reaction mixture was stirred overnight. The resulting crude was triturated under DIPE and the desired product was collected, yielding 7.8 g of compound (280) (83%).

b) Preparation of compound 281

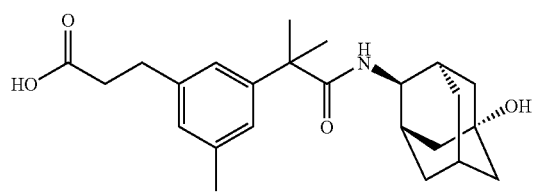

A mixture of compound (280)(0.0065 mol) in THF (150 ml) was hydrogenated with B (1 g) as a catalyst. After uptake of hydrogen (2 equiv.), the catalyst was filtered off and the filtrate was evaporated (vac.), yielding 2.6 g of compound (281) (100%).

c) Preparation of

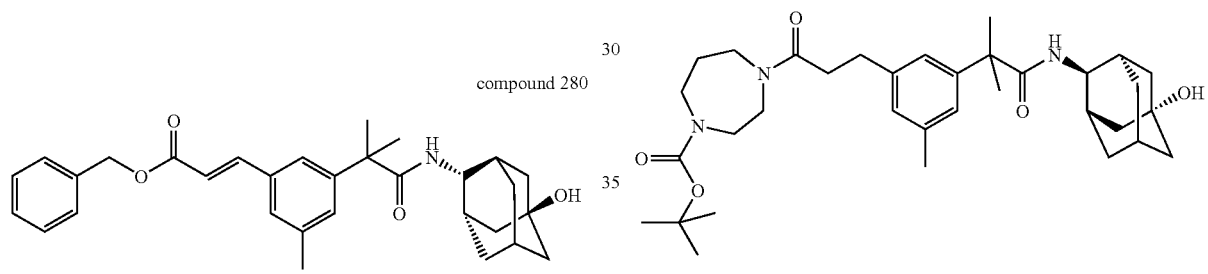

compound 277

A solution of compound (281)(0.00024 mol), N'-(ethyl-carbonimidoyl)-N,N-dimethyl-1,3-propanediamine (0.000275 mol) and HOBt (0.000275 mol) in DMF (10 ml) was stirred for 30 min. at room temperature and then B (0.000325 mol) was added. The reaction mixture was stirred overnight at room temperature, washed with water and with a 5% NaHCO$_3$ soln. and then was filtered through Extrelut™. The solvent was evaporated and the residue (0.200 g) was purified by column chromatography over silica gel (2 g) (eluent:CH$_2$Cl$_2$/CH$_3$OH 95/5). The pure product fractions were collected and the solvent was evaporated. Finally, the desired product was dried (vac.), yielding 0.106 g of compound (277).

Tables 1, 2 and 3 list compounds of the present invention as prepared according to one of the above examples.

TABLE 1
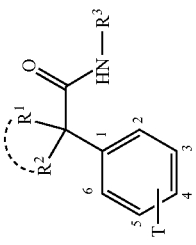
| Co. No. | Ex No. | R¹ | R² | R¹ R² | —R³ | T | Physical data |
|---|---|---|---|---|---|---|---|
| 16 | B3 | — | — | —(CH$_2$)$_3$— | adamantyl | — | |
| 17 | B12 | — | — | —(CH$_2$)$_2$— | —C(CH$_3$)$_3$ | — | |
| 18 | B12 | — | — | —(CH$_2$)$_2$— | —C(CH$_3$)$_2$—CH$_2$—C(CH$_3$)$_3$ | — | |
| 19 | B12 | — | — | —(CH$_2$)$_2$— | 2-methylcyclohexyl | — | |
| 20 | B12 | — | — | —(CH$_2$)$_2$— | 2-methylbiphenyl | — | |
| 21 | B12 | — | — | —(CH$_2$)$_4$— | —C(CH$_3$)$_3$ | — | |
| 22 | B12 | — | — | —(CH$_2$)$_4$— | methylnorbornyl | — | |

TABLE 1-continued
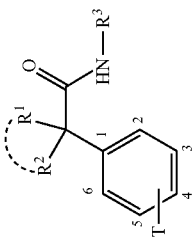
| Co. No. | Ex No. | R¹ | R² | R¹—R² | —R³ | T | Physical data |
|---|---|---|---|---|---|---|---|
| 23 | B12 | — | — | —(CH$_2$)$_4$— | 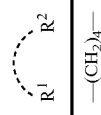 | — | |
| 24 | B12 | — | — | —(CH$_2$)$_4$— | 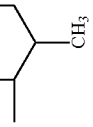 | — | |
| 25 | B12 | — | — | —(CH$_2$)$_5$— | 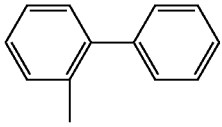 | — | |
| 26 | B12 | — | — | —(CH$_2$)$_5$— | 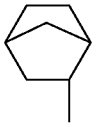 | — | |
| 1 | B1 | CH$_3$ | CH$_3$ | — | 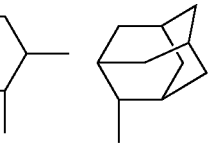 | 4-Cl | |

TABLE 1-continued
| Co. No. | Ex No. | R¹ | R² | R¹ R² | −R³ | T | Physical data |
|---|---|---|---|---|---|---|---|
| 27 | B1 | — | — | —(CH$_2$)$_2$— |  | 4-Cl | |
| 28 | B1 | CH$_3$ | — | — |  | — | |
| 2 | B2 | CH$_3$ | CH$_3$ | — |  | — | |
| 29 | B1 | C$_2$H$_5$ | — | — |  | — | |
| 30 | B1 | — | — | — |  | — | |

TABLE 1-continued
| Co. No. | Ex No. | R$^1$ | R$^2$ | R$^1$ R$^2$ | —R$^3$ | T | Physical data |
|---|---|---|---|---|---|---|---|
| 31 | B13 | — | — | —(CH$_2$)$_2$— | 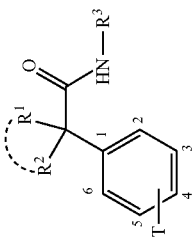 | — | |
| 32 | B1 | — | — | —(CH$_2$)$_2$— | 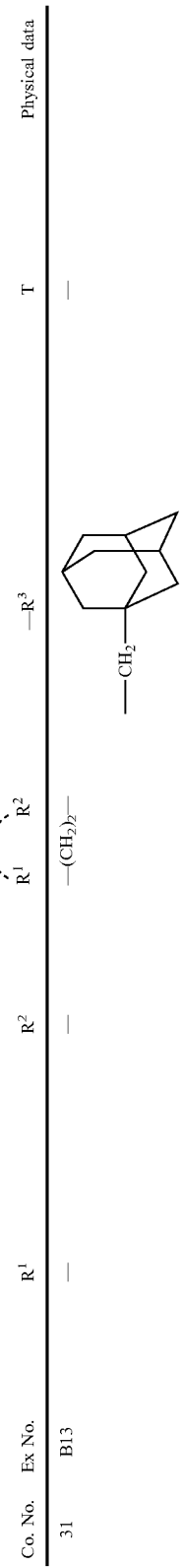 | — | |
| 33 | B13 | — | — | —(CH$_2$)$_2$— |  | — | |
| 34 | B13 | — | — | —(CH$_2$)$_2$— |  | — | |
| 35 | B13 | — | — | —(CH$_2$)$_4$— | 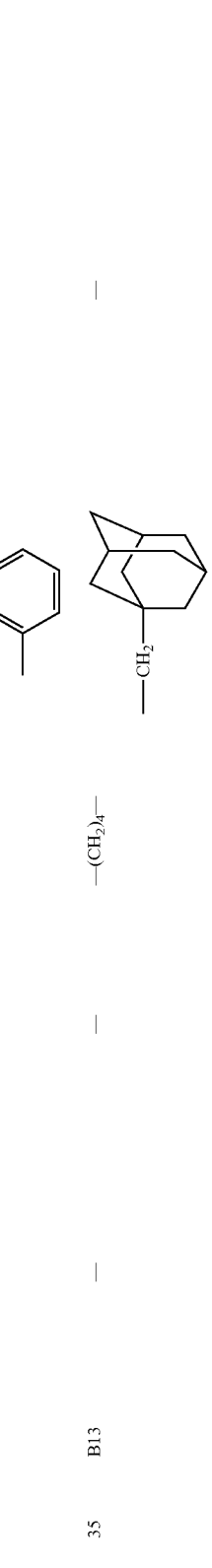 | — | |

TABLE 1-continued

| Co. No. | Ex No. | R¹ | R² | R¹ R² | R³ | T | Physical data |
|---|---|---|---|---|---|---|---|
| 36 | B13 | — | — | —(CH₂)₄— | tetrahydronaphthyl | — | |
| 37 | B13 | — | — | —(CH₂)₆— | adamantyl-CH₂— | — | |
| 38 | B1 | — | — | —(CH₂)₄— | adamantyl | — | |
| 39 | B1 | — | — | —(CH₂)₃— | adamantyl | 4-Cl | |
| 40 | B2 | — | — | —(CH₂)₃— | adamantyl | — | |

TABLE 1-continued

| Co. No. | Ex No. | R¹ | R² | —R³ | T | Physical data |
|---|---|---|---|---|---|---|
| 41 | B1 | CH₃ | CH₃ | adamantyl | 4-F | — |
| 42 | B1 | C(CH₃)₃—O—CO—NH— | — | adamantyl | — | — |
| 43 | B1 | CH₃O | — | adamantyl | — | — |
| 44 | B1 | C(CH₃)₃—O—CO—NH— | —C(CH₃)₃—O—CO—NH— | adamantyl | — | — |
| 45 | B1 | CH₃ | CH₃ | cyclohexyl-derivative | — | — |

TABLE 1-continued
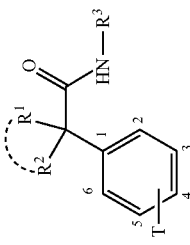
| Co. No. | Ex No. | R¹ | R² | R² R¹ | —R³ | T | Physical data |
|---|---|---|---|---|---|---|---|
| 46 | B1 | CH₃ | CH₃ | — | cyclooctyl | — | |
| 4 | B4 | CH₃ | CH₃ | — | adamantyl | 3-OCH₃ | |
| 47 | B4 | CH₃ | CH₃ | — | adamantyl | 4-OCH₃ | |
| 48 | B4 | CH₃ | CH₃ | — | bicyclic | — | |
| 49 | B1 | — | — | —(CH₂)₂— | azabicyclic | — | |
| 5 | B4 | CH₃ | CH₃ | — | adamantyl | 3-OH | |

TABLE 1-continued
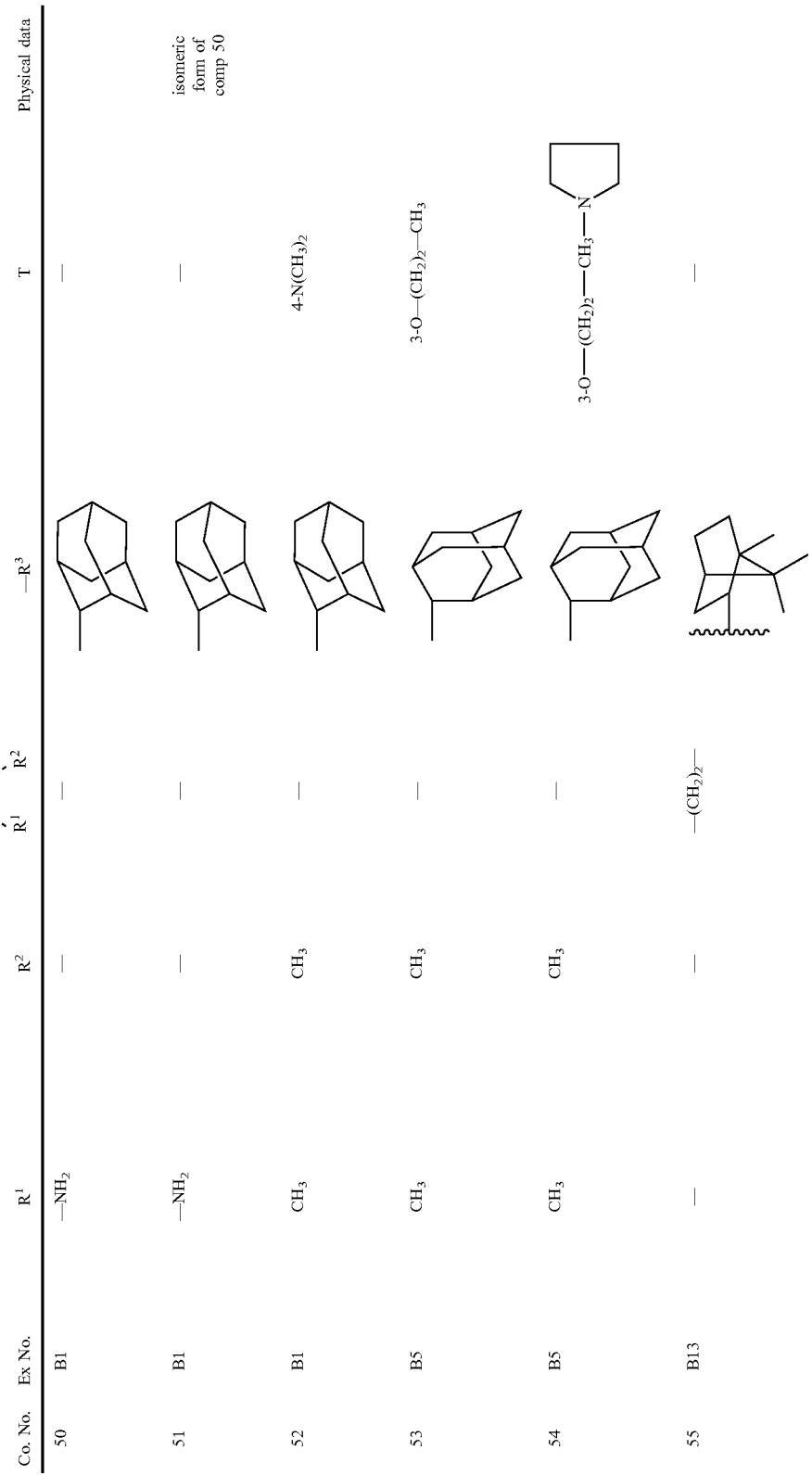
| Co. No. | Ex No. | R¹ | R² | R¹ R² | —R³ | T | Physical data |
|---|---|---|---|---|---|---|---|
| 50 | B1 | —NH₂ | — | — | adamantyl | — | |
| 51 | B1 | —NH₂ | — | — | adamantyl | — | isomeric form of comp 50 |
| 52 | B1 | CH₃ | CH₃ | — | adamantyl | 4-N(CH₃)₂ | |
| 53 | B5 | CH₃ | CH₃ | — | adamantyl | 3-O—(CH₂)₂—CH₃ | |
| 54 | B5 | CH₃ | CH₃ | — | adamantyl | 3-O—(CH₂)₂—CH₃—N(pyrrolidinyl) | |
| 55 | B13 | — | — | —(CH₂)₂— | bornyl | — | |

TABLE 1-continued
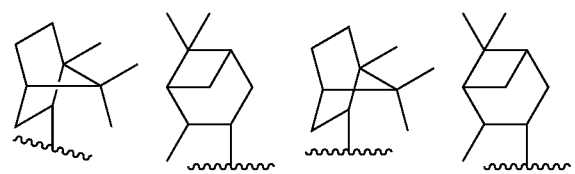
| Co. No. | Ex No. | R¹ | R² | R¹ R² | —R³ | T | Physical data |
|---|---|---|---|---|---|---|---|
| 56 | B13 | — | — | —(CH₂)₂— | 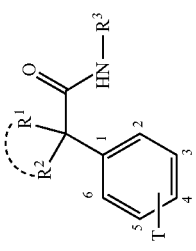 | — | |
| 57 | B13 | — | — | —(CH₂)₄— | | — | |
| 58 | B13 | — | — | —(CH₂)₄— | | — | |
| 59 | B13 | — | — | —(CH₂)₅— | | — | |
| 60 | B13 | — | — | —(CH₂)₅— | 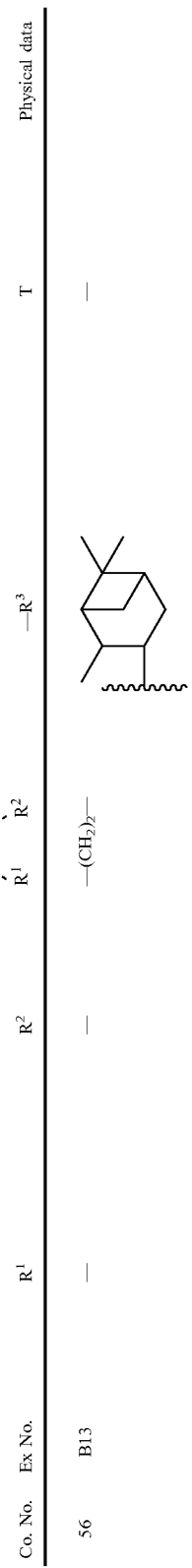 | — | |

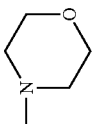

TABLE 1-continued

| Co. No. | Ex No. | R¹ | R² | R¹/R² | R³ | T | Physical data |
|---|---|---|---|---|---|---|---|
| 9 | B6 | CH₃ | CH₃ | — | 1-hydroxyadamantan-3-yl | — | |
| 66 | B1 | —CH₂—O—(tetrahydropyran-2-yl) | — | — | adamantan-2-yl | — | |
| 67 | B1 | CH₃ | CH₃ | — | adamantan-1-yl | 4-N(CH₂-Ph)₂ | |
| 68 | B1 | CH₃ | — | — | adamantan-2-yl | 4-NO₂ | |

TABLE 1-continued
| Co. No. | Ex No. | R¹ | R² | —R³ | T | Physical data |
|---|---|---|---|---|---|---|
| 69 | B1 | — | — | 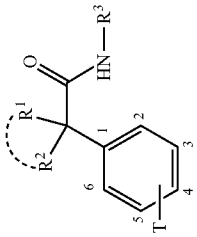 | 4-N-(CH₂-Ph)₂ | |
| 70 | B4 | CH₃ | CH₃ | 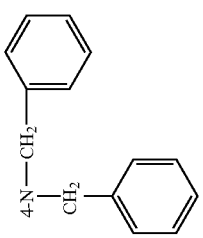 | 4-OH | |
| 71 | B5 | CH₃ | CH₃ |  | 3-O—(CH₂)₂—N(CH₃)₂ | |
| 7 | B5 | CH₃ | CH₃ |  | 3-O—(CH₂)₂—N(CH₃)—CH₃ | |
| 72 | B1 | CH₃ | CH₃ | 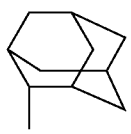 | 4-O—CH₂—COOH | |

TABLE 1-continued
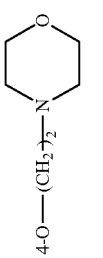
| Co. No. | Ex No. | R¹ | R² | R¹ R² | —R³ | T | Physical data |
|---|---|---|---|---|---|---|---|
| 73 | B5 | CH₃ | CH₃ | — |  | 4-O—(CH₂)₂—N | |
| 74 | B4 | CH₃ | CH₃ | — | 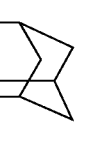 | 3-O—CH₃ | |
| 75 | B4 | CH₃ | CH₃ | — |  | 3-O—CH₃ | |
| 76 | B1 | CH₃ | CH₃ | — | 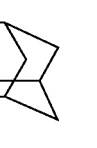 | 3-NH₂ | |
| 77 | B1 | CH₃ | CH₃ | — |  | 3-NH—CH₃ | |

TABLE 1-continued

![Structure: phenyl with R1, R2 on alpha carbon bearing C(=O)NH-R3, T on ring]

| Co. No. | Ex No. | R¹ | R² | R¹ R² | —R³ | T | Physical data |
|---------|--------|------|------|-------|-----|---|---------------|
| 78 | B1 | CH₃ | CH₃ | — | adamantyl | 3-N(CH₃)₂ | |
| 79 | B1 | CH₃ | CH₃ | — | adamantyl | 4-NH₂ | |
| 80 | B1 | CH₃ | CH₃ | — | adamantyl | 4-NH—CH₃ | |
| 81 | B1 | CH₃ | CH₃ | — | adamantyl | 4-N(CH₃)—(CH₂)—C₆H₅ | |
| 82 | B1 | —N(CH₃)₂— | — | — | adamantyl | — | |

TABLE 1-continued
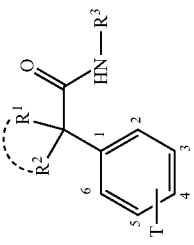
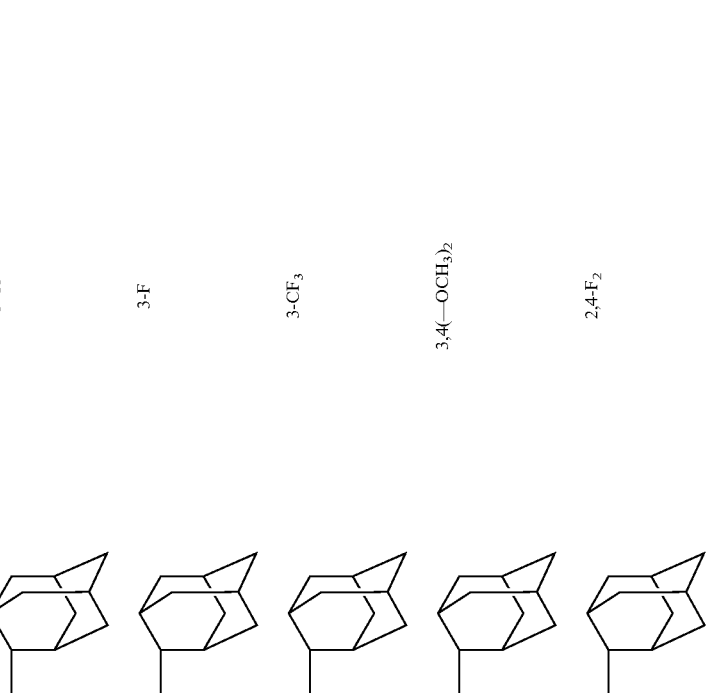
| Co. No. | Ex No. | R¹ | R² | R² R¹ | —R³ | T | Physical data |
|---|---|---|---|---|---|---|---|
| 83 | B1 | CH₃ | CH₃ | — | adamantyl | 3-Cl | |
| 84 | B1 | CH₃ | CH₃ | — | adamantyl | 3-F | |
| 85 | B1 | CH₃ | CH₃ | — | adamantyl | 3-CF₃ | |
| 86 | B1 | CH₃ | CH₃ | — | adamantyl | 3,4-(—OCH₃)₂ | |
| 87 | B1 | CH₃ | CH₃ | — | adamantyl | 2,4-F₂ | |

TABLE 1-continued
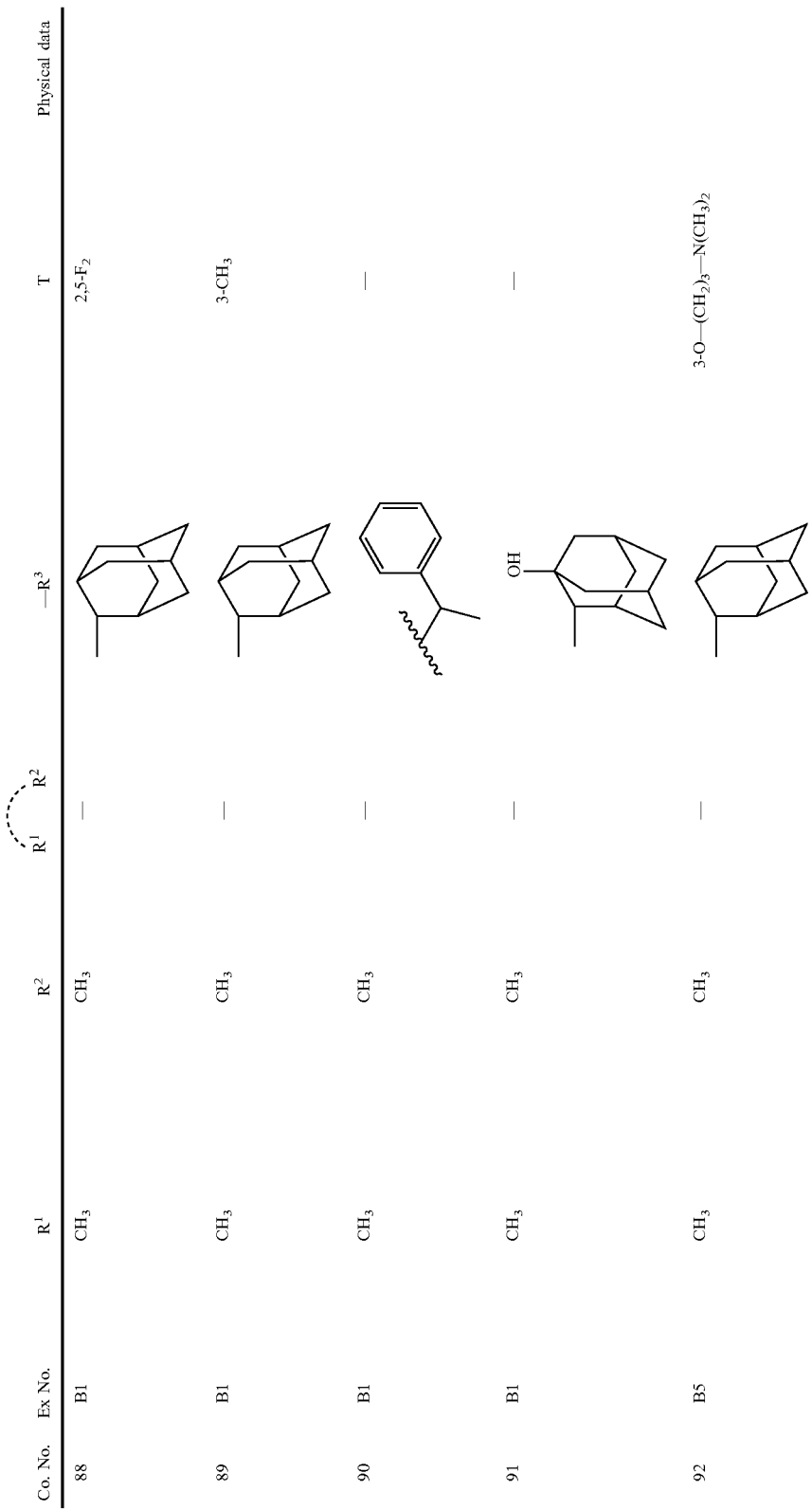
| Co. No. | Ex No. | R¹ | R² | —R³ | T | Physical data |
|---|---|---|---|---|---|---|
| 88 | B1 | $CH_3$ | $CH_3$ | 2-methyladamantyl | 2,5-$F_2$ | |
| 89 | B1 | $CH_3$ | $CH_3$ | 2-methyladamantyl | 3-$CH_3$ | |
| 90 | B1 | $CH_3$ | $CH_3$ | isopropyl-phenyl | — | |
| 91 | B1 | $CH_3$ | $CH_3$ | 3-hydroxy-methyladamantyl | — | |
| 92 | B5 | $CH_3$ | $CH_3$ | 2-methyladamantyl | 3-O—$(CH_2)_3$—$N(CH_3)_2$ | |

TABLE 1-continued

| Co. No. | Ex No. | R¹ | R² | —R³ | T | Physical data |
|---|---|---|---|---|---|---|
| 8 | B6 | $CH_3$ | $CH_3$ | 1-hydroxyadamantyl | — | |
| 93 | B1 | $CH_3$ | $CH_3$ | adamantyl | 2,5-($-O-CH_3$) | |
| 94 | B1 | $CH_3$ | $CH_3$ | adamantyl | 2-O-$C_6H_5$ | |
| 95 | B1 | $CH_3$ | $CH_3$ | adamantyl | 3,5-$F_2$ | |
| 96 | B3 | $CH_3$ | $CH_3$ | 1-phenylethyl | — | isomeric form of comp 90 |

TABLE 1-continued

| Co. No. | Ex No. | R¹ | R² | —R³ | T | Physical data |
|---|---|---|---|---|---|---|
| 97 | B3 | CH₃ | CH₃ | 4-methoxyphenyl-CH(iPr)- | — | |
| 98 | B3 | CH₃ | CH₃ | 4-methoxyphenyl-CH(iPr)- | — | isomeric form of comp 97 |
| 99 | B3 | CH₃ | CH₃ | phenyl-CH(Et)- | — | |
| 100 | B3 | CH₃ | CH₃ | phenyl-CH(Et)- | — | isomeric form of comp 99 |
| 101 | B3 | CH₃ | CH₃ | 1-methylindanyl | — | |

TABLE 1-continued

| Co. No. | Ex No. | R¹ | R² | R³ | T | Physical data |
|---|---|---|---|---|---|---|
| 102 | B3 | $CH_3$ | $CH_3$ | 1-methyl-indanyl | — | isomeric form of comp 101 |
| 103 | B3 | $CH_3$ | $CH_3$ | 1-methyl-indanyl | — | isomeric form of comp 102 |
| 104 | B3 | $CH_3$ | $CH_3$ | 1-methyl-indanyl | — | isomeric form of comp 103 |
| 105 | B3 | $CH_3$ | $CH_3$ | $-CH(C_6H_5)-CH_2-C_6H_5$ | — | |
| 106 | B1 | $CH_3$ | $CH_3$ | methyladamantyl | $2,4Cl_2$ | |

TABLE 1-continued
| Co. No. | Ex No. | R¹ | R² | R¹ R² | —R³ | T | Physical data |
|---|---|---|---|---|---|---|---|
| 3 | B3 | CH₃ | CH₃ | — | 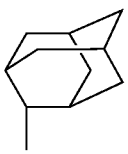 | 3,5(CH₃)₂ | |
| 107 | B1 | CH₃ | CH₃ | — | 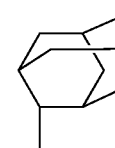 | 3-NH—CO—(CH₂)₃—Cl | |
| 108 | B6 | CH₃ | CH₃ | — | 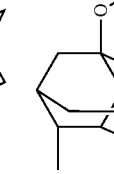 | — | |
| 109 | B6 | CH₃ | CH₃ | — | 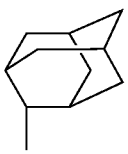 | — | |

TABLE 1-continued
| Co. No. | Ex No. | R¹ | R² | —R³ | T | Physical data |
|---|---|---|---|---|---|---|
| 110 | B3 | CH₃ | CH₃ | 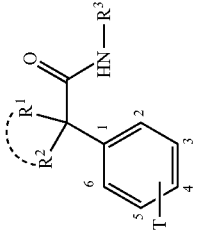 mixture of and | — | |
| 111 | B3 | CH₃ | CH₃ | 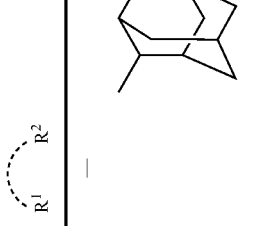 | — | |
| 12 | B9 | CH₃ | CH₃ |  | — | |
| 112 | B4 | CH₃ | CH₃ |  | 3-NH—CO—CH₃ | |

TABLE 1-continued
| Co. No. | Ex No. | R¹ | R² | —R³ | T | Physical data |
|---|---|---|---|---|---|---|
| 113 | B1 | CH₃ | CH₃ | 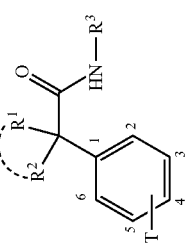 | 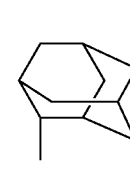 3-N-pyrrolidinone | |
| 114 | B5 | CH₃ | CH₃ | 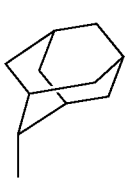 | 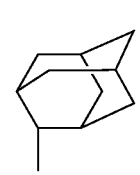 3-N-(4-methylpiperazine) | |
| 115 | B5 | CH₃ | CH₃ | 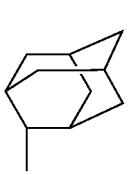 | 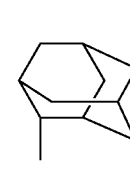 3-N-(CH₂)₂-O-CH₃ / (CH₂)₂-O-CH₃ | |
| 116 | B5 | CH₃ | CH₃ | 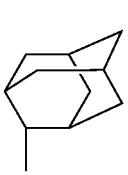 | 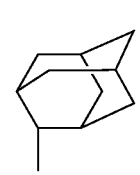 3-N-morpholine | |
| 13 | B10 | CH₃ | CH₃ | 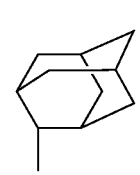 | — | |

TABLE 1-continued
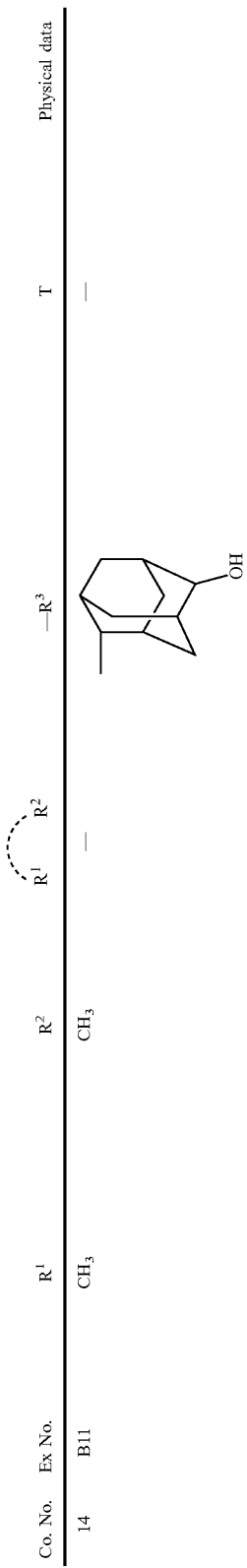
| Co. No. | Ex No. | $R^1$ | $R^2$ | $R^3$ | T | Physical data |
|---|---|---|---|---|---|---|
| 14 | B11 | CH$_3$ | CH$_3$ | 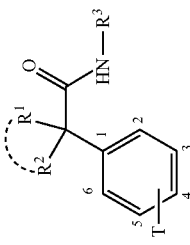 | — | |
| 117 | B6 | CH$_3$ | CH$_3$ | 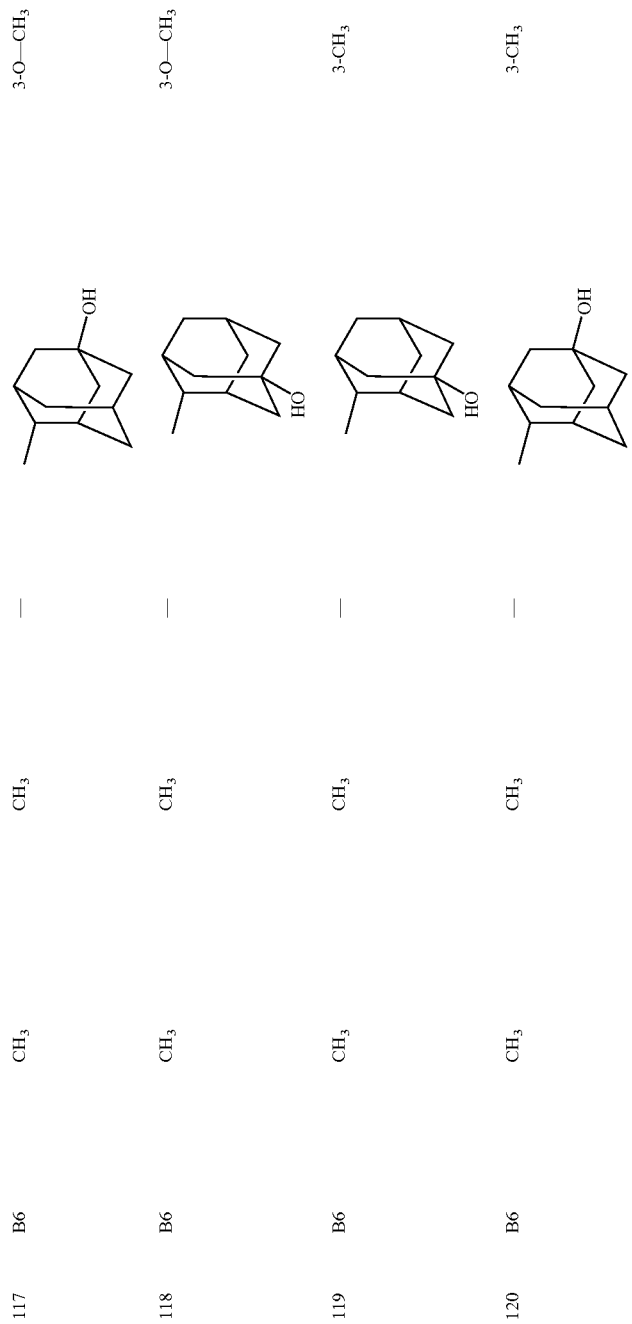 | 3-O—CH$_3$ | |
| 118 | B6 | CH$_3$ | CH$_3$ | | 3-O—CH$_3$ | |
| 119 | B6 | CH$_3$ | CH$_3$ | | 3-CH$_3$ | |
| 120 | B6 | CH$_3$ | CH$_3$ | | 3-CH$_3$ | |

TABLE 1-continued
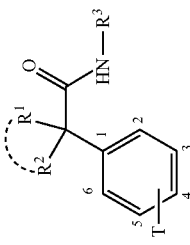
| Co. No. | Ex No. | R$^1$ | R$^2$ | R$^1$ R$^2$ | —R$^3$ | T | Physical data |
|---|---|---|---|---|---|---|---|
| 121 | B6 | CH$_3$ | CH$_3$ | — | (1-hydroxy-adamantyl) | 3,5-(—CH$_3$)$_2$ | |
| 122 | B6 | CH$_3$ | CH$_3$ | — | (1-hydroxy-adamantyl) | 3,5-(—CH$_3$)$_2$ | isomeric form of comp 121 |
| 10 | B7 | CH$_3$ | CH$_3$ | — | (fluoro-adamantyl) | — | |
| 123 | B1 | CH$_3$ | CH$_3$ | — | (adamantyl) | 3-N(CH$_3$)—CO—CH$_3$ | |
| 11 | B8 | CH$_3$ | CH$_3$ | — | (bromo-adamantyl) | 3-OH | |

TABLE 2
| Co. No. | Ex. No. | Q | n | R¹ | R² | R³ | R⁴ | Physical data |
|---|---|---|---|---|---|---|---|---|
| 124 | B3 |  | 0 | — | — | H | 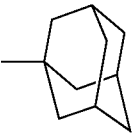 | |
| 125 | B3 | 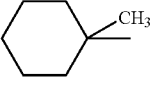 | 0 | — | — | — | 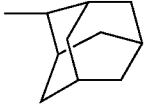 | |
| 126 | B1 | 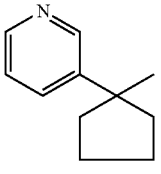 | 0 | — | — | H | 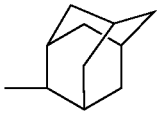 | |
| 127 | B1 | 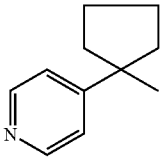 | 0 | — | — | H | 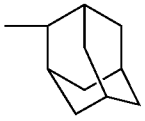 | |
| 128 | B6 | 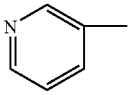 | 1 | CH₃ | CH₃ | H | 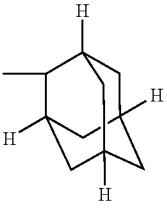 | |
| 129 | B1 | 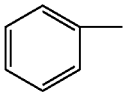 | 2 | —N(CH₃)₂ | H | H | 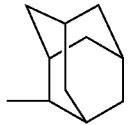 | |
| 130 | B1 | 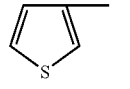 | 1 | H | H | H | 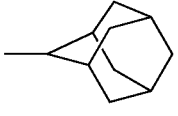 | |
| 131 | B5 | —O—CH₂—COOH | 1 | CH₃ | CH₃ | H | 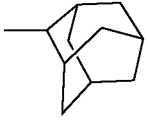 | |

TABLE 2-continued
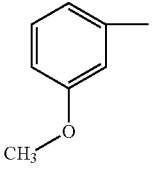
| Co. No. | Ex. No. | Q | n | R¹ | R² | R³ | R⁴ | Physical data |
|---|---|---|---|---|---|---|---|---|
| 132 | B3 | 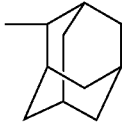 | 1 | CH₃ | CH₃ | CH₃ | 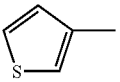 | |
| 133 | B1 | 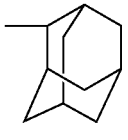 | 1 | CH₃ | CH₃ | H | 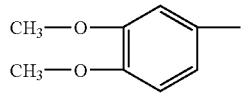 | |
| 134 | B1 | 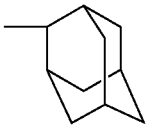 | 1 | CH₃ | CH₃ | H | 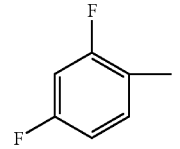 | |
| 135 | B1 | 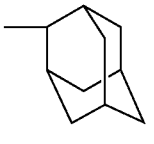 | 1 | CH₃ | CH₃ | H | 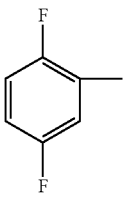 | |
| 136 | B1 | 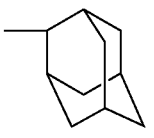 | 1 | CH₃ | CH₃ | H | 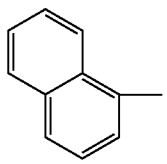 | |
| 137 | B1 | 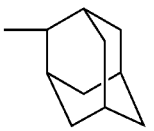 | 1 | CH₃ | CH₃ | H | 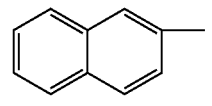 | |
| 138 | B1 | 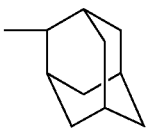 | 1 | CH₃ | CH₃ | H | 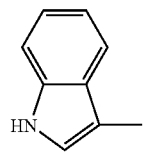 | |
| 139 | B1 | 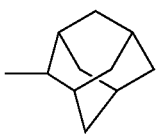 | 1 | H | H | H | | |

TABLE 2-continued

Structure: Q-(C(R¹)(R²))ₙ-C(=O)-N(R³)(R⁴)

| Co. No. | Ex. No. | Q | n | R¹ | R² | R³ | R⁴ | Physical data |
|---------|---------|---|---|-----|-----|-----|-----|---------------|
| 140 | B1 | phenyl | 2 | CH₃ | H | H | adamantyl | |
| 141 | B1 | 2,3-dimethyl-1H-indene | 0 | — | — | H | adamantyl | |
| 142 | B1 | benzo[1,3]dioxol-5-yl | 1 | CH₃ | CH₃ | H | adamantyl | |
| 143 | B1 | phenyl | 2 | CH₃ | CH₃ | H | adamantyl | |
| 144 | B1 | phenyl | 2 | CH₃ | CH₃ | H | adamantyl | |
| 145 | B1 | phenyl | 0 | — | — | H | adamantyl | |
| 146 | B1 | phenyl | 1 | =O | — | H | adamantyl | |
| 147 | B1 | (CH₃)₃C-O-C(=O)-NH-thiazol-2-yl | 1 | CH₃ | CH₃ | H | adamantyl | |
| 148 | B6 | 5-methylpyridin-3-yl | 1 | CH₃ | CH₃ | H | adamantyl | |
| 149 | B6 | 2-aminothiazol-4-yl | 1 | CH₃ | CH₃ | H | adamantyl | |

TABLE 2-continued
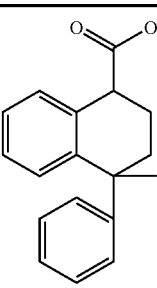
| Co. No. | Ex. No. | Q | n | R¹ | R² | R³ | R⁴ | Physical data |
|---|---|---|---|---|---|---|---|---|
| 150 | B4 | 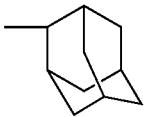 | 0 | — | — | H |  | |
| 154 | B1 | 2,5methoxy-phenyl | 1 | $CH_3$ | $CH_3$ | H | 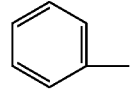 | |
TABLE 3
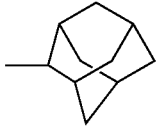
| Co. No. | Ex. No. | Q | R¹ | R² | R³ | R⁴ | Physical data |
|---|---|---|---|---|---|---|---|
| 151 | B1 | 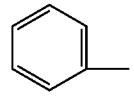 | H | $CH_3$ | H | 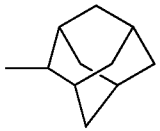 | |
| 152 | B1 | 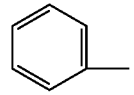 | H | H | H | 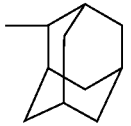 | |
| 153 | B1 | (phenyl) | $CH_3$ | H | H | (adamantyl) | |
Table 4 lists the compounds that were prepared according to one of the above Examples. The following abbreviations were used in the tables: .HCl stands for the hydrochloric acid salt.

TABLE 4
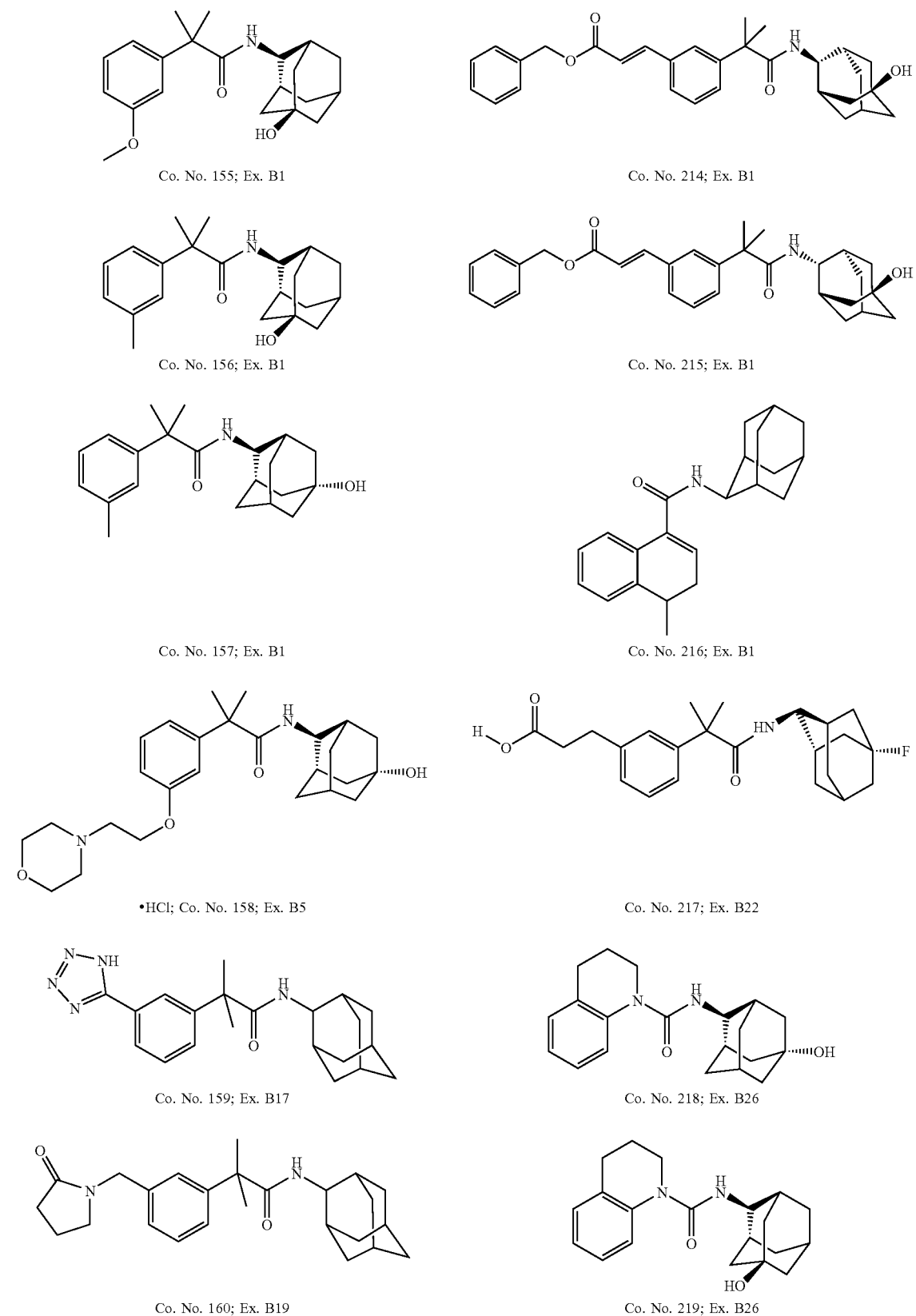

TABLE 4-continued
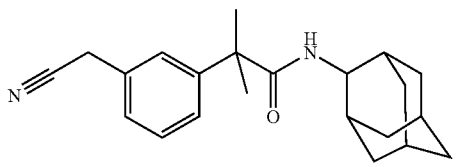
Co. No. 161; Ex. B14
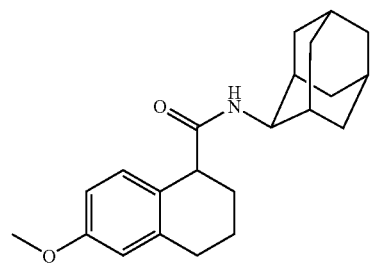
Co. No. 220; Ex. B20
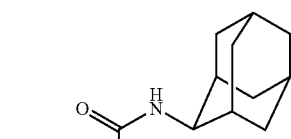
Co. No. 162; Ex. B1
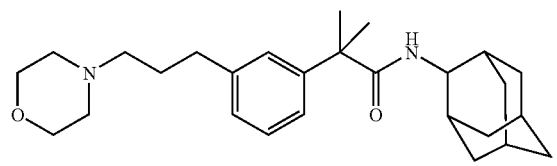
Co. No. 221; Ex. B1
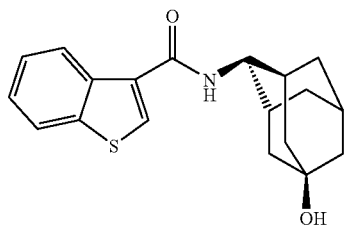
Co. No. 163; Ex. B1
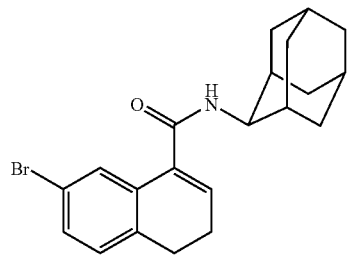
Co. No. 222; Ex. B1
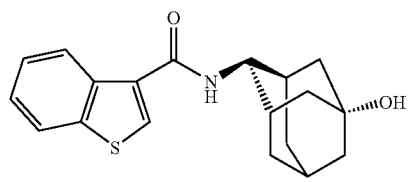
Co. No. 164; Ex. B1
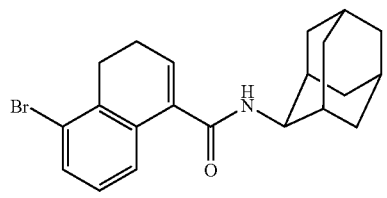
Co. No. 223; Ex. B1
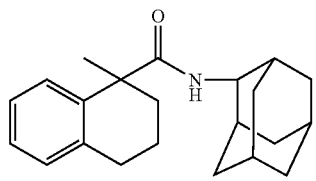
Co. No. 165; Ex. B1
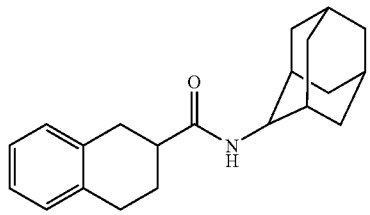
Co. No. 224; Ex. B1
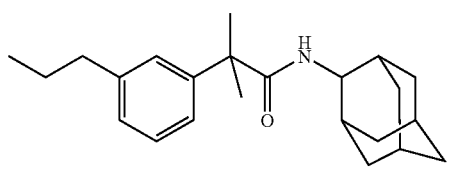
Co. No. 166; Ex. B18
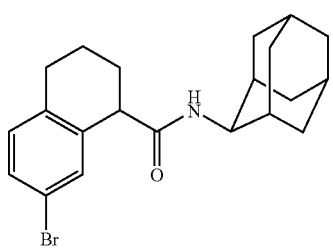
Co. No. 225; Ex. B20

TABLE 4-continued
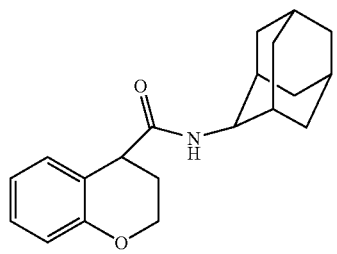
Co. No. 167; Ex. B1
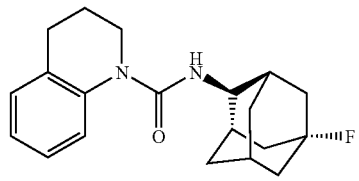
Co. No. 226; Ex. B7
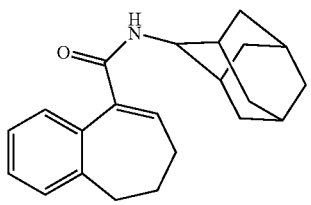
Co. No. 168; Ex. B1
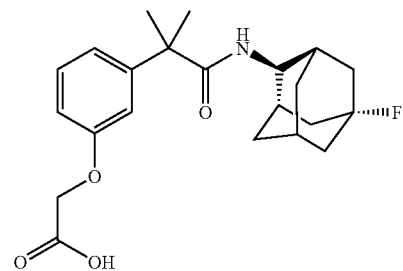
Co. No. 227; Ex. B5
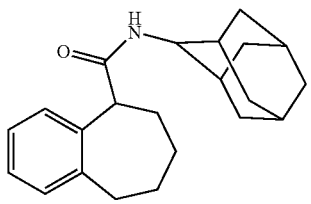
Co. No. 169; Ex. B1
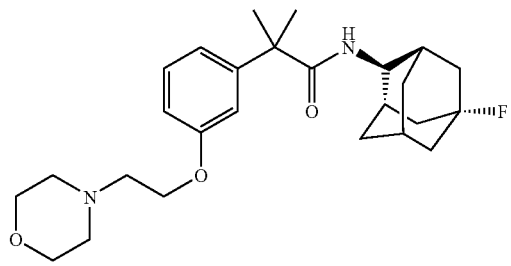
•HCl; Co. No. 228; Ex. B5
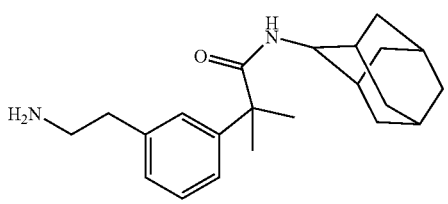
Co. No. 170; Ex. B14
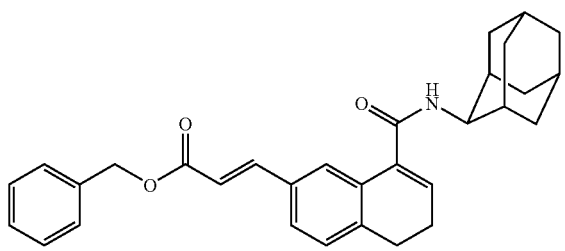
Co. No. 229; Ex. B22
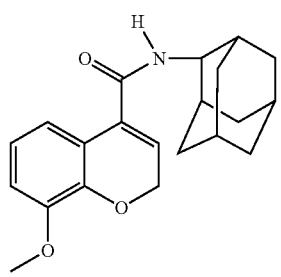
Co. No. 171; Ex. B1
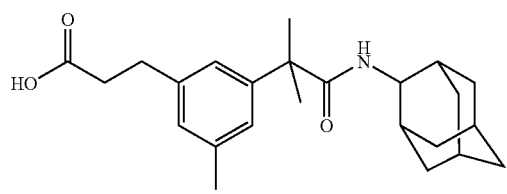
Co. No. 230; Ex. B16

TABLE 4-continued
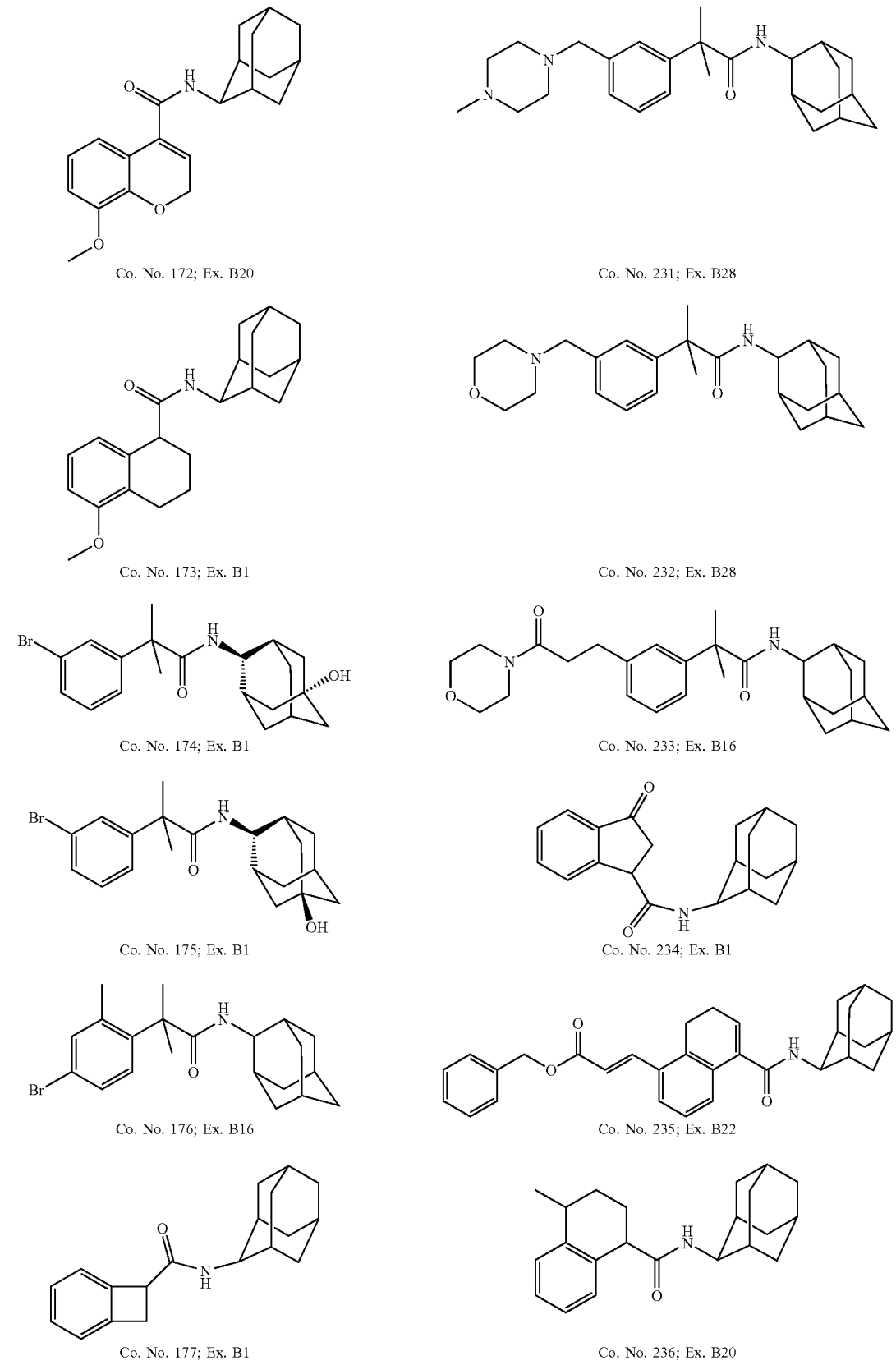
Co. No. 172; Ex. B20
Co. No. 231; Ex. B28
Co. No. 173; Ex. B1
Co. No. 232; Ex. B28
Co. No. 174; Ex. B1
Co. No. 233; Ex. B16
Co. No. 175; Ex. B1
Co. No. 234; Ex. B1
Co. No. 176; Ex. B16
Co. No. 235; Ex. B22
Co. No. 177; Ex. B1
Co. No. 236; Ex. B20

TABLE 4-continued
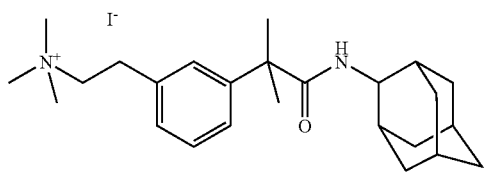
Co. No. 178; Ex. B15
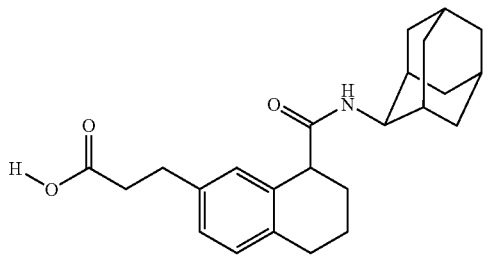
Co. No. 237; Ex. B16
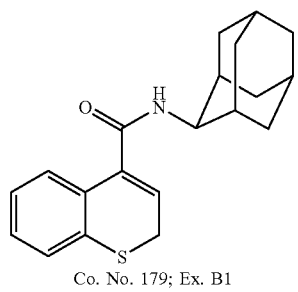
Co. No. 179; Ex. B1
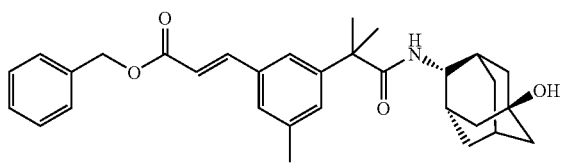
Co. No. 238; Ex. B1
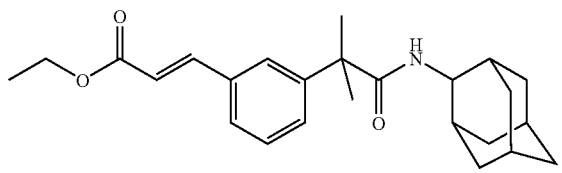
Co. No. 180; Ex. B16
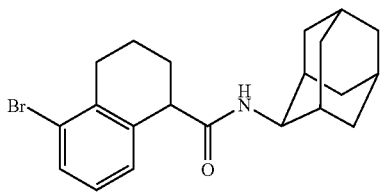
Co. No. 239; Ex. B20
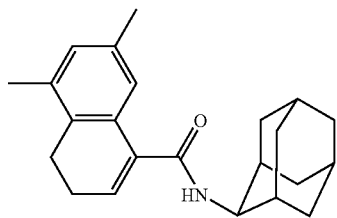
Co. No. 181; Ex. B1
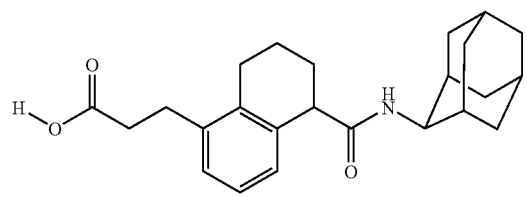
Co. No. 240; Ex. B16
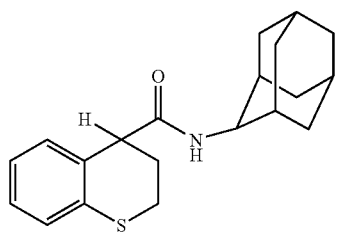
Co. No. 182; Ex. B1
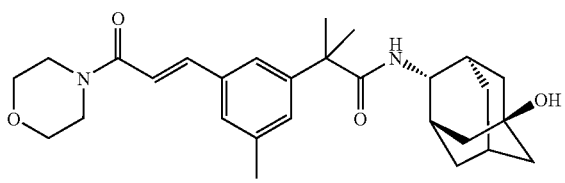
Co. No. 241; Ex. B1
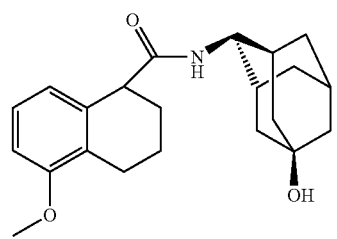
Co. No. 183; Ex. B1
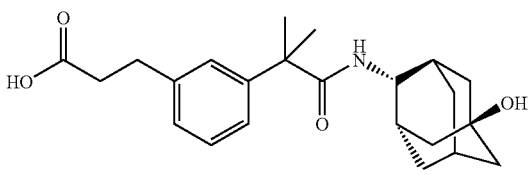
Co. No. 242; Ex. B16

TABLE 4-continued
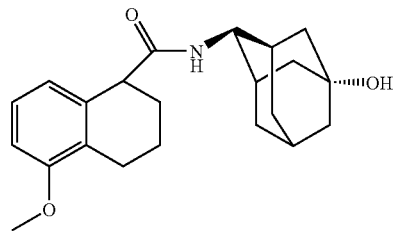
Co. No. 184; Ex. B1
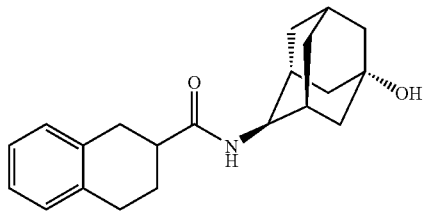
Co. No. 243; Ex. B1
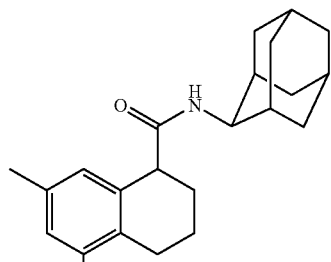
Co. No. 185; Ex. B1
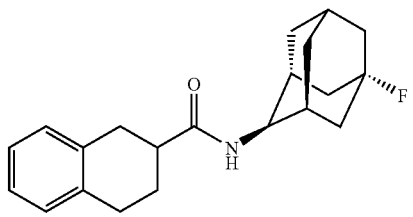
Co. No. 244; Ex. B7
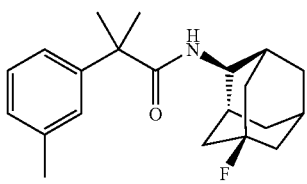
Co. No. 186; Ex. B7
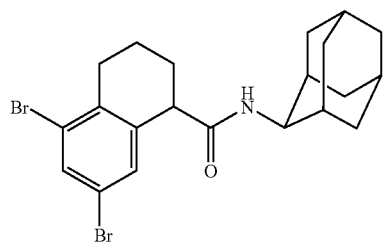
Co. No. 245; Ex. B1
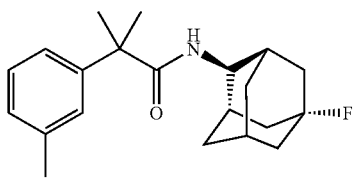
Co. No. 187; Ex. B7
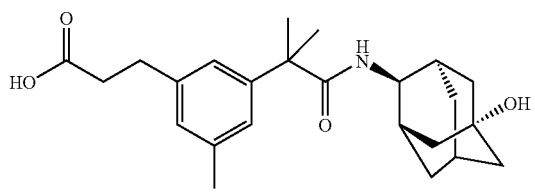
Co. No. 246; Ex. B16
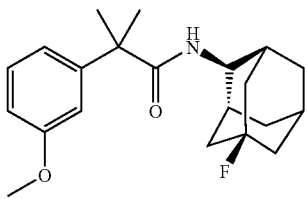
Co. No. 188; Ex. B7
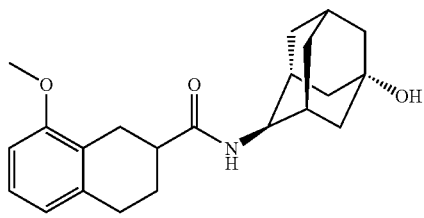
Co. No. 247; Ex. B1
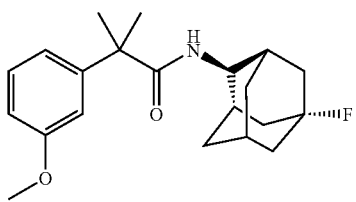
Co. No. 189; Ex. B7
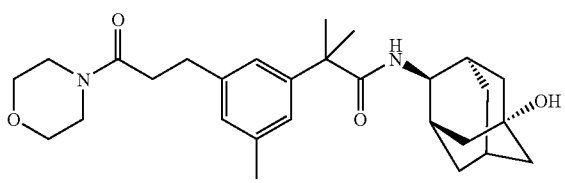
Co. No. 248; Ex. B16

TABLE 4-continued
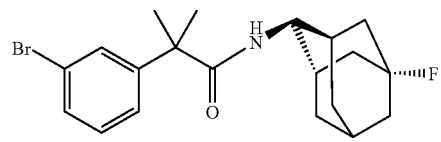
Co. No. 190; Ex. B7
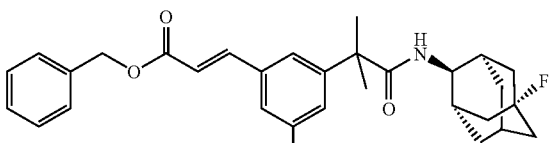
Co. No. 249; Ex. B7
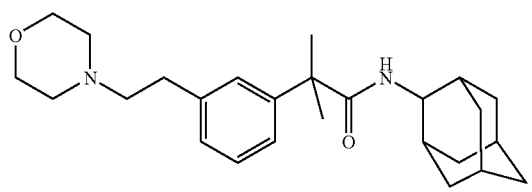
Co. No. 191; Ex. B15
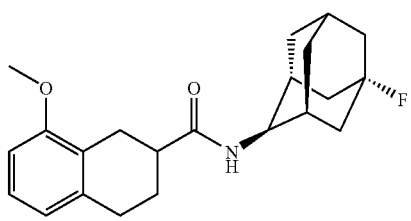
Co. No. 250; Ex. B7
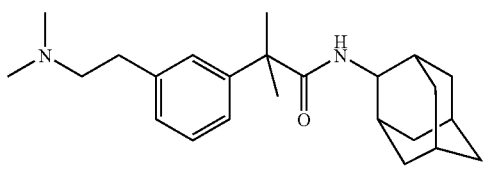
Co. No. 192; Ex. B21
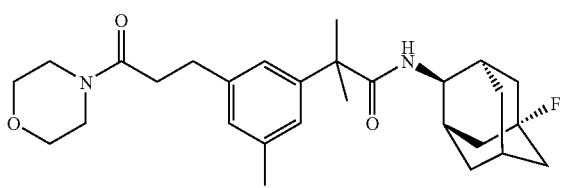
Co. No. 251; Ex. B7
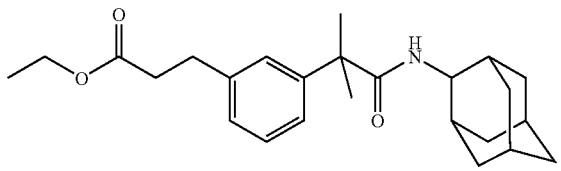
Co. No. 193; Ex. B16
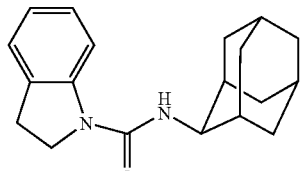
Co. No. 252; Ex. B24
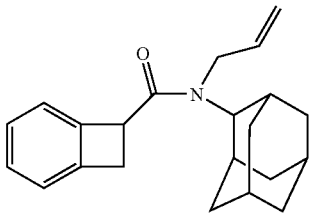
Co. No. 194; Ex. B1
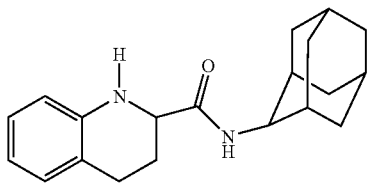
Co. No. 253; Ex. B14
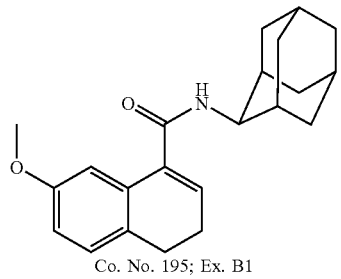
Co. No. 195; Ex. B1
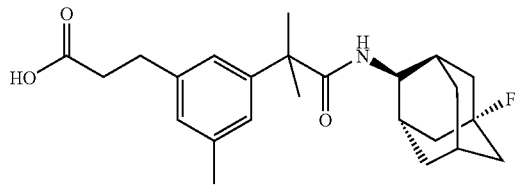
Co. No. 254; Ex. B16
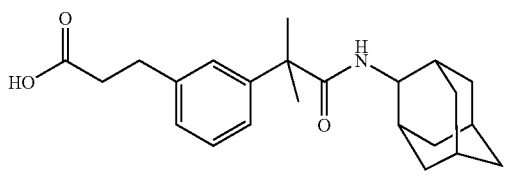
Co. No. 196; Ex. B16
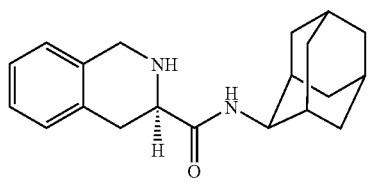
Co. No. 255; Ex. B23

TABLE 4-continued
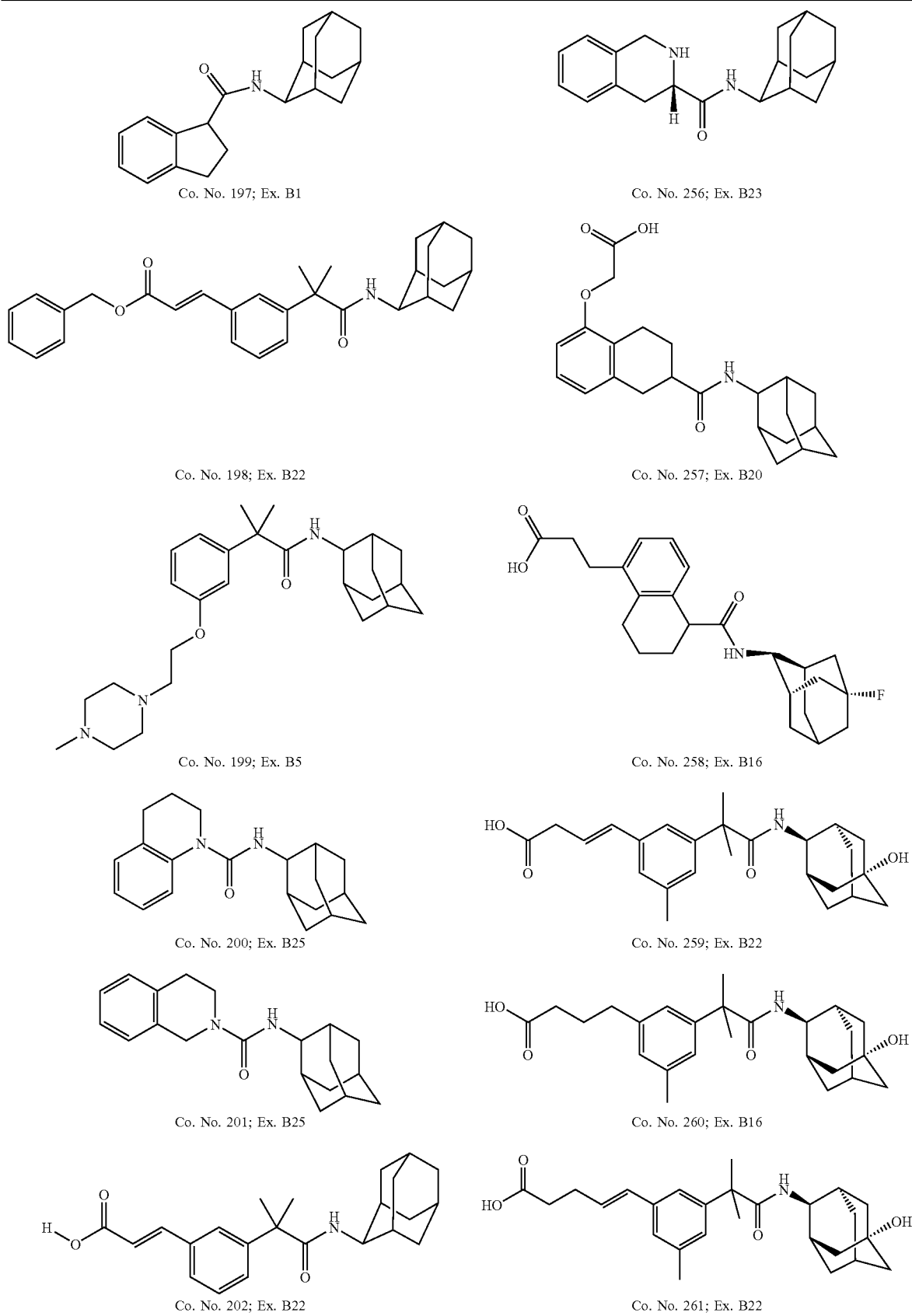

TABLE 4-continued
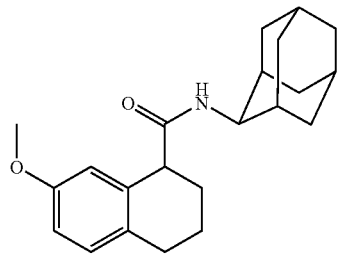
Co. No. 203; Ex. B1
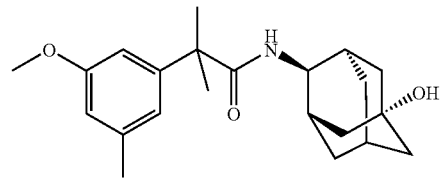
Co. No. 262; Ex. B1
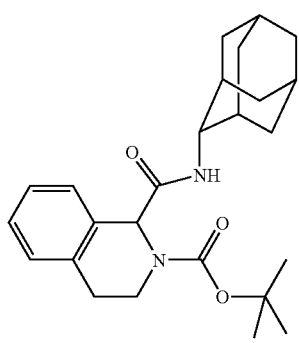
Co. No. 204; Ex. B1
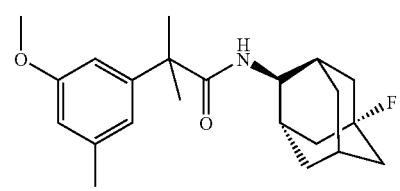
Co. No. 263; Ex. B7
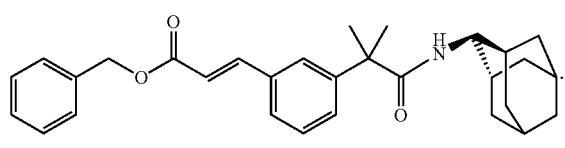
Co. No. 205; Ex. B7
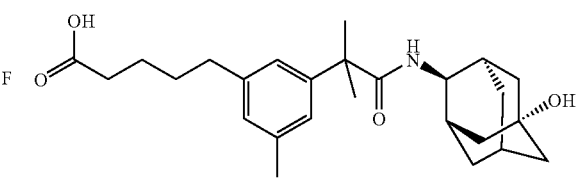
Co. No. 264; Ex. B16
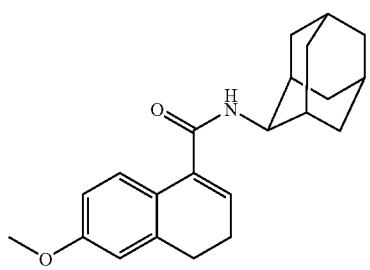
•HCl; Co. No. 206, Ex. B1
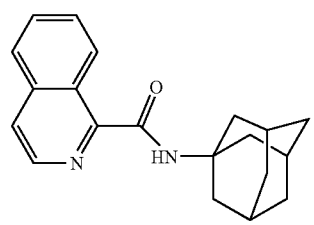
Co. No. 265; Ex. B1
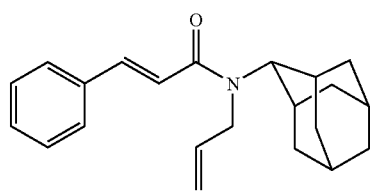
Co. No. 207, Ex. B1
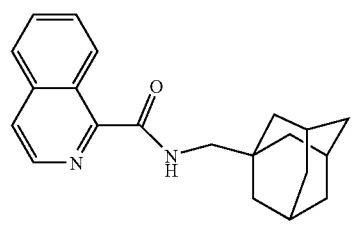
Co. No. 266; Ex. B1

TABLE 4-continued
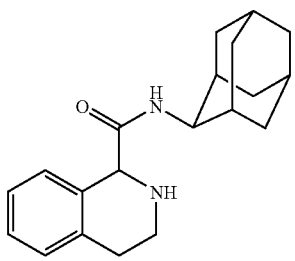
Co. No. 208; Ex. B23
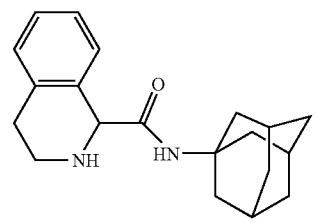
Co. No. 267; Ex. B29
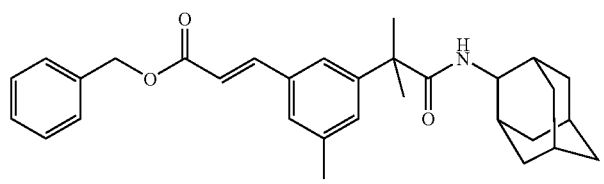
Co. No. 209; Ex. B1
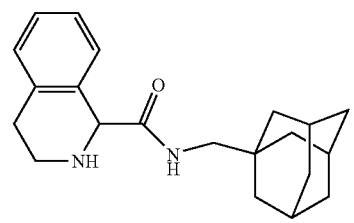
Co. No. 268; Ex. B29
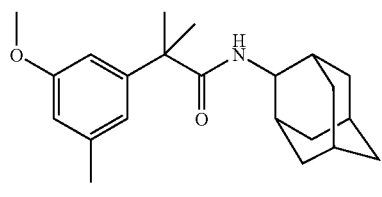
Co. No. 210; Ex. B1
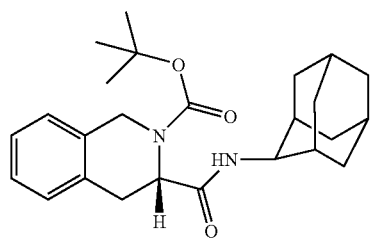
Co. No. 269; Ex. B1
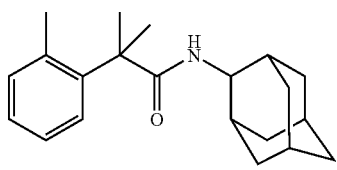
Co. No. 211; Ex. B1
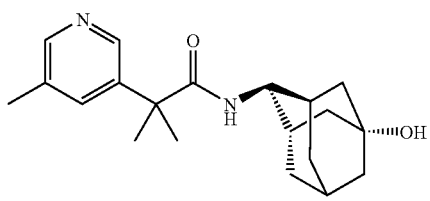
Co. No. 275; Ex. B1
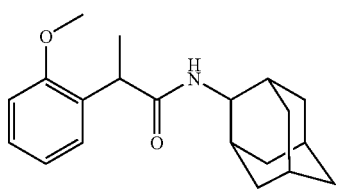
Co. No. 212; Ex. B1
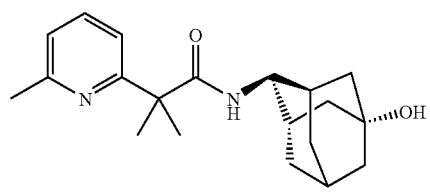
Co. No. 276; Ex. B1

TABLE 4-continued

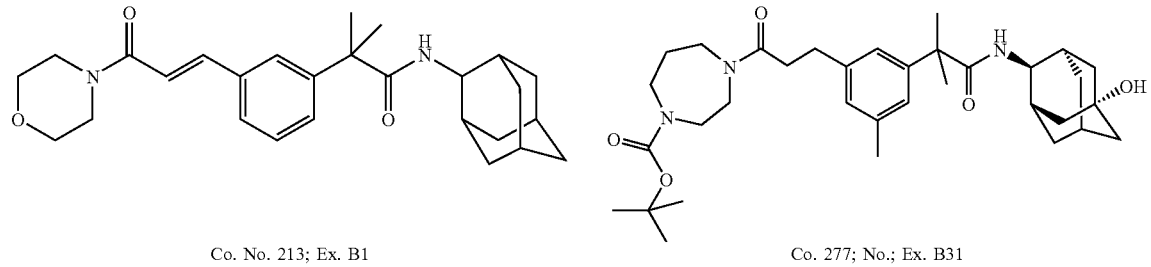

Co. No. 213; Ex. B1          Co. 277; No.; Ex. B31

| Co. No. | NMR data | melting point (° C.) |
|---|---|---|
| 155 | | 165-167 |
| 156 | (CDCl₃) 1.25-1.45(m, adamantane-H); 1.54(s, 3H, 2xMe); 1.56-1.72(m, adamantane-H); 2.10(m, adamantane-H); 2.38 (s, 3H, Me); 3.82(m, 1H, CH); 5.38 (bd, NH); 7.10(d, 1H, H-aromatic); 7.18(m, 2H-aromatic); 7.27(t, 1H-aromatic) | |
| 157 | (CDCl₃) 1.15-1.35(m, adamantane-H); 1.55(s, 3H, 2xMe); 1.65-2.05(m, adamantane-H); 2.35(s, 3H, Me); 3.92(m, 1H, CH—NH); 5.32 (bd, 1H, NH) 7.10(d, 1H, Ar—H), 7.20(m, 2H, Ar—H), 7.27(t, 1H, Ar—H) | |
| 158 | | 155-160 |
| 162 | CDCl₃; δ 1.64-2.05(m, 14H-adamantane); 4.23(d, CH); 5.30(d, CH₂); 6.14(d, NH); 6.22(t, CH); 6.86-7.48(m, 4H-aromatic) | |
| 162 | CDCl₃; δ 1.59-2.30(m, 13H-adamantane); 4.12(d, CH); 6.18(d, NH); 7.31-7.43(m, 2H-aromatic); 7.81(d, 2H-aromatic); 8.26(d, 1H-aromatic) | |
| 164 | CDCl₃; δ 1.50-2.24(m, 13H-adamantane); 4.22(d, CH); 6.15(d, NH); 7.31-7.42(m, 2H-aromatic); 7.81(d, 2H-aromatic); 8.25(d, 1H-aromatic) | |
| 165 | CDCl₃; δ 1.10-1.83(m, 14H-adamantane + 2x CH₂); 2.38(m, CH₂); 2.83(t, CH₂); 3.95(d, CH); 5.55(d, NH); 7.15-7.38(m, 4H-aromatic) | |
| 166 | CDCl₃; δ 0.92(t, CH₃); 1.22 and 1.47(2x d, 4H-adamantane); 1.58(s, 2x CH₃); 1.60-1.82(m, 10H-adamantane); 2.59(t, CH₂); 3.94(d, CH); 5.47(d, NH); 7.11-7.31(m, 4H-aromatic) | |
| 167 | CDCl₃; δ 1.22-1.91(m, 14H-adamantane); 2.15(m, $H^A$—CH₂); 2.50(m, $H^B$—CH₂); 3.63(m, CH); 4.05(m, CH₂); 4.08(d, CH); 5.96(d, NH); 6.88-7.25(m, 4H-aromatic) | |
| 168 | CDCl₃; δ 1.5-2.0(m, 16H, H-adamantane and CH₂); 2.25(quint., CH₂); 2.59(t, CH₂); 4.15(d, CH); 6,02(d, NH); 7.28-7.32(m, 4H-aromatic, CH) | |
| 169 | CDCl₃; δ 1.22-1.95(m, 18H, H-adamantane and 2xCH₂); 2.43(m, CH); 2.78(t, CH₂); 3.72(dd, CH); 4.08(d, CH); 5.72(d, NH); 7.12-7.22(m, 4H-aromatic) | |
| 171 | CDCl₃; δ 1.65-2.03(m, 14H-adamantane); 3.88(s, CH₃); 4.22(d, CH); 4.86(d, CH₂); 6.12(d, NH); 6.26(t, CH); 6.86-7.11(m, 3H-aromatic) | |
| 172 | CDCl₃; δ 1.23-1.91(m, 14H-adamantane); 2.15 and 2.53(2x m, CH₂); 3.64(m, CH); 3.91(s, CH₃); 4.08(m, CH₂); 4.42(m, CH); 6.03(d, NH); 6.74-6.94(m, 3H-aromatic) | |
| 173 | CDCl₃; δ 1.21-1.91(m, 14H-adamantane + CH₂); 2.36 and 2.56 and 2.81(3x m, 2x CH₂); 3.67(t, CH); 3.85(s, CH₃); 4.01(d, CH); 5.72(d, NH); 6.77(d, 2H-aromatic); 7.18(t, 1H-aromatic) | |
| 174 | CDCl₃; δ 1.24 and 1.40(2x d, 4H-adamantane); 1.56(s, 2x CH₃); 1.68-2.00(m, 9H-adamantane); 3.92(d, CH); 5.45(d, NH); 7.25-7.55(m, 4H-aromatic) | |
| 175 | CDCl₃; δ 1.30-1.74(m, 13H-adamantane); 1.54(s, 2x CH₃); 3.75(dt, CH); 5.35(d, NH); 7.28-7.52(m, 4H-aromatic) | |
| 176 | CDCl₃: 1.51-1.88(m, 15H-adamantane); 2.16(s, CH₃); 3.87(dt, CH); 5.12(d, NH); 6.11(d, NH); 7.27-7.36(m, 3H-aromatic). | |
| 177 | CDCl₃; δ 1.44-1.96(m, 14H-adamantane); 3.30(dd, $H^A$—CH₂); 3.61(dd, $H^B$—CH₂); 4.05(d, CH); 4.23(dd, CH); 6.09(m, NH); 7.14-7.31(m, 4H-aromatic) | |
| 178 | Aceton d-6; δ 1.38-1.74(m, 14H-adamantane); 1.62(s, 2x CH₃); 3.15(m, CH₂); 3.48(s, 3x CH₃); 3.94(m, CH and CH₂); 5.68(d, NH); 7.28-7.39(m, 4H-aromatic) | |
| 179 | CDCl₃; δ 1.61-2.4(m, 14H-adamantane); 3.39(d, CH₂); 4.22(dt, CH); 6.03(m, NH); 6.51(t, CH); 7.16(m, 2H-aromatic); 7.34 and 7.50(2x m, 2H-aromatic) | |
| 180 | CDCl₃; δ 1.27-1.72(m, 14H-adamantane); 1.59(s, 2x CH₃); 3.97(d, CH); 5.46(d, NH); 6.35(d, CH); 7.40-7.55(m, 4H-aromatic); 7.59(d, CH) | |
| 181 | CDCl₃; δ 1.64-2.30(m, 14H-adamantane); 2.27(s, 2x CH₃); 2.34(m, CH₂); 2.69(t, CH₂); 4.23(d, CH); 6.12(d, NH); 6.49(t, CH); 6.91 and 7.12(2x s, 2H-aromatic) | |
| 182 | CDCl₃; δ 1.17-1.85(m, 14H-adamantane); 1.99(m, $H^A$—CH₂); 2.88(m, $H^B$—CH₂ and $H^A$—CH₂); 3.08(m, $H^B$—CH₂); 3.75(t, CH); 4.00(d, CH); 6.72(d, NH); 7.03-7.21(m, 4H-aromatic) | |
| 183 | CDCl₃; δ 1.22-2.15(m, 14H-adamantane + CH₂); 2.32(m, $H^A$—CH₂); 2.55(m, $H^B$—CH₂ and $H^A$—CH₂); 2.70(m, $H^B$—CH₂); 3.65(t, CH); 3.83(s, CH₃); 3.89(dt, CH); 5.62(d, NH); 6.75(t, 2H-aromatic); 7.17(t, H-aromatic) | |
| 184 | CDCl₃; δ 1.15- 2.05(m, 14H-adamantane + CH₂); 2.36(m, $H^A$—CH₂); 2.56(m, $H^B$—CH₂); 2.70(m, CH₂); 3.66t, CH); 3.84(s, CH₃); 3.98(d, CH); 5.59(d, NH); 6.75(t, 2H-aromatic); 7.18(t, H-aromatic) | |
| 185 | CDCl₃; δ 1.20-1.92(m, 14H-adamantane + CH₂); 2.21 and 2.27(2x s, 2x CH₃); 2.34(m, $H^A$—CH₂); 2.54(m, $H^B$—CH₂ and $H^A$—CH₂); 2.69(m, $H^B$—CH₂); 4.02(dt, CH); 5.72(d, NH); 6.81 and 6.93(2x s, 2H-aromatic) | |
| 186 | CDCl₃; δ 1.35-1.45(m, adamantane-H); 1.57(s, 3H, 2xMe); 1.60-1.82(m, adamantane-H); 2.15(m, adamantane-H); 2.38 (s, 3H, Me); 3.82(m, 1H, CH—NH); 5.32 (bd, 1H, NH); 7.10(d, 1H, Ar—H); 7.18(m, 2H, Ar—H); 7.27(t, 1H, Ar—H) | |
| 187 | | 115-117 |
| 188 | | 110-112 |
| 189 | | 105-107 |
| 190 | CDCl₃; δ 1.19-2.13(m, 13H-adamantane); 1.54(s, 2x CH₃); 3.95(d, CH); 5.37(d, NH); 7.22-7.54(m, 4H-aromatic) | |
| 194 | CDCl₃; δ 1.60-2.29(m, 14H-adamantane); 3.41(dd, $H^A$—CH₂); 3.55(dd, $H^A$—CH₂); 4.23(s, CH); 4.26(m, $H^B$—CH₂); 4.41(m, $H^B$—CH₂); 4.48(dd, CH); 5.19 (brd, =CH2); 5.93(m, =CH); 7.06-7.26(m, 4H-aromatic) | |
| 195 | CDCl₃; δ 1.65-2.06(m, 14H-adamantane); 2.35(m, CH₂); 2.72(t, CH₂); 3.77(s, CH₃); 4.24(d, CH); 6.15(d, NH); 6.54(t, CH); 6.75(dd, H-aromatic); 7.18(m, 2H-aromatic) | |
| 196 | CDCl₃; δ 1.20-1.72(m, 14H-adamantane); 1.58(s, 2x CH₃); 2.67 and 2.97(2xt, 2x CH₂); 3.95(d, CH); 5.48(d, NH); 7.14-7.34(m, 4H-aromatic); | |

TABLE 4-continued

| | | |
|---|---|---|
| 197 | CDCl₃; δ 1.40-1.94(m, 14H-adamantane); 2.30-2.53(m, CH₂); 2.87-3.09(m, CH₂); 3.94(dd, CH); 4.05(d, CH); 5.71(d, NH); 7.20-7.32(m, 4H-aromatic) | |
| 198 | CDCl₃; δ 1.28 and 1.49(2x d, 4H-adamantane); 1.58(s, 2x CH₃); 1.62-1.82(m, 10H-adamantane); 3.96(d, CH); 5.26(s, CH₂); 5.44(d, NH); 6.50(d, CH); 7.33-7.54(m, 9H-aromatic); 7.72(d, CH) | |
| 199 | | 165-170 |
| 200 | | 163-165 |
| 201 | | 145-147 |
| 202 | CDCl₃; δ 1.29 and 1.51(2x d, 4H-adamantane); 1.61(s, 2x CH₃); 1.65-1.84(m, 10H-adamantane); 3.98(d, CH); 5.49(d, NH); 6.48(d, CH); 7.40-7.58(m, 9H-aromatic); 7.80(d, CH) | |
| 203 | CDCl₃; δ 1.26-1.88(m, 14H-adamantane + CH₂); 1.88-1.98(m, CH₂); 2.32 and 2.75(2x m, 2x CH₂); 3.69(t, CH); 3.77(s, CH₃); 4.03(d, CH); 5.68(d, NH); 6.66(d, H-aromatic); 6.80(dd, H-aromatic); 7.09(d, 1H-aromatic) | |
| 204 | CDCl₃; δ 1.50-1.95(m, 14H-adamantane, 3x CH₃); 2.88(t, CH₂); 3.58 and 3.81(m, CH₂); 4.00(d, CH); 5.49(s, CH); 7.10-7.28(m, 4H-aromatic) | |
| 205 | CDCl₃; δ 1.19 and 1.37(2x d, 4H-adamantane); 1.50(s, 2x CH₃); 1.80-2.1(m, 9H-adamantane); 3.94(d, CH); 5.25(d, NH); 5.26(s, CH₂); 6.51(d, CH); 7.35-7.54(m, 9H-aromatic); 7.72(d, CH) | |
| 206 | CDCl₃; δ 1.63-2.05(m, 14H-adamantane); 2.34(m, CH₂); 2.78(t, CH₂); 3.81(s, CH₃); 4.23(d, CH); 6.14(d, NH); 6.38(t, CH); 6.73(m, 2H-aromatic); 7.39(m, 1H-aromatic) | |
| 207 | CDCl₃; δ 1.63-2.28(m, 14H-adamantane); 4.30(dd, CH₂); 4.34(s, CH); 5.21(m, CH₂); 5.95(m, =CH); 6.85(d, CH); 7.30-7.52(m, 5H-aromatic); 7.68(d, CH) | |
| 208 | CDCl₃; δ 1.50-1.92(m, 14H-adamantane); 2.75-2.92(m, CH₂); 3.09-3.21(m, CH₂); 4.00(d, CH); 4.63(s, CH); 7.05-7.22(m, 3H-aromatic); 7.53(m, 1H-aromatic); 7.59(d, NH) | |
| 209 | CDCl₃; δ 1.28 and 1.51(2x d, 4H-adamantane); 1.57(s, 2x CH₃); 1.66 and 1.78(2xm, 9H-adamantane); 2.36(s, CH₃); 3.96(d, CH); 5.25(s, CH₂); 5.46(d, NH); 6.48(d, CH); 7.20-7.42(m, 9H-aromatic); 7.70(d, CH) | |
| 210 | CDCl₃; δ 1.31 and 1.50(2x d, 4H-adamantane); 1.55(s, 2x CH₃); 1.67 and 1.78(2xm, 10H-adamantane); 2.33(s, CH₃); 3.79(s, CH₃); 3.95(d, CH); 5.55(d, NH); 6.62; 6.73 and 6.79(3xs, 3H-aromatic) | |
| 211 | CDCl₃; δ 1.24 and 1.36(2x d, 4H-adamantane); 1.56(s, 2x CH₃); 1.60 and 1.82(2xm, 10H-adamantane); 2.28(s, CH₃); 4.01(d, CH); 5.49(d, NH); 7.15-7.26(m, 3H-aromatic); 7.39-7.48(s, 1H-aromatic) | |
| 212 | CDCl₃; δ 1.32-1.85(m, 14H-adamantane); 1.50(d, CH₃); 3.88(s, CH₃); 3.96(d, CH); 4.05(q, CH); 6.12(d, NH); 6.88-7.10 and 7.22-7.34(2xm, 4H-aromatic) | |
| 213 | CDCl₃; δ 1.26 and 1.43(2x d, 4H-adamantane); 1.60(s, 2x CH₃); 1.65 and 1.79(2xm, 10H-adamantane); 3.65-3.78(m, 4x CH₂); 3.96(d, CH); 5.47(d, NH); 6.83(d, CH); 7.38-7.52(m, 3H-aromatic); 7.70(d, CH) | |
| 214 | CDCl₃; δ 1.28-2.18(m, 13H-adamantane); 1.58(s, 2xCH₃); 3.36(dt, CH); 5.27(s, CH₂); 5.36(d, NH); 6.50(d, CH); 7.34-7.52(m, 9H-aromatic); 7.70(d, CH) | |
| 215 | CDCl₃; δ 1.18-2.10(m, 13H-adamantane); 1.58(s, 2xCH₃); 3.93(dt, CH); 5.25(s, CH₂); 5.31(d, NH); 6.50(d, CH); 7.34-7.54(m, 9H-aromatic); 7.73(d, CH) | |
| 216 | CDCl₃; δ 1.28(d, CH₃); 1.63-2.06(m, 14H-adamantane); 2.19(m, Hᴬ—CH₂); 2.50(m, Hᴮ—CH₂); 2.93(m CH); 4.24(d, CH); 6.13(d, NH); 6.46(t, CH); 7.18-7.47(m, 4H-aromatic) | |
| 217 | CDCl₃; δ 1.15 and 1.36(2x d, 4H-adamantane); 1.59(s, 2x CH₃); 1.80-2.10(m, 10H-adamantane); 2.67(t, CH₂); 2.97(t, CH₂); 3.94(d, CH); 5.39(d, NH); 7.12-7.40(m, 4H-aromatic) | |
| 218 | | 170-172 |
| 219 | | 185-188 |
| 220 | CDCl₃; δ 1.21-1.86(m, 14H-adamantane, CH₂); 1.92(m, Hᴬ—CH₂); 2.34(m, Hᴮ—CH₂); 2.80(m, CH₂); 3.63(d, CH); 5.68(d, NH); 6.70-6.78(m, 2H-aromatic); 7.06(d, H-aromatic) | |
| 221 | CDCl₃; δ 1.18 and 1.40(2x d, 4H-adamantane); 1.50(s, 2x CH₃); 1.58 and 1.72(2xm, 10H-adamantane); 2.28(t, 2xCH₂); 2.35(m, 2xCH₂); 2.58(t, CH₂); 3.65(t, 2xCH₂); 3.88(dt, CH); 5.38(d, NH); 7.05-7.25(m, 4H-aromatic) | |
| 222 | CDCl₃; δ 1.66-2.06(m, 14H-adamantane); 2.38(m, CH₂); 2.74(t, CH₂); 4.22(d, CH); 6.11(d, NH); 6.52(t, CH); 7.04(d, H-aromatic); 7.30(d, H-aromatic); 7.65(s, H-aromatic) | |
| 223 | CDCl₃; δ 1.64-2.05(m, 14H-adamantane); 2.40(m, CH₂); 2.94(t, CH₂); 4.22(d, CH); 6.11(d, NH); 6.49(t, CH); 7.07(t, H-aromatic); 7.42(m, 2H-aromatic) | |
| 224 | CDCl₃; δ 1.59-1.95(m, 14H-adamantane); 1.98 and 2.10(2x m, CH₂); 2.55(m CH); 2.86-3.08(m, 2x CH₂); 4.08(dt, CH); 5.78(d, NH); 7.08-7.15(m, 4H-aromatic) | |
| 225 | CDCl₃; δ 1.29-2.00(m, 14H-adamantane, CH₂); 2.30(m, CH₂); 2.76(m, CH₂); 3.63(t, CH); 4.02(d, CH); 5.60(d, NH); 7.04(d, H-aromatic); 7.33(m, 2H-aromatic) | |
| 226 | | 182-184 |
| 227 | | 210-215 |
| 228 | | 208-210 |
| 229 | CDCl₃; δ 1.60-2.08(m, 14H-adamantane); 2.39(m, CH₂); 2.81(t, CH₂); 4.24(d, CH); 5.22(s, CH₂); 6.14(d, NH); 6.44(d, CH); 6.53(t, CH); 7.16-7.43(m, 9H-aromatic) | |
| 230 | CDCl₃; δ 1.28 and 1.50(2x d, 4H-adamantane); 1.55(s, 2x CH₃); 1.66 and 1.78(2xm, 10H-adamantane); 2.32(s, CH₃); 2.63(t, CH₂); 2.93(t, CH₂); 3.94(dt, CH); 5.53(d, NH); 6.90-7.10(m, 3H-aromatic) | |
| 231 | CDCl₃; δ 1.22 and 1.46(2x d, 4H-adamantane); 1.58(s, 2x CH₃); 1.64 and 1.76(2xm, 10H-adamantane); 2.30(s, CH₃); 2.40-2.54(m, 4xCH₂); 3.51(s, CH₂); 3.94(d, CH); 5.44(d, NH); 7.23-7.36(m, 4H-aromatic) | |
| 232 | CDCl₃; δ 1.22 and 1.48(2x d, 4H-adamantane); 1.60(s, 2x CH₃); 1.64-1.76(m, 10H-adamantane); 2.42(m, 2xCH₂); 3.51(s, CH₂); 3.70(m, 2xCH₂); 3.94(d, CH); 5.45(d, NH); 7.22-7.38(m, 4H-aromatic) | |
| 234 | CDCl₃; δ 1.62-1.99(m, 14H-adamantane, CH₂); 2.91(dd, Hᴬ—CH₂); 3.30(dd, Hᴮ—CH₂); 4.05-4.13(m, 2x CH); 6.06(d, NH); 7.44-7.80(m, 4H-aromatic) | |
| 235 | CDCl₃; δ 1.64-2.07(m, 14H-adamantane); 2.39(m, CH₂); 2.91(t, CH₂); 4.23(d, CH); 5.27(s, CH₂); 6.12(d, NH); 6.39(d, CH); 6.52(t, CH); 7.19-7.50(m, 9H-aromatic); 8.08(d, CH) | |
| 238 | CDCl₃; δ 1.18-2.02(m, 13H-adamantane); 1.56(s, 2x CH₃); 2.38(s, CH₃); 3.93(dt, CH); 5.25(s, CH₂); 5.32(d, NH); 6.49(d, CH); 7.20-7.42(m, 8H-aromatic); 7.69(d, CH) | |
| 239 | CDCl₃; δ 1.23-1.93(m, 14H-adamantane, CH₂); 2.34(m, CH₂); 2.61-2.95(m, CH₂); 3.68(t, CH); 4.03(d, CH); 5.60(d, NH); 7.10(m, 2H-aromatic); 7.51(m, 1H-aromatic) | |
| 240 | CDCl₃; δ 1.19-1.97(m, 14H-adamantane, CH₂); 2.38(m, CH₂); 2.58-3.00(m, 4xCH₂); 3.70(t, CH); 4.01(d, CH); 5.17(d, NH); 7.01-7.18(m, 3H-aromatic) | |
| 241 | CDCl₃; δ 1.20-2.03(m, 13H-adamantane); 1.58(s, 2x CH₃); 2.39(s, CH₃); 3.67-3.76(m, 4xCH₂); 3.93(dt, CH); 5.33(d, NH); 6.82(d, CH); 7.19; 7.26 and 7.32(3x s, 3H-aromatic); 7.66(d, CH) | |
| 243 | CDCl₃; δ 1.45-2.15(m, 13H-adamantane, CH₂); 2.58(m, CH); 2.79-3.17(m, 2xCH₂); 4.03(d, CH); 5.75(d, NH); 6.82(d, CH); 7.05-7.15(m, 4H-aromatic) | |

TABLE 4-continued

| | | |
|---|---|---|
| 245 | CDCl₃; δ 1.36-1.93(m, 14H-adamantane, CH₂); 2.26(m, CH2); 2.59-2.86(m, CH₂); 3.62(t, CH); 4.04(d, CH); 5.61(d, NH); 7.38 and 7.67(2x d, 2H-aromatic) | |
| 246 | CDCl₃; δ 1.18 and 1.36(2x d, 4H-adamantane); 1.53(s, 2x CH₃); 1.69 and 1.72 and 1.99(3xm, 9H-adamantane); 2.33(s, CH₃); 2.64(t, CH₂); 2.92(t, CH₂); 3.91(d, CH); 5.36(d, NH); 6.95-7.05(m, 3H-aromatic) | |
| 248 | CDCl₃; δ 1.21-2.02(m, 13H-adamantane, CH₂); 1.54(s, 2x CH₃); 2.32(s, CH₃); 2.59(t, CH₂); 2.93(t, CH₂); 3.39(t, CH₂); 3.58(t, CH₂); 3.65(m, 2xCH₂); 3.92(d, CH); 5.36(d, NH); 6.95-7.05(m, 3H-aromatic) | |
| 249 | CDCl₃; δ 1.18 and 1.38(2x d, 4H-adamantane); 1.56(s, 2x CH₃); 1.58-2.10(m, 9H-adamantane); 2.37(s, CH₃); 3.94(dt, CH); 5.25(s, CH₂); 5.28(d, NH); 6.48(d, CH); 7.20-7.44(m, 8H-aromatic); 7.70(d, CH) | |
| 252 | CDCl₃; δ 1.65-2.01(m, 14H-adamantane); 3.19(t, CH₂); 3.96(t, CH₂); 4.08(d, CH); 4.93(d, NH); 6.90(t, 1H-aromatic); 7.15(m, 2H-aromatic); 7.85(d, 1H-aromatic) | |
| 253 | CDCl₃; δ 1.45-1.90(m, 14H-adamantane); 1.95(m, H^A—CH₂); 2.31(m, H^B—CH₂); 2.60(m, H^A—CH₂); 2.75(m, H^B—CH₂); 3.90(q, CH); 4.05(dt, CH); 4.16(d, NH); 6.70(m, 2H-aromatic); 7.02(m, 2H-aromatic); 7.22(d, NH) | |
| 254 | CDCl₃; δ 1.18 and 1.38(2x d, 4H-adamantane); 1.55(s, 2x CH₃); 1.85-2.18(m, 9H-adamantane); 2.32(s, CH₃); 2.65(t, CH₂); 2.93(t, CH₂); 3.92(dt, CH); 5.32(d, NH); 6.95-7.15(m, 3H-aromatic) | |
| 255 | CDCl₃; δ 1.59-1.95(m, 14H-adamantane); 2.83(dd, H^A—CH₂); 3.26(dd, H^B—CH₂); 3.57(m, H^A—CH₂); 3.97-4.08(m, 3H, 2xCH, H^B—CH₂); m, 2H-aromatic); 7.05-7.18(m, 4H-aromatic); 7.68(d, NH) | |
| 256 | CDCl₃; δ 1.59-1.95(m, 14H-adamantane); 2.83(dd, H^A—CH₂); 3.26(dd, H^B—CH₂); 3.58(m, H^A—CH₂); 3.97-4.08(m, 3H, 2xCH, H^B—CH₂); m, 2H-aromatic); 7.05-7.18(m, 4H-aromatic); 7.68(d, NH) | |
| 257 | | 215-220 |
| 258 | LCMS M⁺ = 417, Retention time 4.01, 97% P | |
| 259 | CDCl₃; δ 1.20 and 1.36(2x d, 4H-adamantane); 1.55(s, 2x CH₃); 1.69; 1.83 and 1.98(3x d, 9H-adamantane); 2.34(s, CH₃); 3.30(d, CH₂); 3.93(dt, CH); 5.38(d, NH); 6.28(d, CH); 6.48(d, CH); 7.07, 7.12 and 7.18(3x s, 3H-aromatic) | |
| 260 | CDCl₃; δ 1.14-2.02(m, 13H-adamantane, CH₂); 1.56(s, 2x CH₃); 2.33(s, CH₃); 2.35(t, CH₂); 2.63(t, CH₂); 3.92(d, CH); 5.38(d, NH); 6.92, 6.98 and 7.04(3x s, 3H-aromatic) | |
| 262 | CDCl₃; δ 1.22-2.02(m, 13H-adamantane, CH₂); 1.53(s, 2x CH₃); 2.33(s, CH₃); 3.79(s, CH₃); 3.92(d, CH); 5.42(d, NH); 6.63, 6.74 and 6.78(3x s, 3H-aromatic) | |
| 263 | CDCl₃; δ 1.22 and 1.39(2x d, 4H-adamantane); 1.54(s, 2x CH₃); 1.83-2.19(m, 9H-adamantane); 2.32(s, CH₃); 3.78(s, CH₃); 3.92(d, CH); 5.36(d, NH); 6.64, 6.74 and 6.78(3x s, 3H-aromatic) | |
| 264 | CDCl₃; δ 1.14-1.38(m, 4H-adamantane); 1.55(s, 2x CH₃); 1.62-1.99(m, 9H-adamantane, 2xCH₂); 2.32(s, CH₃); 2.36(t, CH₂); 2.60(t, CH₂); 3.90(d, CH); 5.40(d, NH); 6.85-7.10(m, 3H-aromatic) | |
| 265 | CDCl₃; δ 1.61-2.22(m, 14H-adamantane); 7.60-8.00(m, 5H-aromatic); 8.42(d, H-arom.) | |
| 266 | CDCl₃; δ 1.58-2.04(m, 14H-adamantane); 3.21(d, CH₂); 5.39(d, NH); 7.63-7.87(m, 5H-aromatic); 8.46(d, H-arom.) | |
| 267 | CDCl₃; δ 1.64 and 1.97 and 2.05(2x brs, 14H-adamantane); 2.70-2.89(m, CH₂); 3.09(t, CH₂); 4.40(s, CH); 6.93-7.19(m, 4H-aromatic); 7.50(m, NH) | |
| 268 | CDCl₃; δ 1.39-1.97(m, 14H-adamantane); 2.73-2.97(m, 2xCH₂); 3.11(m, CH₂); 4.59(s, CH); 7.07-7.54(m, 4H-aromatic) | |
| 269 | LCMS retention time: 6.27 min., M⁺ = 411; 100% | |
| 275 | CDCl₃; 1.23-1.46(m, 5H-adamantane), 1.60(s, 2x CH₃), 1.72(m, 4H-adamantane), 1.85(d, 2H-adamantane), 2.03 (brs, 3H-adamantane); 2.35(s, CH₃); 3.96(d, CH); 5.48(d, NH); 7.50, 8.38 and 3.48(3xd, 3H-aromatic) | |
| 276 | CDCl₃; 1.43(d, 3H-adamantane); 1.62(s, 2xCH₂); 1.60-2.05(m, 10H-adamantane); 2.55(s, CH3); 3.92(d, CH); 7.04 and 7.22(2xd, 2H-aromatic); 7.56(t, H-aromatic); 8.33(d, NH) | |
| 277 | CDCl₃: 1.25-1.49(m, 4H-adamantane); 1.45(s, 3x CH₃); 1.54(s, 2xCH₃); 1.64-2.04(m, 10H-aromatic, CH₂); 2.43(s, CH3); 2.60 and 2.91(2xt, 2x CH₂); 3.22-3.57(m, 8h-homopiperidine); 3.92(d, CH); 5.47(d, NH); 6.95 and 7.04(2xs, 3H-aromatic). | |

C. Pharmacological Examples

Example C.1

Enzymatic Assays to Test the Effect of Compounds on 11b-Hydroxysteroid Dehydrogenase Type 1 and Type 2

The effects of compounds on 11β-HSD1 dependent conversion of cortisone into cortisol (reductase activity) was studied in a reaction mixture containing 30 mM Tris-HCl buffer pH 7.2, 180 μM NADPH, 1 mM EDTA, 2 μM cortisone, 1 μl drug and/or solvent and 11 μg recombinant protein in a final volume of 100 μl.

The effect on the 11b-HSD1-dehydrogenase activity (conversion of cortisol into cortisone) was measured in a reaction mixture containing 0.1 M sodium phosphate buffer pH 9.0, 300 μM NADP, 25 μM cortisol, 1 μl drug and/or solvent and 3.5 μg recombinant protein in a final volume of 100 μl.

The effects on the 11b-HSD2 dependent dehydrogenase activity was studied in a reaction mixture containing 0.1 M sodium phosphate buffer pH 7.5, 300 μM NAD, 100 nM cortisol (of which 2 nM is 3H-radio labelled), 1 μl drug and/or solvent and 2.5 μg recombinant protein in a final volume of 100 μl.

All incubations were performed for 45 min at 37 C in a water bath. The reaction was stopped by adding 100 μl acetonitrile containing 20 μg corticosterone as internal standard. After centrifugation, the product formation was analysed in the supernatant by HPLC on a Hypersyl BDS-C18 column using 0.05 mM ammonium acetate/methanol (50/50) as solvent. In all of the aforementioned assays, the drugs to be tested were taken from a stock solution and tested at a final concentration ranging from $-10^{-5}$ M to $3.10^{-9}$ M. From the thus obtained dose response curves, the pIC50 value was calculated and scored as follows; Score 1=pIC50 value<5, Score 2=pIC50 value in the range of 5 to 6, Score 3=pIC50 value>6. Some of the thus obtained results are summarized in the table below. (in this table NT stands for Not Tested).

Example C2

Cellular Assays to Test the Effect of Compounds on 11b-Hydroxysteroid Dehydrogenase Type 1 and Type 2

The effects on 11b-HSD1 activity was measured in differentiated 3T3-L1 cells and rat hepatocytes.

Mouse fibroblast 3T3-L1 cells (ATCC-CL-173) were seeded at a density of 16500 cells/ml in 12 well plates and grown for 7 days in DMEM medium (supplemented with 10% heat inactivated foetal calf serum, 2 mM glutamine and 25 mg gentamycin) at 37 C in a humidified 5% CO₂ atmosphere. Medium was refreshed twice a week. Fibroblasts were differentiated into adipocytes at 37 C in a 5%

CO$_2$ humidified atmosphere in growth medium containing 2 μg/ml insulin, 55 μg/ml IBMX and 39.2 μg/ml dexamethasone.

Primary hepatocytes from male rats were seeded on BD-Biocoat Matrigel matrix multiwell plates at a density of 250000 cells/well and incubated for 10 days at 37 C in a 5% CO$_2$ humidified atmosphere in DMEM-HAM's F12 medium containing 5% Nu-serum, 100 U/ml penicillin, 100 μg/ml streptomycin, 0.25 μg/ml amphotericin B, 50 μg/ml gentamycin sulfate, 5 μg/ml insulin and 392 ng/ml dexamethasone. Medium was refreshed 3 times a week.

Following a 4 hour pre-incubation with test compound, 0.5 μCi $^3$H-cortisone or dehydrocorticosterone, was added to the cultures. One hour later, the medium was extracted on Extrelut$^3$-columns with 15 ml diethyl ether and the extract was analysed by HPLC as described above.

The effects on 11b-HSD2 activity was studied in HepG2 and LCC-PK1-cells HepG2-cells (ATCC HB-8065) were seeded in 12 well plates at a density of 100,000 cells/ml and grown at 37 C in a humidified 5% CO$_2$ atmosphere in MEM-Rega-3 medium supplemented with 10% heat inactivated foetal calf serum, 2 mM L-glutamine and sodium bicarbonate). Medium was refreshed twice a week.

Pig kidney cells (LCC-PK1, ATCC CRL-1392) were seeded at a density of 150,000 cells/ml in 12 well plates and grown at 37 C in a humidified 5% CO2 atmosphere in Medium 199 supplemented with Earls modified salt solution, 100 U/ml penicillin, 100 μg/ml streptomycin and 10% foetal calf serum. Medium was refreshed twice a week. Twenty four hours prior to the onset of the experiment, medium was changed by medium containing 10% charcoal stripped foetal calf serum.

Following a 4 hour pre-incubation with test compound, 0.5 μCi $^3$H-cortisol or corticosterone, was added to the cultures. One hour later, the medium was extracted on Extrelut$^3$-columns with 15 ml diethyl ether and the extract was analysed by HPLC as described above.

As for the enzymatic assays, the compounds to be tested were taken from a stock solution and tested at a final concentration ranging from $-10^{-5}$ M to $3.10^{-9}$ M. From the thus obtained dose response curves, the pIC50 value was calculated and scored as follows; Score 1=pIC50 value<5, Score 2=pIC50 value in the range of 5 to 6, Score 3=pIC50 value>6. Some of the thus obtained results are summarized in the table below. (in this table NT stands for Not Tested).

| Example Number | Compound Number | [C1] HSD1-prot Reduct Score | [C1] HSD2 prot Dehydro Score | [C2] HSD1 cellular 3T3-L1 Score | [C2] HSD2 cellular HepG2 Score |
|---|---|---|---|---|---|
| B3 | 16 | NT | 1 | 2 | 1 |
| B12 | 19 | NT | 1 | 2 | 1 |
| B12 | 22 | NT | 1 | 2 | 1 |
| B1 | 1 | NT | 1 | 3 | 1 |
| B1 | 28 | NT | NT | 3 | 1 |
| B1 | 29 | NT | NT | 3 | 1 |
| B1 | 30 | NT | NT | 3 | 1 |
| B13 | 31 | NT | 1 | 3 | 1 |
| B13 | 35 | NT | 1 | 2 | 1 |
| B1 | 41 | 3 | 1 | 3 | 1 |
| B1 | 43 | 3 | 1 | 2 | 1 |
| B1 | 46 | 1 | 1 | 3 | 1 |
| B4 | 47 | 3 | 1 | 3 | 1 |
| B4 | 48 | 1 | 1 | 3 | 1 |
| B1 | 126 | 3 | 1 | 3 | 1 |
| B1 | 127 | 1 | 1 | 3 | 1 |
| B4 | 5 | 3 | 1 | 3 | 1 |
| B1 | 50 | 1 | 1 | 2 | 1 |
| B1 | 51 | 1 | 1 | 2 | 1 |
| B1 | 52 | 1 | 1 | 3 | 1 |
| B5 | 53 | 1 | 1 | 3 | 1 |
| B5 | 54 | 2 | 1 | 3 | 1 |
| B13 | 55 | NT | 1 | 3 | 1 |
| B13 | 56 | NT | 1 | 2 | 1 |
| B13 | 57 | NT | 1 | 2 | 1 |
| B1 | 64 | NT | 1 | 2 | 1 |
| B4 | 6 | 2 | 1 | 3 | 1 |
| B6 | 128 | 3 | 1 | 3 | 1 |
| B1 | 129 | 2 | 1 | 2 | 1 |
| B1 | 68 | 2 | 1 | 2 | 1 |
| B5 | 71 | 3 | NT | 3 | 1 |
| B5 | 7 | 1 | NT | 3 | 1 |
| B1 | 72 | 2 | 1 | 3 | 1 |
| B5 | 73 | 1 | 1 | 3 | 1 |
| B4 | 74 | 3 | 1 | 3 | 1 |
| B1 | 133 | 1 | 1 | 3 | 1 |
| B1 | 77 | 1 | 2 | 3 | 1 |
| B1 | 78 | 3 | 2 | 3 | 1 |
| B1 | 81 | 3 | NT | 2 | 1 |
| B1 | 84 | 1 | 1 | 3 | 1 |
| B1 | 85 | 1 | 1 | 3 | 1 |
| B1 | 86 | 1 | 1 | 3 | 1 |
| B1 | 87 | 1 | 1 | 3 | 1 |
| B1 | 88 | 1 | 1 | 3 | 1 |
| B1 | 89 | 3 | 1 | 3 | 1 |
| B1 | 137 | 3 | 1 | 3 | 1 |
| B1 | 138 | 1 | 1 | 3 | 1 |
| B1 | 91 | 1 | 1 | 3 | 1 |
| B1 | 151 | 2 | 1 | 3 | 1 |
| B1 | 153 | 2 | 1 | 3 | 1 |
| B1 | 140 | 3 | 1 | 3 | 1 |
| B1 | 141 | 3 | 1 | 3 | 1 |
| B5 | 92 | 3 | 1 | 3 | 1 |
| B1 | 93 | 3 | NT | 3 | 1 |
| B1 | 154 | 1 | NT | 3 | 1 |
| B1 | 95 | 1 | NT | 3 | 1 |
| B1 | 144 | 3 | NT | 3 | 1 |
| B1 | 106 | 1 | NT | 3 | 1 |
| B3 | 3 | 3 | NT | 3 | 1 |
| B6 | 109 | 3 | NT | 3 | 1 |
| B1 | 162 | 3 | 1 | 3 | 1 |
| B18 | 166 | 3 | 1 | 3 | 1 |
| B1 | 167 | 3 | 1 | 3 | 1 |
| B1 | 168 | 3 | 1 | 3 | 1 |
| B1 | 169 | 3 | 1 | 3 | 1 |
| B1 | 171 | 3 | 1 | 3 | 1 |
| B1 | 177 | 3 | 1 | 3 | 1 |
| B1 | 181 | 1 | 1 | 3 | 1 |
| B1 | 182 | 3 | 1 | 3 | 1 |
| B1 | 158 | 1 | 1 | 3 | 1 |
| B15 | 191 | 3 | 1 | 3 | 1 |
| B16 | 193 | 3 | 1 | 3 | 1 |
| B16 | 196 | 3 | 1 | 3 | 1 |
| B1 | 197 | 1 | 1 | 3 | 1 |
| B22 | 198 | 1 | 1 | 3 | 1 |
| B1 | 203 | 1 | 1 | 3 | 1 |
| B1 | 210 | 1 | 1 | 3 | 1 |
| B22 | 217 | 2 | 1 | 3 | 1 |
| B1 | 223 | 3 | 1 | 3 | 1 |
| B1 | 224 | 3 | 1 | 3 | 1 |
| B16 | 230 | 3 | 1 | 3 | 1 |
| B20 | 236 | 3 | 1 | 3 | 1 |
| B16 | 240 | 1 | 1 | 3 | 1 |
| B16 | 242 | 2 | 1 | 3 | 1 |
| B1 | 243 | 3 | 1 | 3 | 1 |
| B16 | 248 | 3 | 1 | 3 | 1 |
| B7 | 251 | 3 | 1 | 3 | 1 |
| B14 | 253 | NT | 1 | 3 | 1 |
| B16 | 254 | 1 | 1 | 3 | 1 |

| Example Number | Compound Number | [C1] HSD1-prot Reduct Score | [C1] HSD2 prot Dehydro Score | [C2] HSD1 cellular 3T3-L1 Score | [C2] HSD2 cellular HepG2 Score |
|---|---|---|---|---|---|
| B23 | 255 | NT | 1 | 3 | 1 |
| B16 | 258 | 3 | 1 | 3 | 1 |
| B7 | 263 | 1 | 1 | 3 | 1 |

D. Composition Examples

The following formulations exemplify typical pharmaceutical compositions suitable for systemic or topical administration to animal and human subjects in accordance with the present invention.

"Active ingredient" (A.I.) as used throughout these examples relates to a compound of formula (I) or a pharmaceutically acceptable addition salt thereof.

Example D.1

Film-coated Tablets

Preparation of Tablet Core

A mixture of A.I. (100 g), lactose (570 g) and starch (200 g) was mixed well and thereafter humidified with a solution of sodium dodecyl sulfate (5 g) and polyvinyl-pyrrolidone (10 g) in about 200 ml of water. The wet powder mixture was sieved, dried and sieved again. Then there was added microcrystalline cellulose (100 g) and hydrogenated vegetable oil (15 g). The whole was mixed well and compressed into tablets, giving 10.000 tablets, each comprising 10 mg of the active ingredient.

Coating

To a solution of methyl cellulose (10 g) in denaturated ethanol (75 ml) there was added a solution of ethyl cellulose (5 g) in $CH_2Cl_2$ (150 ml). Then there were added $CH_2Cl_2$ (75 ml) and 1,2,3-propanetriol (2.5 ml). Polyethylene glycol (10 g) was molten and dissolved in dichloromethane (75 ml). The latter solution was added to the former and then there were added magnesium octadecanoate (2.5 g), polyvinyl-pyrrolidone (5 g) and concentrated color suspension (30 ml) and the whole was homogenated. The tablet cores were coated with the thus obtained mixture in a coating apparatus.

The invention claimed is:

1. A compound of formula (I')

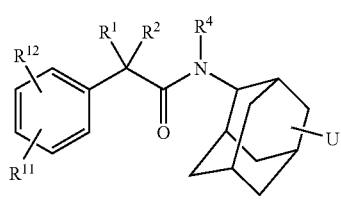

(I')

or an N-oxide form, a pharamceutically acceptable addition salt or a stereochemically isomeric form thereof wherein $R^1$ and $R^2$ each independently represents hydrogen, $C_{1-4}$alkyl, $NR^9R^{10}$, $C_{1-4}$alkyloxy or $Het^3$-O-$C_{1-4}$alkyl; or $R^1$ and $R^2$ taken together with the carbon atom with which they are attached from a $C_{3-6}$cycloalkyl;

$R^4$ represents hydrogen, $C_{1-4}$alkyl, or $C_{2-4}$alkenyl;

U represents $C_{1-4}$alkyloxy, phenyl, halo, oxo, carbonyl or hydroxyl;

$R^5$ and $R^6$ are each independently selected from hydrogen, $C_{1-4}$alkyl, $C_{1-4}$alkyloxy$C_{1-4}$alkyl, $C_{1-4}$alkyloxycarbonyl, $C_{1-4}$alkylcarbonyl, $C_{1-4}$alkylcarbonyl substituted with one or where possible two or three substituents each independently selected from halo, $C_{1-4}$alkyl, and $C_{1-4}$alkyloxy or $R^5$ and $R^6$ each independently represent $C_{1-4}$alkyl substituted with phenyl;

$R^7$ and $R^8$ are each independently selected from hydrogen or $C_{1-4}$alkyl;

$R^9$ and $R^{10}$ are each independently selected from hydrogen, $C_{1-4}$alkyl or $C_{1-4}$alkyloxycarbonyl;

$R^{11}$ and $R^{12}$ are each independently selected from hydrogen, halo, $C_{1-4}$alkyl, $C_{1-4}$alkyloxy, hydroxy, nitro, $Het^4$, phenyl, phenyloxy, $C_{1-4}$alkyloxycarbonyl, hydroxycarbonyl, $NR^5R^6$, $C_{1-4}$alkyloxy substituted with one or where possible two or three substituents each independently selected from hydroxycarbonyl, $Het^2$ and $NR^7R^8$, $C_{2-4}$alkenyl substituted with one substituent selected from phenyl-$C_{1-4}$alkyl-oxycarbonyl, $C_{1-4}$alkyloxycarbonyl, hydroxycarbonyl, $Het^5$-carbonyl, and $C_{1-4}$alkyl substituted with one or where possible two or three substituents each independently selected from halo, dimethylamine, trimethylamine, amine, cyano, $Het^6$, $Het^7$-carbonyl, $C_{1-4}$alkyloxycarbonyl or hydroxycarbonyl;

$Het^2$ represents a monocyclic heterocycle selected from piperidinyl, pyridinyl, pyridazinyl, pyrimidinyl, pyrazinyl, piperazinyl, 2H-pyrrolyl, pyrrolyl, 2-pyrrolinyl, 3-pyrrolinyl, pyrrolidinyl, or morpholinyl, said $Het^2$ optionally being substituted with one or where possible two or more substituents each independently selected from hydroxy, carbonyl, $C_{1-4}$alkyl or $C_{1-4}$alkyloxy;

$Het^3$ represents a monocyclic heterocycle selected from 2H-pyranyl, 4H-pyranyl, furanyl, tetrahydro-2H-pyranyl, pyridinyl, piperidinyl, or furanyl;

$Het^4$ represents a monocyclic heterocycle selected from pyridazinyl, pyrimidinyl, pyrrolidinyl, pyrazinyl, piperazinyl, triazolyl, tetrazolyl or morpholinyl, said $Het^4$ optionally being substituted with one or where possible two or more substituents each independently selected from hydroxy, carbonyl, $C_{1-4}$alkyl or $C_{1-4}$alkyloxy;

$Het^5$ represents a monocyclic heterocycle selected from pyridazinyl, pyrimidinyl, pyrrolidinyl, pyrazinyl, piperazinyl or morpholinyl, said $Het^5$ optionally being substituted with one or where possible two or more substituents each independently selected from hydroxy, carbonyl, $C_{1-4}$alkyl or $C_{1-4}$alkyloxy;

$Het^6$ represents a monocyclic heterocycle selected from pyridazinyl, pyrimidinyl, pyrrolidinyl, pyrazinyl, piperazinyl or morpholinyl, said $Het^6$ optionally being substituted with one or where possible two or more substituents each independently selected from hydroxy, carbonyl, $C_{1-4}$alkyl or $C_{1-4}$alkyloxy; and $Het^7$ represents a monocyclic heterocycle selected from pyridazinyl, pyrimidinyl, pyrrolidinyl, pyrazinyl, piperazinyl or morpholinyl, said $Het^7$ optionally being substituted with one or where possible two or more substituents each independently selected from hydroxy, carbonyl, $C_{1-4}$alkyl or $C_{1-4}$alkyloxy.

2. A compound according to claim 1, wherein $R^1$ and $R^2$ each independently represents hydrogen, $C_{1-4}$alkyl, or $C_{1-4}$alkyloxy.

3. A compound according to claim 1, wherein $R^1$ and $R^2$ each independently represents methyl or methoxy.

4. A compound according to claim 1, wherein $R^1$ and $R^2$ taken together with the carbon atom with which they are attached form cyclopropyl or cyclobutyl.

5. A compound according to claim 1, wherein $R^4$ represents hydrogen.

6. A compound according to claim 1, wherein U represents, hydroxy or halo.

7. A compound according to claim 1, wherein $Het^5$ represents a monocyclic heterocycle selected from piperazinyl or morpholinyl.

8. A compound according to claim 1, wherein $Het^7$ represents a monocyclic heterocycle selected from piperazinyl or morpholinyl.

9. A pharmaceutical composition comprising a pharmaceutically acceptable carrier and a compound of claim 1.

10. A compound according to claim 1, wherein the compound is selected from:
(1α,2β,3β,5β,7β)-N-(5-hydroxytricyclo[3.3.1.13,7]dec-2-yl)-α,α-dimethyl-benzeneacetamide;
(1α,2β,3β,5β,7β)-N-(5-hydroxytricyclo[3.3.1.13,7]dec-2-yl)-α,α-dimethyl-3-methyl-benzeneacetamide;
(1α,2β,3β,5β,7β)-N-(5-hydroxytricyclo[3.3.1.13,7]dec-2-yl)-α,α-dimethyl-3-methoxy-benzeneacetamide;
(1α,2β,3β,5β,7β)-N-(5-hydroxytricyclo[3.3.1.13,7]dec-2-yl)-α,α-dimethyl-3-hydroxy-benzeneacetamide;
(1α,2β,3β,5β,7β)-N-(5-hydroxytricyclo[3.3.1.13,7]dec-2-yl)-α,α-dimethyl-3,5-dimethyl-benzeneacetamide);
(1α,2β,3β,5β,7β)-N-(5-hydroxytricyclo[3.3.1.13,7]dec-2-yl)-α,α-dimethyl-3-(carboxymethoxy)-benzeneacetamide;
(1α,2β,3β,5β,7β)-N-(5-hydroxytricyclo[3.3.1.13,7]dec-2-yl)-α,α-dimethyl-3-[2-(4-morpholinyl)ethoxy]-benzeneacetamide;
(1α,2β,3β,5β,7β)-N-(5-fluorotricyclo[3.3.1.13,7]dec-2-yl)-α,α-dimethyl-benzeneacetamide;
(1α,2β,3β,5β,7β)-N-(5-methoxytricyclo[3.3.1.13,7]dec-2-yl)-α,α-dimethyl-benzeneacetamide;
(1α,2α,3β,5β,7β)-N-(5-methoxytricyclo[3.3.1.13,7]dec-2-yl)-α,α-dimethyl-benzeneacetamide;
3-(3-{2-[(5-fluoro-2-adamantyl)amino]-1,1-dimethyl-2-oxoethyl}-5-methylphenyl)propanoic acid; and
4-(3-{2-[(5-hydroxy-2-adamantyl)amino]-1,1-dimethyl-2-oxoethyl}-5-methylphenyl)butanoic acid;
or a N-oxide, a pharmaceutically acceptable addition salt or a stereochemically isomeric form thereof.

11. A compound according to claim 1 wherein the compound is selected from
(1α,2β,3β,5β,7β)-N-(5-hydroxytricyclo[3.3.1.13,7]dec-2-yl)-α,α-dimethyl-benzeneacetamide;
(1α,2β,3β,5β,7β)-N-(5-hydroxytricyclo[3.3.1.13,7]dec-2-yl)-α,α-dimethyl-3-methyl-benzeneacetamide; and
(1α,2β, 3β,5β,7β)-N-(5-hydroxytricyclo[3.3.1.13,7]dec-2-yl)-α,α-dimethyl-3-methoxy-benzeneacetamide; or a N-oxide, a pharmaceutically acceptable addition salt or a stereochemically isomeric form thereof.

12. A compound according to claim 1 wherein the compound is

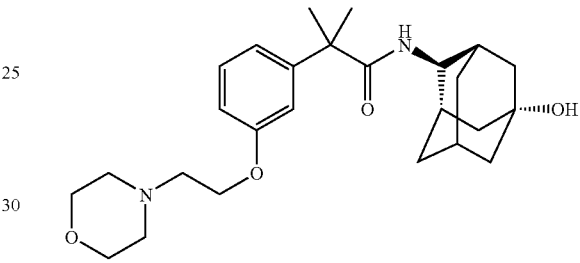

or a N-oxide, a pharmaceutically acceptable addition salt or a stereochemically isomeric form thereof.

13. A compound according to claim 1 wherein $R^1$ and $R^2$ each represent $C_{1-4}$alkyl.

* * * * *